United States Patent
Jacobs et al.

(10) Patent No.: US 11,083,715 B2
(45) Date of Patent: *Aug. 10, 2021

(54) COMPOSITIONS COMPRISING CYTISINE IN THE TREATMENT AND/OR PREVENTION OF ADDICTION IN SUBJECTS IN NEED THEREOF

(71) Applicant: Achieve Life Sciences, Inc., Bothell, WA (US)

(72) Inventors: Cindy A. Jacobs, Fall City, WA (US); Daniel F. Cain, Vashon, WA (US); Anthony Clarke, Checkendon (GB)

(73) Assignee: Achieve Life Sciences, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/993,522

(22) Filed: Aug. 14, 2020

(65) Prior Publication Data

US 2021/0077473 A1 Mar. 18, 2021

Related U.S. Application Data

(60) Provisional application No. 62/899,637, filed on Sep. 12, 2019, provisional application No. 62/988,890, filed on Mar. 12, 2020.

(51) Int. Cl.
*A61K 31/439* (2006.01)
*A61P 25/34* (2006.01)

(52) U.S. Cl.
CPC .......... *A61K 31/439* (2013.01); *A61P 25/34* (2018.01)

(58) Field of Classification Search
CPC .................................................. A61K 31/439
USPC ........................................................ 514/292
See application file for complete search history.

(56) References Cited

U.S. PATENT DOCUMENTS

| 4,971,079 A | 11/1990 | Talapin et al. |
| 2019/0099407 A1 | 4/2019 | Takagi et al. |

OTHER PUBLICATIONS

Tutka, Addiction, 2019, 114, 1951-1969.*
Jeong, Xenobiotica 2019, vol. 49, No. 11, 1332-1337.*
Achieve Life Sciences Oct. 30, 2018, 05:30 ET.*
Berta, CNS Drugs (2016) 30:951-983.*
Achieve, Protocol ACH-CYT-02, Sep. 21, 2017, Version 2.0.*
Beard, CNS Drugs (2016) 30:951-983.*
Tutka, Addiction, 114, 1951-1969, 2019.*
Cappelleri et al., "Revealing the multidimensional framework of the Minnesota nicotine withdrawal scale," Curr Med Res Opin. 21(5):749-60 (publication date: May 2005).
Cox et al., "Evaluation of the brief questionnaire of smoking urges (QSU-brief) in laboratory and clinical settings," Nicotine Tob Res. 3(1):7-16 (publication date: Feb. 2001).
Etter et al., "Development and validation of a scale measuring self-efficacy of current and former smokers," Addiction. 95(6):901-13 (publication date: Jun. 2000).
Foulds et al., "Effect of varenicline on individual nicotine withdrawal symptoms: a combined analysis of eight randomized, placebo-controlled trials," Nicotine Tob Res. 15(11):1849-57 (publication date: Nov. 2013, epublication date: May 31, 2013).
Heatherton et al., "The Fagerström Test for Nicotine Dependence: a revision of the Fagerström Tolerance Questionnaire," Br J Addict. 86(9):1119-27 (publication date: Sep. 1991).
International Search Report and Written Opinion dated Nov. 10, 2020 for International Application No. PCT/US2020/046308.
Jeong. "Cytisine concentration-effect relationships in human smokers," University of Auckland Research Repository [Online], 2015 [retrieved pm Oct. 19, 2020]. Retrieved from the Internet: <https://researchspace.auckland.ac.nz/bitstream/handle/2292/27997/whole.pdf?sequence=38> p. 13, para 2; p. 21, para 2; p. 22, Table 2.1; p. 31, para 4; p. 34, para 2.
Posner et al., "The Columbia-Suicide Severity Rating Scale: Initial validity and internal consistency findings from three multisite studies with adolescents and adults," Am J Psychiatry. 168(12):1266-77 (publication date: Dec. 2011).
Stern, "The hospital anxiety and depression scale," Occup Med (Lond). 64(5):393-4 (publication date: Jul. 2014).
Thomas et al., "A Table of Exact Confidence Limits for Differences and Ratios of Two Proportions and Their Odds Ratios," Journal of the American Statistical Association. 72(357):73-76 (publication date: Mar. 1977).
Thomas, "Exact Confidence Limits for the Odds Ratio in a 2 × 2 Table," Journal of the Royal Statistical Society Series C (Applied Statistics) 20:105-10 (1971).
Vinnikov et al., "A Double-Blind, Randomised, Placebo-Controlled Trial of Cytisine for Smoking Cessation in Medium-Dependent Workers," Journal of Smoking Cessation 3(1):57-62 (2008).
West et al., "Is the ten-item Questionnaire of Smoking Urges (QSU-brief) more sensitive to abstinence than shorter craving measures?" Psychopharmacology (Berl). 208(3):427-32 (epublication date: Dec. 22, 2009).
West et al., "Outcome criteria in smoking cessation trials: proposal for a common standard," Addiction. 100(3):299-303 (publication date: Mar. 2005).
Yan X et al., "Missing data handling methods in medical device clinical trials," J Biopharm Stat. 19(6)1085-98 (publication date: Nov. 2009).

(Continued)

*Primary Examiner* — Nizal S Chandrakumar
(74) *Attorney, Agent, or Firm* — Perkins Coie LLP

(57) ABSTRACT

Methods of treatment of addiction and/or dependence, methods of promoting cessation of various addictions, such as smoking and/or vaping, and methods of promoting a reduction in various addictions, such as smoking and/or vaping, uses of cytisine as an addiction cessation treatment, and dosage regimens for the foregoing are provided.

6 Claims, 34 Drawing Sheets

(56) References Cited

OTHER PUBLICATIONS

"How to Quit Smoking Forever with Tabex," Quit with Tabex [Online], [retrieved on Oct. 19, 2020]. Retrieved from the Internet: <URL:www.tabex.net>.

Jeong, "Cytisine concentration-effect relationships in human smokers," University of Auckland Research Repository [Online], 2015 [retrieved Oct. 19, 2020]. Retrieved from the Internet: <https://researchspace.auckland.ac.nz/bitstream/handle/2292/27997/whole.pdf?sequence=38> p. 13, para 2; p. 21, para 2; p. 22, Table 2.1; p. 31, para 4; p. 34, para 2.

Yu et al., "Recent Developments in Novel Antidepressants Targeting α4β2-Nicotinic Acetylcholine Receptors," Journal of Medicinal Chemistry, 57:8204-8223 (publication date: Oct. 23, 2014; epublication date: Jun. 5, 2014).

\* cited by examiner

| Traditional downward titration | | | | |
|---|---|---|---|---|
| Day | Number of Days | Daily Frequency | Total Dose (mg) 1.5 mg | Total Dose (mg) 3.0 mg |
| 1 - 3 | 3 | 6 times | 9 | 18 |
| 4 - 12 | 9 | 5 times | 7.5 | 15 |
| 13 - 16 | 4 | 4 times | 6 | 12 |
| 17 - 20 | 4 | 3 times | 4.5 | 9 |
| 21 - 24 | 4 | 2 times | 3 | 6 |
| 25 | 1 | 1 time only | 1.5 | 3 |
| TOTAL | | | 150 mg | 300 mg |

| Simplified 3-times daily (TID) | | | | |
|---|---|---|---|---|
| Day | Number of Days | Daily Frequency | Total Dose (mg) 1.5 mg | Total Dose (mg) 3.0 mg |
| 1 - 20 | 20 | 3 times | 4.5 | 9 |
| 21 - 24 | 4 | 2 times | 3 | 6 |
| 25 | 1 | 1 time only | 1.5 | 3 |
| TOTAL | | | 103.5 mg | 207 mg |

*FIG. 1*

|  | TID | | Downward Titration | | Pooled Placebo (n=51) | ALL (n=254) |
|---|---|---|---|---|---|---|
|  | 1.5 mg (n=52) | 3.0 mg (n=50) | 1.5 mg (n=51) | 3.0 mg (n=50) | | |
| Completed 25-day treatment | 51 (98.1%) | 48 (96.0%) | 47 (92.2%) | 44 (88.0%) | 48 (94.1%) | 239 (94.1%) |
| Discontinued early | 1 (1.9%) | 1 (2.0%) | 4 (7.8%) | 6 (12%) | 3 (5.9%) | 15 (5.9%) |
| Reason | | | | | | |
| Adverse Event | 1 | 0 | 1 | 1 | 2 | 5 |
| Withdraw by subject | 0 | 0 | 3 | 5 | 0 | 8 |
| Lost to F/U | 0 | 0 | 0 | 0 | 1 | 1 |
| Other | 0 | 1 | 0 | 0 | 0 | 1 |

FIG. 4

Treatment duration
- Cytisinicline     25 days
- Chantix           12 weeks

Sustained Abstinence Timepoints
- Cytisinicline     8 weeks
  (measured 4 weeks after end of treatment, OFF drug)
- Chantix           12 weeks
  (measured over last 4 weeks on treatment, ON drug)

| Week | 1 | 2 | 3 | 4 | 5 | 6 | 7 | 8 | 9 | 10 | 11 | 12 |
|------|---|---|---|---|---|---|---|---|---|----|----|----|
| Day  | 0 | 7 | 14 | 21 | 25 | 28 | 35 | 42 | 49 | 56 | 63 | 70 | 77 | 84 |

Chantix: Treatment — Grace Period 8 weeks — 4 week Continuous Abstinence

ORCA-1: Treatment — Grace Period 25 days — 4 week Continuous Abstinence — Post Treatment X = CO confirmed 7 day point prevalence abstinence (i.e. have you smoked today or in the last 7 days)
Y = CO confirmed end of treatment point prevalence abstinence (i.e. have you smoked today)

ACHIEVE LIFE SCIENCES

*FIG. 12*

COMPOSITIONS COMPRISING CYTISINE IN THE TREATMENT AND/OR PREVENTION OF ADDICTION IN SUBJECTS IN NEED THEREOF

PRIORITY CLAIM

This application claims priority to U.S. Provisional Application No. 62/988,890 filed on Mar. 12, 2020 and U.S. Provisional Application No. 62/899,637 filed on Sep. 12, 2019, the entire contents of each of which are incorporated herein by reference and relied upon.

BACKGROUND

Nicotine is an addictive substance that is rapidly absorbed during cigarette smoking. The drug distributes quickly and is thought to interact with neuronal nicotinic acetylcholine receptors (nAChRs) in the central nervous system (CNS). Nicotine addiction results, at least in part, from this interaction. Although many smokers attempt to cease smoking, few succeed without pharmacological supportive treatment.

Tobacco smoking contributes to some 7 million premature deaths each year worldwide. Smoking is highly addictive, with more than 95% of unaided attempts at cessation failing to last 6 months. It has been estimated that for every year that a person delays stopping smoking beyond his or her mid-30s, that person loses 3 months of life expectancy. The World Health Organization's Framework Convention on Tobacco Control identifies evidence-based approaches to promote smoking cessation, which include mass-media campaigns, tax increases on tobacco, and help for smokers wanting to stop.

The pharmacotherapies currently available in the U.S. and Western Europe to help smokers stop include nicotine replacement therapy (NRT) and two non-nicotine containing medications: bupropion (Zyban®, Glaxo-SmithKline) and varenicline (Chantix®/Champix®, Pfizer). NRT and bupropion appear to have about equal efficacy. Varenicline is more effective than single NRT and bupropion, although combination NRT is comparable in efficacy.

(−)-Cytisine (cytisinicline; commonly referred to simply as cytisine) is a plant-based alkaloid isolated from seeds of *Cytisus laburnum* L. (Golden chain). References herein to cytisine refer to (−)-cytisine, cytisinicline.

Cytisine's mechanism of action has assisted basic pharmacologists in understanding the complex pharmacology of the various subtypes of the nicotinic acetylcholine receptor. These studies have shown that both nicotine and cytisine bind strongly and preferentially to alpha4, beta2 ($\alpha_4\beta_2$) receptors that mediate the release of dopamine in the shell of the nucleus accumbens and elsewhere. This receptor subtype has been implicated in the development and maintenance of nicotine dependence and was the primary target for the drug varenicline, referred to above.

Tabex®, containing the active substance cytisine, has been licensed and marketed in Central and Eastern Europe for several decades by Sopharma PLC (Sophia, Bulgaria).

A need exists for nicotine addiction treatments with patient-friendly regimens that are less costly, more effective, have an improved safety profile, and/or can more successfully treat individuals who have failed to quit nicotine using the known treatments.

SUMMARY

In one aspect, provided herein is a method of treating of nicotine addiction in a subject, comprising administering cytisine in equal dosage amounts two times per day ("bid" or "BID") or three times per day ("tid" or "TID") to a subject in need thereof.

In another aspect, provided herein is a method of treating nicotine addiction, promoting cessation of smoking, and/or promoting a reduction in smoking in a subject in need thereof, the method comprising administering cytisine provided in a unit dose of 3.0 mg or 1.5 mg of cytisine three times daily to the subject.

In still another aspect, provided herein is a method of treating nicotine addiction in a subject, comprising administering cytisine at a dose of either 1.5 mg or 3.0 mg of cytisine three times daily to a subject in need thereof.

In still another aspect, provided herein is a method of treating nicotine dependence in a subject, comprising administering cytisine at a dose of either 1.5 mg or 3.0 mg of cytisine three times daily to a subject in need thereof.

In still yet another aspect, provided herein is a method of treating nicotine addiction in a subject, comprising administering cytisine to a subject in need thereof, wherein the subject is a refractory patient who has failed treatment with one or more nicotine addiction treatments.

In yet another aspect, provided herein is a method of preventing smoking relapse in a subject in need thereof, the method comprising administering cytisine provided in a unit dose of (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, three times daily to the subject.

In a further aspect, provided herein is a method of preventing smoking relapse in a subject in need thereof, the method comprising administering cytisine to the subject, wherein the subject is a refractory patient who has failed treatment with one or more smoking cessation treatments selected from the group consisting of NRT, administration of bupropion, administration of varenicline, electronic cigarettes (e-cigarettes), and vaping.

In one embodiment, each of the three daily administrations occur morning, noon, and evening, respectively, or in approximately intervals of 4-5 hours. In one embodiment, the administration occurs for a period of at least about 6 weeks, at least about 12 weeks, at least about 24 weeks or indefinitely. In another embodiment, the administration occurs for a period of at least about 6 weeks or at least about 12 weeks or repeated for 6-12 weeks indefinitely.

In some embodiments, cytisine is provided in a unit dose of about 1.0 mg to about 6.0 mg of cytisine one to six times daily to a subject in need thereof. In some embodiments, cytisine is provided in a unit dose of about 1.0 mg to about 6.0 mg of cytisine three to six times daily to a subject in need thereof. In some embodiments, cytisine is provided in a unit dose of 1.5 mg of cytisine three times daily to a subject in need thereof. In some embodiments, cytisine is provided in a unit dose of 1.5 mg of cytisine six times daily to a subject in need thereof. In some embodiments, cytisine is provided in a unit dose of 3.0 mg of cytisine three times daily to a subject in need thereof. In some embodiments, cytisine is provided in a unit dose of 3.0 mg of cytisine six times daily to a subject in need thereof.

In some embodiments, the cytisine is administered in one or more unit doses. In some embodiments, each unit dose (e.g., a tablet or a capsule) of cytisine comprises 1.0 mg of cytisine. In some embodiments, each unit dose (e.g., a tablet or a capsule) of cytisine comprises 1.5 mg of cytisine. In some embodiments, the unit dose of cytisine comprises 3.0 mg of cytisine. In some embodiments, each unit dose is a tablet, for example, a compressed, film coated tablet.

In some embodiments, the subject is a refractory patient who has failed treatment with one or more nicotine addiction treatments. In some embodiments, the subject is a refractory patient who has failed treatment with two or more nicotine addiction treatments. In some embodiments, the nicotine addiction treatments are selected from NRT, administration of bupropion, administration of varenicline, electronic cigarettes, vaping, and a combination thereof.

In some embodiments, the subject smoked ten or more cigarettes per day prior to the administration of cytisine. In some embodiments, the subject has expired air carbon monoxide (CO) concentration of about 10 parts per million (ppm) or greater prior to the administration of cytisine. In some embodiments, the subject (a) smoked ten or more cigarettes per day prior to the administration of cytisine, (b) has expired air CO concentration of about 10 ppm or greater prior to the administration of cytisine, or (c) a combination of (a) and (b).

In some embodiments, the subject experiences no adverse events after receiving the cytisine treatment. In some embodiments, the adverse event is selected from the group consisting of an upper respiratory tract infection (URTI), abnormal dreams, nausea, insomnia, headache, fatigue, and constipation.

In some embodiments, the method further comprises providing behavioral support to the subject.

BRIEF DESCRIPTION OF THE DRAWINGS

FIG. 1 is a schematic of dosing schedules according to the study design of Example 1 in accordance with the present technology.

FIG. 4 is a schematic showing the subject population disposition according to the study of Example 1 in accordance with the present technology.

FIG. 12 is a schematic of the study design for comparing cytisinicline (cytisine) and Chantix® in accordance with the present technology.

DETAILED DESCRIPTION

Figure 2:
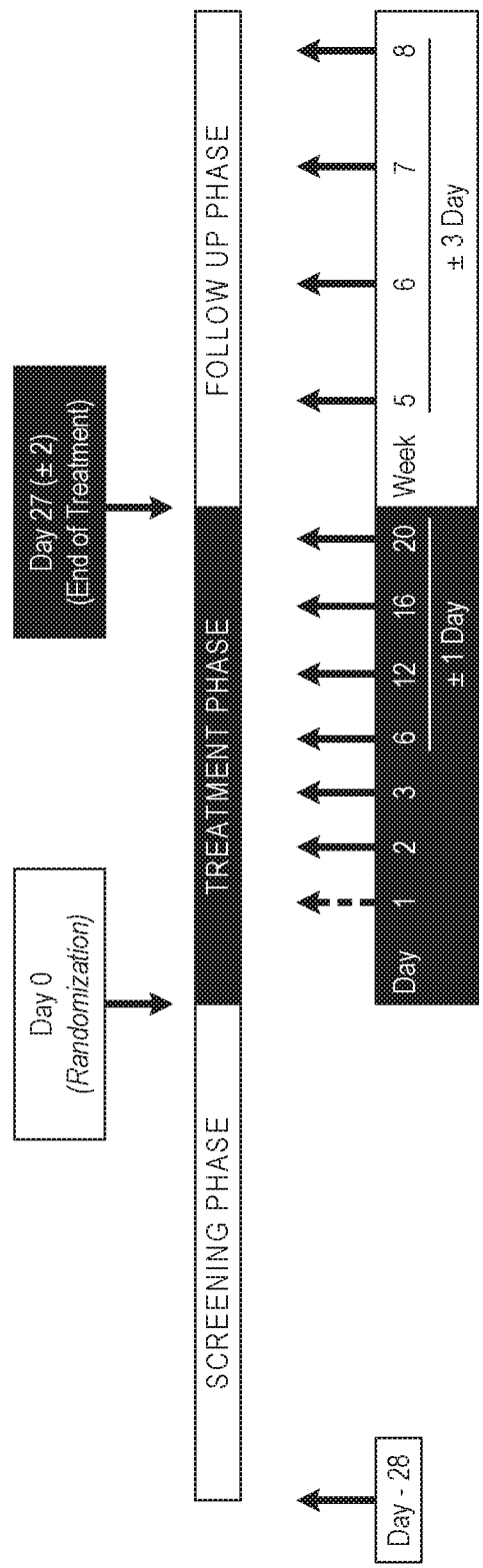
FIG. 2 is a schematic of the study design of Example 1 in accordance with the present technology.

While the present disclosure is capable of being embodied in various forms, the description below of several embodiments is made with the understanding that the present disclosure is to be considered as an exemplification of the invention and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

Also, the disclosure of ranges is intended as a continuous range, including every value between the minimum and maximum values recited, as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances, such ratios, ranges, and ranges of ratios represent various embodiments of the present disclosure.

The phrase "statistical significance," as used herein refers to a result from data generated by testing or experimentation, is not likely to occur randomly or by chance, but is instead likely to be attributable to a specific cause. Statistical significance is evaluated from a calculated probability (p-value), where the p-value is a function of the means and standard deviations of the data samples and indicates the probability under which a statistical result occurred by chance or by sampling error. A result is considered statistically significant if the p-value is 0.05 or less, corresponding to a confidence level of 95%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The phrase "control subject," as used herein refers to any subject used as a basis for comparison to the test subject. A control subject includes, but is not limited to, any subject who has not been administered the composition, administered a composition other than the test composition (e.g., 1.5 mg of cytisine three times per day or 3.0 mg of cytisine three times per day), or administered a placebo.

The term "treatment" in relation to a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

"Vaping" refers to the act of a subject inhaling vapor created by a device from a solution carried in a cartridge or a chamber. In some embodiments, the device is electronic and simulates smoking. Vaping devices can include, but are not limited, to a power source, an atomizer, and the cartridge or chamber. In some embodiments, vaping refers to consumption of ejuice or vaping activity, such as taking or otherwise consuming puffs of vapor from the vaping device, performing a vaping session with the vaping device, or otherwise using the vaping device to ingest vapor. In another embodiment, vaping refers to consumption of ejuice. In an alternative embodiment, vaping refers to consumption of ejuice or taking or otherwise consuming puffs of vapor from the vaping device. In yet another embodiment, vaping refers to vaping activity. In other embodiments, vaping refers to taking or otherwise consuming puffs of vapor from the vaping device, performing a vaping session with the vaping device, or otherwise using the vaping device to ingest vapor. In further embodiments, vaping refers to taking or otherwise consuming puffs of vapor from the vaping device or otherwise using the vaping device to ingest vapor. In still further embodiments, vaping refers to using the vaping device to ingest vapor.

As used herein, the terms "reduction in vaping," "reduced vaping," and "reduces vaping" refers to decreasing a frequency or amount of vaping per hour, per day, per week, per month, or per year, such as reducing an amount of ejuice consumed, a reduction in a number or a frequency of puffs of vapor taken or otherwise consumed from the vaping device, a reduction in a number or a frequency of vaping session performed with the vaping device, or a reduction in use of the vaping device to ingest vapor.

As used herein, the term "adverse event" (AE) refers to any untoward medical occurrence in a subject administered a composition and which does not necessarily have attribution with the treatment. An AE can therefore be any unfavorable and unintended sign (including an abnormal laboratory finding), symptom, or disease temporally associated with the use of the composition, whether or not considered related to the composition.

As used herein, the term "adverse drug reaction" refers to any untoward and unintended responses to the administered composition. The term "response to the composition" means that attribution has at least a reasonable possibility (i.e., the relationship cannot be ruled out and is judged by the investigator as at least possible) (see definition below).

The terms "serious adverse event" (SAE) and "serious adverse reaction" (SAR) refer to an AE that results in at least one of the following AEs: death, life-threatening, requires hospitalization or prolongs a subject's existing hospitalization, results in persistent or significant disability or incapacity, results in a congenital abnormality or birth defect, or is an important medical event which requires medical intervention to prevent any of the foregoing outcomes.

As used herein, the term "suspected unexpected serious adverse reactions" (SUSARs) are AEs which are serious, unexpected, and there is at least a reasonable possibility that there is attribution between the event and the composition. Important medical events are those which may not be immediately life-threatening but may jeopardize the subject and may require intervention to prevent one of the other serious outcomes listed above. Examples of such events are intensive treatment in an emergency room or at home for allergic bronchospasm, or blood dyscrasias or convulsions that do not result in hospitalization. The term "life-threatening" refers to an event in which the subject was at risk of death at the time of the event; it does not refer to an event which hypothetically might have caused death if it were more severe. For example, drug-induced hepatitis that resolves without evidence of hepatic failure would not be considered life threatening even though drug-induced hepatitis can be fatal. Inpatient hospitalization or prolongation of existing hospitalization means that hospital inpatient admission and/or prolongation of hospital stay were required for treatment of AE or occurred as a consequence of the event. It does not refer to pre-planned elective hospital admission for treatment of a pre-existing condition that has not significantly worsened, or to diagnostic procedures.

The terms "cytisine-treated arm," "active arms," "treatment arm," "active treatment arm," and "investigational arm" are used interchangeably throughout and refer to subjects administered a composition comprising cytisine.

List of abbreviations: ADR, Adverse Drug Reaction; AE, Adverse Event; ALT, Alanine Aminotransferase; AST, Aspartate Aminotransferase; BMI, Body Mass Index; Cmax, Maximum Observed Plasma Concentration; CrCl, Creatinine Clearance; CRF, Case Report Form; DSM, Data Safety Monitor; ECG, Electrocardiogram; GCP, Good Clinical Practice; ICH, International Conference on Harmonization; IMP, Investigational Medicinal Product (for this protocol, indicates cytisinicline 3.0 mg film coated tablet); MedDRA, Medical Dictionary for Regulatory Activities; SAE, Serious Adverse Event; SAR, Serious Adverse Reaction; SmPC, Summary of Product Characteristics; SOC, MedDRA System Organ Class; SUSAR, Suspected Unexpected Serious Adverse Reaction; Tmax, Time to Maximum Observed Concentration; UADR, Unexpected Adverse Drug Reaction; UAE, Unexpected Adverse Event; ULN, Upper Limit of Normal.

Compositions

A composition for use in methods of the disclosure comprises cytisine or a pharmaceutically acceptable derivative, conjugate, or salt thereof, or mixtures of any of the foregoing, collectively referred to herein as "cytisine." The term "pharmaceutically acceptable" in the present context means that the substance in question does not produce unacceptable toxicity to the subject or interaction with other components of the composition. Cytisine, (−)-cytisine, and cytisinicline are referenced interchangeably.

Any suitable cytisine pharmaceutical composition or formulation can be used in the methods described herein. In some embodiments, cytisine can be formulated in tablet form, for example, as compressed film-coated tablets for oral administration.

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e., 1 to about 10, 1 to 8, 1 to 6, 1 to 4, 1 to 3, or 1 to 2) of times per day, or as many times as needed to elicit a therapeutic response.

The unit dose can comprise a single tablet, such as a tablet containing 3.0 mg of cytisine, or it can comprise two or more tablets which together contain the unit dose (e.g., 3.0 mg of cytisine). For example, the unit dose of 3.0 mg can comprise two tablets, each containing 1.5 mg of cytisine, such as two Tabex® tablets. Each Tabex® tablet is typically formulated as a compressed film-coated tablet containing 1.5 mg of cytisine in a single tablet together with a number of tablet-forming excipients (calcium sulfate, cellulose powder, colloidal silica, magnesium stearate) and coated with a colored film-coat, including polyvinyl alcohol, titanium dioxide, and iron oxides. As another example, the unit dose of 3.0 mg can comprise three tablets, each containing 1.0 mg of cytisine, such as three tablets formulated at least similarly to the Tabex® tablets.

Alternatively, the cytisine may be formulated in a capsule or another vehicle for oral administration and are orally deliverable; or in a composition for nasal or topical administration. The terms "orally deliverable" or "oral administration" herein include any form of delivery of a therapeutic agent or a composition thereof to a subject wherein the agent or composition is placed in the mouth of the subject, whether or not the agent or composition is swallowed. Thus, "oral administration" includes buccal and sublingual, as well as esophageal administration.

The tablets and other dosage forms (hereinafter all referred to as "compositions") can contain one or more excipients, such as those common in the art. Excipients that can be employed in the compositions include, for example, fillers, disintegrants, preserving agents, lubricants, and wetting agents.

Examples of fillers that can be used include lactose (for example, either anhydrous or monohydrate), cellulose, starch (for example, corn and/or wheat starch), calcium phosphates, calcium sulfates, and mannitol.

Preserving agents prevent bacterial or fungal contamination of the formulation and include various antibacterial and antifungal agents, such as parabens, chlorobutanol, phenol, and sorbic acid.

Suitable lubricants include stearic acid and its salts. One example of a lubricant for use in the compositions of the disclosure is magnesium stearate.

The pharmaceutical compositions can further comprise sweetening, flavoring, or coloring agents.

In some embodiments, the placebo is a tablet which comprises the same, substantially the same, similar, or substantially similar non-active (e.g., cytisine) components to the test composition. In these embodiments, the placebo comprises at least the same, substantially the same, similar, or substantially similar excipients, fillers, preserving agents, lubricants, sweetening, flavoring, and/or coloring agents as the test composition, as well as at least one other non-active component, such as cellulose. In some embodiments, the placebo tablet and the test composition tablet are the same or substantially the same weight, size, shape, color, and/or are contained in the same or substantially the same packaging.

A person skilled in the art will be well aware of suitable fillers, preserving agents, and lubricants other than those specifically mentioned above, as well as suitable sweetening, flavoring, and coloring agents, and other additives. The pharmaceutical compositions of cytisine useful in the methods of the disclosure can comprise a coating, for example, a film coating, and can be coated according to any method known in the art, for example, using collidone, shellac, gum arabic, talc, titanium dioxide, or sugar.

The pharmaceutical compositions comprising cytisine can be prepared by any suitable method. For example, capsules can be prepared by mixing cytisine with one or more inert carriers such as lactose or sorbitol and packing into gelatin capsules. Tablets can be made by known compression methods.

In one embodiment, compositions of the disclosure, upon storage in a closed container maintained at room temperature, refrigerated (e.g., about 5° C. to about −10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

Methods

The disclosure provides treating a nicotine addiction or a nicotine dependence in a subject in need thereof, comprising administering the subject an effective amount of cytisine. In some embodiments, the methods of treating a nicotine addiction or a nicotine dependence include preventing smoking relapse and/or promoting cessation of or reduction in smoking in the subject in need thereof.

In some embodiments, the disclosure provides methods of treating nicotine addiction or a nicotine dependence in a subject in need thereof, comprising administering to the subject a therapeutically effective amount of cytisine. In some embodiments, present disclosure relates to methods for preventing smoking relapse in a subject in need thereof, comprising administering to the subject a therapeutically effective amount of cytisine. In another embodiment, the disclosure provides methods of promoting cessation of smoking in a subject in need thereof, comprising administering to the subject a therapeutically effective amount of cytisine. In some embodiments, the disclosure provides methods for promoting a reduction in smoking of a subject in need thereof, comprising administering to the subject an effective amount of cytisine. In some embodiments, the disclosure provides methods of treating nicotine addiction or a nicotine dependence in a subject in need thereof, wherein the nicotine addiction or a nicotine dependence is in the form of cigarettes, smokeless tobacco, snus, electronic cigarettes (e-cigs), vapes such as vaping using a vaping device, and/or hookah. In some embodiments, the vaping device includes a liquid comprising nicotine, for example, about 1 mg/ml nicotine to about 12 mg/ml nicotine or greater than about 13 mg/ml nicotine. Any patient with nicotine addiction or a nicotine dependence can be treated by the methods disclosed herein.

In additional embodiments, the disclosure provides methods of treating and/or preventing an addiction or a dependence in a subject in need thereof, comprising administering to the subject a therapeutically effective amount of cytisine. Without intending to be bound by any particular theory, it is thought that cytisine interacts with the dopamine neurotransmitter release cycle as a partial agonist of nicotinic acetylcholine receptors (nAChRs) and is useful for treating and/or preventing a plurality of addictions or plurality of dependences in a subject in need thereof. Non-limiting examples of addictions and dependencies that are thought to be treated and/or prevented by administration of cytisine includes addictions and/or dependencies to substances, compounds, and/or behaviors that may involve the dopamine neurotransmitter release cycle. Exemplary substances, compounds, and/or behaviors includes, but is not limited to, marijuana, cannabis, tetrahydrocannabinol (THC), cannabidiol (CBD), alcohol, opioids and other painkillers, cocaine, eating, gambling, sex, heroin, benzodiazepines, barbiturates, stimulants, and inhalants. In further embodiments, the disclosure provides methods of promoting cessation of the addiction or the dependence in a subject in need thereof, comprising administering to the subject a therapeutically effective amount of cytisine. In some embodiments, the disclosure provides methods for promoting a reduction in a subject's addiction and/or dependence, comprising administering to the subject an effective amount of cytisine. The compositions and methods described herein with respect to smoking, vaping, and nicotine can be used to treat, prevent, and/or reduce addiction or dependence in the subject in need thereof, such as any subject having an addiction or a dependence involving the dopamine neurotransmitter release cycle.

In further embodiments, the methods of treating a nicotine addiction or a nicotine dependence include preventing vaping relapse and/or promoting cessation of or reduction in vaping in the subject in need thereof. In some embodiments, the present disclosure relates to methods for preventing vaping relapse in a subject in need thereof, comprising administering to the subject a therapeutically effective amount of cytisine. In another embodiment, the disclosure provides methods of promoting cessation of vaping in a subject in need thereof, comprising administering to the subject a therapeutically effective amount of cytisine. In some embodiments, the disclosure provides methods for promoting a reduction in vaping of a subject in need thereof, comprising administering to the subject a therapeutically effective amount of cytisine.

In some embodiments, provided herein is a method of treating of nicotine addiction or a nicotine dependence in a subject, comprising administering cytisine in equal dosage amounts two times per day ("bid" or "BID") or three times per day ("tid" or "TID") to a subject in need thereof. In one embodiment, each of the two daily administrations occur morning and evening, respectively. In another embodiment, each of the two daily administrations occur in approximate intervals of 10-12 hours. In yet another embodiment, each of the three daily administrations occur morning, noon, and evening, respectively. In another embodiment, each of the three daily administrations occur in approximate intervals of 4-5 hours. In yet another embodiment, each of the three daily administrations occur in approximate intervals of 4 hours, 5 hours, 6 hours, 7 hours, 8 hours, 9 hours, 10 hours, or more. In one embodiment, the administration occurs for a period of at least about 6 weeks, at least about 12 weeks, at least about 24 weeks, or indefinitely. In this embodiment, the administration can include BID or TID for any period of days or weeks during the administration. For example, in these embodiments, the entire period of administration can be BID or TID. As another example, in these embodiments, at least a portion of the administration can be BID or TID, such as at least about one day, at least about three days, at least about one week, at least about two weeks, at least about four weeks, at least about 12 weeks. As yet another example, in these embodiments, the BID or TID administration can occur in any order, such as Day 1 can be BID or TID, Day 2 can be BID or TID, Day 3 can be BID or TID, and so on for the period of administration.

In some embodiments, the administration occurs independent of whether the subject is in a fed or fasted state. For example, the administration can occur simultaneously with food, concurrently with food, any amount of time before the subject ingests food, or any amount of time after the subject ingests food. Without intending to be limited to any particular theory, it is not thought that food (or a fed state or a fasted state) impacts the bioavailability of cytisine which can be determined by an overall body absorption or overall bioavailability of cytisine in the subject.

In some embodiments, the TID dose is 1 mg, 1.5 mg, 2 mg, 2.5 mg, or 3.0 mg of cytisine. In some embodiments, the TID dose is 1 mg, regardless of how the dose is divided. For example, each TID dose could be given in two 0.5 mg strength tablets administered 3 times per day or in one 1 mg tablet administered three times per day, or any other possibility. In some embodiments, the TID dose is 1.0 mg, regardless of how the dose is divided among dosage units. In some embodiments, the TID dose is 1.5 mg, regardless of how the dose is divided among dosage units. In some embodiments, the TID dose is 2 mg, regardless of how the dose is divided among dosage units. In yet another embodiment, the TID dose is 2.5 mg, regardless of how the dose is divided among dosage units. In some embodiments, the TID dose is 3.0 mg, regardless of how the dose is divided among dosage units.

In some embodiments, the subject experiences no adverse events related to the cytisine treatment. Adverse events can be mild (e.g, no interference with activity), moderate (some interference with activity but requiring no or minimal medical intervention), or severe (prevents daily activity and requires medical intervention). Non-limiting examples of adverse events include an upper respiratory tract infection (URTI), abnormal dreams, nausea, insomnia, headache, fatigue, and constipation. In other embodiments, the subject experiences two or fewer adverse events related to the cytisine treatment, such as, an increase in the occurrence of nausea, abnormal dreams, insomnia, headache, and/or URTI in a subject from about 0% to about 10%, for example, about 0%, about 1%, about 2%, about 3%, about 4%, about 5%, about 6%, about 7%, about 8%, about 9%, or about 10%. In some embodiments, the subject experiences no adverse events as compared to a subject administered a nicotine replacement therapy (NRT), bupropion, varenicline, electronic cigarettes, vaping, and/or combination thereof.

In some embodiments, the subject experiences nicotine addiction or a nicotine dependence by smoking cigarettes, ingesting smokeless tobacco and/or snus, using electronic cigarettes (e-cigs) and/or vapes, and/or using hookah daily, such as a per unit consumption of nicotine per day. In some embodiments, the subject having nicotine addiction or a nicotine dependence consumes about 0 to about 100 units of nicotine per day. For example, a single cigarette may be a unit of nicotine and the subject having the nicotine addiction or a nicotine dependence smokes about 0 cigarettes per day to about 100 cigarettes per day, about 5 cigarettes per day to about 75 cigarettes per day, about 5 cigarettes per day to about 50 cigarettes per day, about 5 cigarettes per day to about 25 cigarettes per day, about 10 cigarettes per day to about 50 cigarettes per day, about 20 cigarettes per day to about 50 cigarettes per day, about 25 cigarettes per day to about 75 cigarettes per day, about 25 cigarettes per day to about 50 cigarettes per day, for example, about 0 cigarettes per day, about 1 cigarette per day, about 2 cigarettes per day, about 3 cigarettes per day, about 4 cigarettes per day, about 5 cigarettes per day, about 6 cigarettes per day, about 7 cigarettes per day, about 8 cigarettes per day, about 9 cigarettes per day, about 10 cigarettes per day, about 11 cigarettes per day, about 12 cigarettes per day, about 13 cigarettes per day, about 14 cigarettes per day, about 15 cigarettes per day, about 16 cigarettes per day, about 17 cigarettes per day, about 18 cigarettes per day, about 19 cigarettes per day, about 20 cigarettes per day, about 25 cigarettes per day, about 30 cigarettes per day, about 35 cigarettes per day, about 40 cigarettes per day, about 45 cigarettes per day, about 50 cigarettes per day, about 55 cigarettes per day, about 60 cigarettes per day, about 65 cigarettes per day, about 70 cigarettes per day, about 75 cigarettes per day, about 80 cigarettes per day, about 85 cigarettes per day, about 90 cigarettes per day, or about 100 cigarettes per day. In other examples, units of nicotine also include ingesting smokeless tobacco and/or snus, using electronic cigarettes (e-cigs) and/or vapes (e.g., vaping), and/or using hookah instead of or in combination with cigarettes daily.

In some embodiments, administration of cytisine reduces the number of units of nicotine a subject ingests per day, such as a number of cigarettes a subject smokes per day. In some embodiments, the methods of the present technology reduce a percentage of cigarettes smoked by the subject by at least about 60%, at least about 65%, at least about 70%, at least about 75%, at least about 80%, at least about 85%, at least about 90%, at least about 95%, or at least about 100% as compared to a control subject, placebo control, and/or baseline after treatment with 1.0 mg TID, 1.5 mg TID, or 3.0 mg TID of cytisine.

In some embodiments, the administration of cytisine increases abstinence in the subject after treatment with 1.0 mg TID, 1.5 mg TID, or 3.0 mg TID of cytisine. In these embodiments, the subject has increased abstinence of about 5% to about 30%, for example, about 5% to about 15%, about 5% to about 10%, about 5% to about <10%, about 10% to about 25%, about 15% to about 20%, about 20% to about 30%, or about 25% to about <30%, about 5% to about 100%, about 5% to about 75%, about 5% to about 50%, about 25% to about 75%, about 25% to about 50%, about 30% to about 50%, about 30% to about 50%, about 30% to about 75%, about 30% to about <100%, or about 30% to about 100%, such as at least about 10%, at least about 15%, at least about 20%, at least about 25%, at least about 30%, at least about 35%, at least about 40%, at least about 45%, at least about 50%, or at least about 55% following cytisine treatment relative to an abstinence achieved without cytisine treatment. In some embodiments, abstinence is a period of abstinence, such as about a 2 week abstinence, about a 3 week abstinence, about a 4 week abstinence, about a 5 week abstinence, about a 6 week abstinence, about a 7 week abstinence, about an 8 week abstinence, about a 12 week abstinence, about a 16 week abstinence, about a 20 week abstinence, about a 24 week abstinence, about a 28 week abstinence, or about a 32 week abstinence. In certain embodiments, the period of abstinence is about 1 day to about 4 weeks, from about 1 week to about 8 weeks, from about 2 weeks to about 12 weeks, from about 4 weeks to about 24 weeks, or from about 8 weeks to about 32 weeks.

In some embodiments, administration of cytisine increases a quit rate in the subject after treatment with 1.0 mg TID, 1.5 mg TID, or 3.0 mg TID of cytisine. In these embodiments, the subject has a quit rate of about 5% to about 30%, for example, about 5% to about 15%, about 5% to about 10%, about 5% to about <10%, about 10% to about 25%, about 15% to about 20%, about 20% to about 30%, or about 25% to about <30%, about 5% to about 100%, about 5% to about 75%, about 5% to about 50%, about 25% to about 75%, about 25% to about 50%, about 30% to about 50%, about 30% to about 50%, about 30% to about 75%, about 30% to about <100%, or about 30% to about 100%, such as at least about 10%, at least about 15%, at least about 20%, at least about 25%, at least about 30%, at least about 35%, at least about 40%, at least about 45%, at least about 50%, or at least about 55% after a 4 week abstinence or during continuous abstinence during weeks 5-8 following cytisine treatment. In some embodiments, quit rate is determined after a period of abstinence, such as about a 1 day abstinence, about a 3 day abstinence, about a 7 day abstinence, about a 10 day abstinence, about a 2 week abstinence, about a 3 week abstinence, about a 4 week abstinence, about a 5 week abstinence, about a 6 week abstinence, about a 7 week abstinence, about an 8 week abstinence, about a 9 week abstinence, about a 10 week abstinence, about an 11 week abstinence, about a 12 week abstinence, about a 16 week abstinence, about a 20 week abstinence, about a 24 week abstinence, about a 28 week abstinence, or about a 32 week abstinence. In certain embodiments, the period of abstinence is about 1 day to about 4 weeks, from about 1 week to about 8 weeks, from about 1 week to about 2 weeks, from about 3 weeks to about 6 weeks, from about 2 weeks to about 12 weeks, from about 9 weeks to about 12 weeks, from about 4 weeks to about 24 weeks, or from about 8 weeks to about 32 weeks.

In some embodiments, the subject has expired CO levels of about 0 ppm to about 50 ppm, for example, about 10 ppm to about 40 ppm, about 10 ppm to about 30 ppm, about 10 ppm to about <20 ppm, about 20 ppm to about 30 ppm, about 20 ppm to about 40 ppm, about 20 ppm to about <50 ppm, or about 20 ppm to about 50 ppm, for example, about 0 ppm, about 2 ppm, about 4 ppm, about 6 ppm, about 8 ppm, about 10 ppm, about 12 ppm, about 14 ppm, about 16 ppm, about 18 ppm, about 20 ppm, about 22 ppm, about 24 ppm, about 26 ppm, about 28 ppm, about 30 ppm, about 32 ppm, about 34 ppm, about 36 ppm, about 38 ppm, about 40 ppm, about 42 ppm, about 44 ppm, about 46 ppm, about 48 ppm, or about 50 ppm before treatment with cytisine. In some embodiments, administration of 1.0 mg TID, 1.5 mg TID, or 3.0 mg TID of cytisine, or treatment with 1.0 mg TID, 1.5 mg TID, or 3.0 mg TID of cytisine, reduces a level of expired CO by the subject by at least about 60%, at least about 65%, at least about 70%, at least about 75%, at least about 80%, at least about 85%, at least about 90%, at least about 95%, or at least about 100% as compared to a control subject, placebo control, and/or baseline. In some embodiments, the subject has expired CO levels of about 0 ppm to about 30 ppm, for example, about 10 ppm to about 25 ppm, about 10 ppm to about 20 ppm, about 10 ppm to about <20 ppm, about 5 ppm to about 15 ppm, about 5 ppm to about 10 ppm, about 1 ppm to about <10 ppm, or about 10 ppm to about 5 ppm, for example about 0 ppm, about 2 ppm, about 4 ppm, about 6 ppm, about 8 ppm, about 10 ppm, about 12 ppm, about 14 ppm, about 16 ppm, about 18 ppm, or about 20 ppm after treatment with cytisine.

In some embodiments, the subject has serum and/or plasma cotinine levels of about 5 ng/mL to about 500 ng/mL, about 25 ng/mL to about 400 ng/mL, about 25 ng/mL to about 400 ng/mL, about 25 ng/mL to about 300 ng/mL, about 50 ng/mL to about 200 ng/mL, about 75 ng/mL to about 150 ng/mL, about 85 ng/mL to about 100 ng/mL, about 100 ng/mL to about 400 ng/mL, about 100 ng/mL to about 300 ng/mL, about 100 ng/mL to about 200 ng/mL, about 200 ng/mL to about 300 ng/mL, about 200 ng/mL to about 400 ng/mL, about 200 ng/mL to about <500 ng/mL, about 200 ng/mL to about 500 ng/mL, for example, about 10 ng/mL, about 20 ng/mL, about 30 ng/mL, about 40 ng/mL, about 50 ng/mL, about 60 ng/mL, about 70 ng/mL, about 80 ng/mL, about 90 ng/mL, about 100 ng/mL, about 125 ng/mL, about 150 ng/mL, about 175 ng/mL, about 200 ng/mL, about 225 ng/mL, about 250 ng/mL, about 275 ng/mL, about 300 ng/mL, about 325 ng/mL, about 350 ng/mL, about 375 ng/mL, about 400 ng/mL, about 425 ng/mL, about 450 ng/mL, about 475 ng/mL, or about 500 ng/mL before treatment with cytisine. In some embodiments, administration of 1.0 mg TID, 1.5 mg TID, or 3.0 mg TID of cytisine, or treatment with 1.0 mg TID, 1.5 mg TID, or 3.0 mg TID of cytisine, reduces serum and/or plasma cotinine levels in the subject by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% as compared to a control subject, placebo control, and/or baseline. In some embodiments, the subject has serum and/or plasma cotinine levels of about 0.1 ng/mL to about 20 ng/mL, about 0.1 ng/mL to about 15 ng/mL, about 0.5 ng/mL to about 10 ng/mL, about 1 ng/mL to about 10 ng/mL, about 0.5 ng/mL to about 5 ng/mL, or about 0.5 ng/mL to about 1 ng/mL, for example, about 0.1 ng/mL, about 0.5 ng/mL, about 1 ng/mL, about 1.5 ng/mL, about 3 ng/mL, about 5 ng/mL, about 7 ng/mL, about 8 ng/mL, about 9 ng/mL, about 10 ng/mL, about 15 ng/mL, or about 20 ng/mL after treatment with cytisine.

In some embodiments, administration of cytisine increases an odds ratio in the subject after treatment with 1.0 mg TID, 1.5 mg TID, or 3.0 mg TID of cytisine for 4 weeks of treatment, after 8 weeks of treatment, and 4 weeks after treatment ends. In these embodiments, the subject has an odds ratio of about 1.1 to about 20, about 1.1 to about 15, about 1.1 to about 10, about 1.1 to about 5, about 5 to about 10, about 5 to about 15, about 10 to about 15, about 10 to about <20, or about 10 to about 20 as compared to a control subject, placebo control, and/or baseline.

In some embodiments, the subject's vital signs, hematology and chemistry levels, and ECG are measured prior to and/or after administration of cytisine. In some embodiments, the subject exhibits no clinically-significant changes in vital signs, hematology and chemistry levels, and ECG after administration of cytisine.

In some embodiments, the subject is a heavy, moderate, or light nicotine user, such as a smoker or a vaper using nicotine can be categorized as a "heavy smoker" or "heavy vaper," a "moderate smoker" or "moderate vaper," or a "light smoker" or "light vaper." For example, a "heavy smoker" as provided herein refers to a subject who reports consuming 20 or more cigarettes per day. A "moderate smoker" as provided herein refers to a subject who reports consuming 11-19 cigarettes per day. A "light smoker" as provided herein refers to a subject who reports consuming 1-10 cigarettes per day. As another example, a "heavy vaper" as provided herein refers to a subject who reports performing 20 or more vaping sessions per day, consuming 20 or more puffs from a vaping device per day, or otherwise reports 20 or more uses of a vaping device per day. A "moderate vaper" as provided herein refers to a subject who reports performing 11-19 vaping sessions per day, consuming 11-19 puffs from a vaping device per day, or otherwise reports 11-19 uses of a vaping device per day. A "light vaper" as provided herein refers to a subject who reports performing 1-10 vaping sessions per day, consuming 1-10 puffs from a vaping device per day, or otherwise reports 1-10 uses of a vaping device per day. In some embodiments, administration of cytisine reduces cotinine levels in a subject identified as a heavy smoker or a heavy vaper. In some embodiments, administration of cytisine reduces cotinine levels in a subject identified as a moderate smoker or a moderate vaper. In yet another embodiment, administration of cytisine reduces cotinine levels in a subject identified as a light smoker or a light vaper.

In some embodiments, the subject has been smoking or vaping for at least about 1 year, at least about 5 years, at least about 10 years, at least about 15 years, at least about 20 years, at least about 25 years, at least about 30 years, at least about 35 years, at least about 40 years, at least about 45 years, at least about 50 years, or more, prior to administration of cytisine.

In some embodiments, the subject began smoking or vaping as an adolescent. In some embodiments, the subject began smoking cigarettes or vaping between the ages of 10 and 19. In some embodiments, the subject began smoking cigarettes or vaping as an adolescent and has been smoking cigarettes or vaping for at least about 20 years, at least about 25 years, at least about 30 years, at least about 35 years, at least about 40 years, at least about 45 years, at least about 50 years, or more prior to administration of cytisine.

In some embodiments, the length of the administration is up to about 26 weeks. In certain embodiments the length of the administration is from about 6 weeks to about 12 weeks, and in some embodiments, the cytisine is administered as described above for about 6 weeks.

Figure 7:
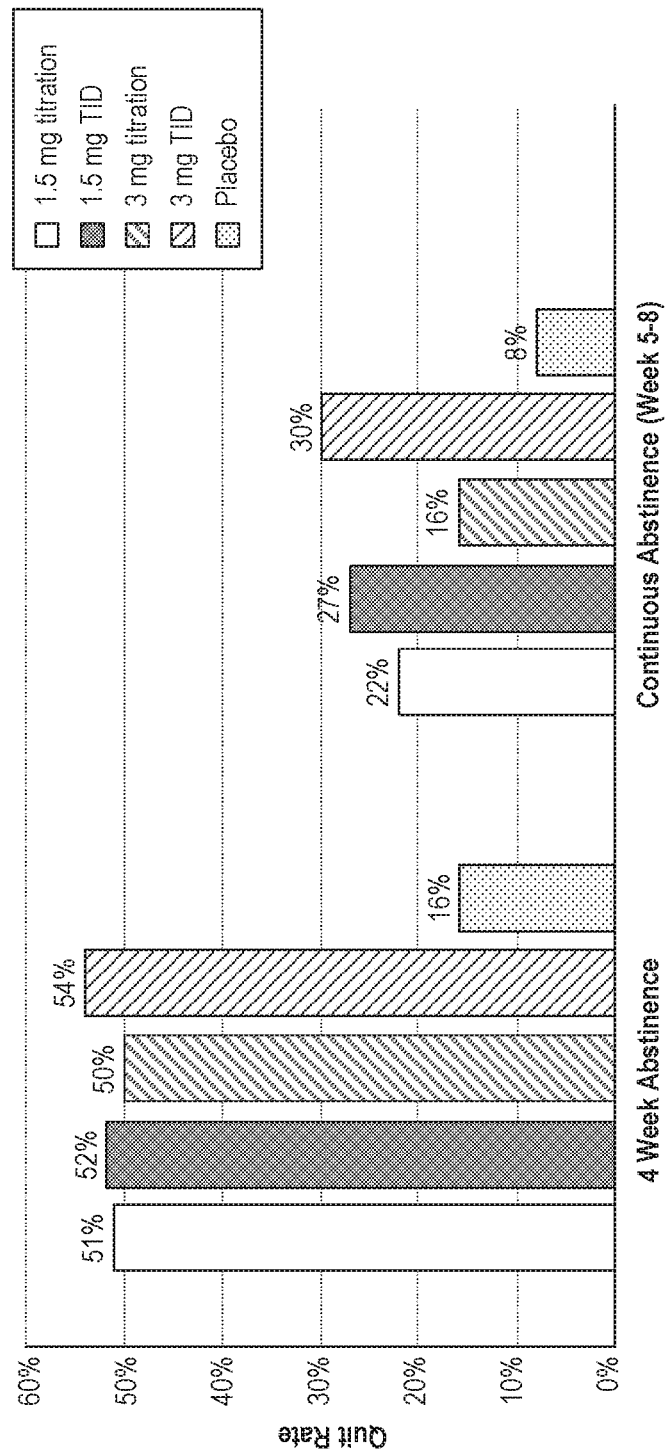
FIG. 7 is a representative graph depicting a comparison between quit rates after 4 weeks of abstinence compared to a quit rate during continuous abstinence (weeks 5-8) in the subject population of Example 1 in accordance with the present technology.

Compared with the commercial 25-day titration schedule with unit doses of 1.5 mg of cytisine, the percentage of smokers with continuous abstinence is surprisingly higher in the subjects treated according to the methods disclosed herein, as demonstrated, for example, in FIG. 7.

In some embodiments, the subject is a smoker, for example, a smoker who smokes about 3 or more cigarettes a day. In some embodiments, the subject is a smoker who smokes about 5 or more or about 10 or more cigarettes a day. In some embodiments, the subject has measurable expired air CO concentration of about 10 ppm or greater prior to the administration of cytisine.

In some embodiments, the subject is a refractory patient. As used herein, a "refractory patient" or "refractory subject" is a subject who has failed treatment with one or more nicotine addiction or nicotine dependence treatments. In some embodiments, nicotine addiction or nicotine dependence treatments include both the regulatory agency-approved treatments and smoking cessation methods, such as vaping and behavioral support. Non-limiting examples of behavioral support include behavioral support useful for reducing, preventing, or otherwise treating anxiety, depression, and/or withdrawal symptoms. In certain embodiments, behavioral support includes counseling, diaries, wearable devices, apps, web-based smoking cessation programs, texting interventions, and combinations thereof. In further embodiments, behavioral support is provided to non-refractory patients, such as control patients (e.g., baseline, administered a placebo, administered a smoking, vaping, or nicotine cessation medication that does not include cytisinicline). In some embodiments, the nicotine addiction or nicotine dependence treatments include FDA-approved, first-line smoking cessation medications such as NRT, bupropion, and varenicline. Nicotine replacement therapy can be in the form of patch, gum, lozenge, spray, and inhaler.

In some embodiments, the subject is a refractory patient who has failed treatment with one or more nicotine addiction or nicotine dependence treatments. For example, the subject has failed two or more treatments, three or more treatments, four or more treatments, five or more treatments, six or more treatments, seven or more treatments, eight or more treatments, nine or more treatments, or ten or more treatments. In some embodiments, the subject is a refractory patient who has failed nicotine addiction or nicotine dependence treatments comprising NRT, administration of bupropion, administration of varenicline, electronic cigarettes, vaping, or a combination thereof.

In some embodiments, the subject has previously attempted to quit smoking or vaping at least 1 time, at least 2 times, at least 3 times, at least 4 times, at least 5 times, at least 6 times, at least 7 times, at least 8 times, at least 9 times, at least 10 times, or more prior to administration of cytisine.

In some embodiments, the refractory subject has previously received nicotine addiction and/or nicotine dependence treatment for at least about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks prior to administration of cytisine.

In one aspect, the methods comprise administering cytisine to the subject, wherein the cytisine is provided in a unit dose of about 1.0 mg to about 5.0 mg. In certain embodiments, the unit dose of cytisine is about 1.0 mg. In certain embodiments, the unit dose of cytisine is about 1.5 mg. In certain embodiments, the unit dose of cytisine is about 3.0 mg. In some embodiments, the unit dose of cytisine is administered to the subject three to six times daily. In some embodiments, the unit dose of cytisine is administered to the subject three times per day. In some embodiments of the methods disclosed herein, the unit dose is either about 1.0 mg administered three times daily, about 1.5 mg administered three times daily, or about 3.0 mg administered three times daily for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 4 months, about 1 year, about 1.25 years, about 1.5 years, about 1.75 years, about 2 years, or more than about 2 years. In certain embodiments, the unit dose of cytisine is administered for up to about 2 weeks, for about 2 weeks to about 6 weeks, for about 3 weeks to about 6 weeks, or for about 9 weeks to about 12 weeks. In some embodiments, a relapse rate is lower for subjects administered the unit dose of cytisine for at least about 4 weeks compared to subjects administered the unit dose of cytisine for at least about 2 weeks. In other embodiments, a relapse rate is lower for subjects administered the unit dose of cytisine for at least about 6 weeks compared to subjects administered the unit dose of cytisine for at least about 4 weeks. In further embodiments, a relapse rate is lower for subjects administered the unit dose of cytisine for at least about 8 weeks compared to subjects administered the unit dose of cytisine for at least about 4 weeks. In still further embodiments, a relapse rate is lower for subjects administered the unit dose of cytisine for at least about 12 weeks compared to subjects administered the unit dose of cytisine for at least about 4 weeks.

In some embodiments, administration of cytisine to the subject resulted in a significantly better nicotine use cessation rate (smoking cessation rate or vaping succession rate), as compared to a subject administered the commercial 1.5 mg per unit dose titration schedule. In some embodiments, the unit dose of 3.0 mg of cytisine is administered three times daily for 6 weeks (e.g., the first 6 weeks) followed by placebo for 6 weeks (e.g., the second six weeks). In certain embodiments, behavioral support is provided to the subject during at least a portion of the first 6 weeks, during at least a portion of the second 6 weeks, before at least a portion of the first 6 weeks, after at least a portion of the second 6 weeks, or during a combination thereof. In some embodiments, the unit dose of 3.0 mg of cytisine is administered three times daily for 12 weeks. In certain embodiments, behavioral support is provided to the subject during at least a portion of the 12 weeks, before the 12 weeks, after the 12 weeks, or a combination thereof. Thereafter, in some embodiments the subject exhibits one or more of:

(a) a reduction in units of nicotine used per day, such as cigarettes smoked per day or vaping per day, as compared to a subject who has been administered an NRT, a control subject, placebo control, and/or baseline;

(b) a reduction in expired CO levels as compared to a subject who has been administered an NRT, a control subject, placebo control, and/or baseline;

(c) a reduction in the subject's serum and/or plasma cotinine levels compared to a subject who has been administered an NRT, a control subject, placebo control, and/or baseline;

(d) an increase in quit rate as compared to a subject who has been administered an NRT, a control subject, placebo control, and/or baseline;

(e) no change, no increase, or a decrease in adverse events compared to a subject who has been administered an NRT, a control subject, placebo control, and/or baseline;

(f) an increase in the subject's odds ratio as compared to a subject who has been administered an NRT, a control subject, placebo control, and/or baseline;

(g) an increase in abstinence compared to a subject who has been administered an NRT, a control subject, placebo control, and/or baseline;

(h) a reduction in nicotine cravings and/or tobacco cravings compared to a subject who has been administered an NRT, a control subject, placebo control, and/or baseline;

(i) a reduction of the severity of nicotine withdrawal symptoms compared to a subject who has been administered an NRT, a control subject, placebo control, and/or baseline;

(j) a reduction of the severity of anxiety compared to a subject who has been administered an NRT, a control subject, placebo control, and/or baseline; and/or (k) a reduction of the severity of depression compared to a subject who has been administered an NRT, a control subject, placebo control, and/or baseline.

In one embodiment, methods of the present disclosure comprise measuring baseline levels of one or more markers set forth in (a)-(k) above prior to dosing the subject or subject group. In another embodiment, the methods comprise administering a composition as disclosed herein to the subject after baseline levels of one or more markers set forth in (a)-(k) are determined, and subsequently taking an additional measurement of said one or more markers. In another embodiment, upon treatment with a composition of the present disclosure, the subject exhibits one or more of:

(a) a reduction in units of nicotine used per day, such as cigarettes smoked per day or vaping per day by at least about 10%, at least about 20%, at least about 30%, at least about 40%, at least about 50%, or more, compared to a subject who has been administered an NRT, a control subject, placebo control, and/or baseline;

(b) a reduction in expired CO levels of about 5% to about 100% compared to baseline, control, or placebo levels, for example about 5%, about 10%, about 15%, about 20%, about 25%, about 30%, about 35%, about 40%, about 45%, about 50%, or more, compared to a subject who has been administered an NRT, a control subject, placebo control, and/or baseline;

(c) a reduction in serum and/or plasma cotinine levels of at least about 5%, at least about 10%, at least about 15%, at least about 20%, at least about 25%, at least about 30%, at least about 35%, at least about 40%, at least about 45%, at least about 50%, or more, as compared to a subject who has been administered an NRT, a control subject, placebo control, and/or baseline;

(d) an increase in quit rate of about 5% to about 100%, about 5% to about 75%, about 5% to about 50%, about 25% to about 75%, about 25% to about 50%, about 30% to about 50%, about 30% to about 75%, about 30% to about <100%, or about 30% to about 100%, as compared to a subject who has been administered an NRT, a control subject, placebo control, and/or baseline;

(e) no change, no increase, or a decrease in adverse events of about 0%, about 5%, about 10%, about 15%, about 20%, about 25%, about 30%, about 35%, about 40%, about 45%, about 50%, or more compared to a subject who has been administered an NRT, a control subject, placebo control, and/or baseline;

(f) an increase in the subject's odds ratio of about 0%, about 5%, about 10%, about 15%, about 20%, about 25%, about 30%, about 35%, about 40%, about 45%, about 50%, or more, compared to a subject who has been administered an NRT, a control subject, placebo control, and/or baseline;

(g) an increase in abstinence of about 0%, about 5%, about 10%, about 15%, about 20%, about 25%, about 30%, about 35%, about 40%, about 45%, about 50%, or more compared to a subject who has been administered an NRT, a control subject, placebo control, and/or baseline;

(h) a reduction in tobacco cravings of about 0%, about 5%, about 10%, about 15%, about 20%, about 25%, about 30%, about 35%, about 40%, about 45%, about 50%, or more, compared to a subject who has been administered an NRT, a control subject, placebo control, and/or baseline;

(i) a reduction of the severity of nicotine withdrawal symptoms of about 0%, about 5%, about 10%, about 15%, about 20%, about 25%, about 30%, about 35%, about 40%, about 45%, about 50%, or more, compared to a subject who has been administered an NRT, a control subject, placebo control, and/or baseline;

(j) a reduction of the severity of anxiety of about 0%, about 5%, about 10%, about 15%, about 20%, about 25%, about 30%, about 35%, about 40%, about 45%, about 50%, or more compared to a subject who has been administered an NRT, a control subject, placebo control, and/or baseline; and/or (k) a reduction of the severity of depression of about 0%, about 5%, about 10%, about 15%, about 20%, about 25%, about 30%, about 35%, about 40%, about 45%, about 50%, or more, compared to a subject who has been administered an NRT, a control subject, placebo control, and/or baseline.

In some embodiments, methods of the present disclosure include treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject. In certain embodiments, the subject experiences no adverse events after receiving the cytisine treatment. In some embodiments, the adverse event is selected from the group consisting of an URTI, abnormal dreams, nausea, insomnia, headache, fatigue, and constipation. In certain embodiments, the subject experiences no nausea after receiving the cytisine treatment. In some embodiments, cytisine is administered for about 6 weeks or for about 12 weeks. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, the subject is a refractory patient who has failed treatment with one or more nicotine addiction, nicotine dependence, or smoking cessation treatments. In some embodiments, the nicotine addiction, nicotine dependence, or smoking cessation treatments are selected from NRT, administration of bupropion, administration of varenicline, electronic cigarettes, vaping, and a combination thereof. In some embodiments, the subject (a) smoked ten or more cigarettes or used ten or more vapes per day prior to the administration of cytisine, (b) has expired air CO concentration of about 10 ppm or greater prior to the administration of cytisine, or (c) a combination of (a) and (b). In some embodiments, the methods further comprise providing behavioral support to the subject.

In some embodiments, methods of the present disclosure include treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject wherein the subject experiences no adverse events after receiving the cytisine treatment. In some embodiments, the adverse event is selected from the group consisting of an URTI, abnormal dreams, nausea, insomnia, headache, fatigue, and constipation.

In some embodiments, methods of the present disclosure include treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject wherein the subject experiences no nausea after receiving the cytisine treatment.

In some embodiments, methods of the present disclosure include treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject for about 6 weeks or for about 12 weeks. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

In some embodiments, methods of the present disclosure include treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject wherein the subject is a refractory patient who has failed treatment with one or more nicotine addiction, nicotine dependence, or smoking cessation treatments. In some embodiments, the nicotine addiction, nicotine dependence, or smoking cessation treatments are selected from NRT, administration of bupropion, administration of varenicline, electronic cigarettes, vaping, and a combination thereof.

In some embodiments, methods of the present disclosure include treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject wherein the subject (a) smoked ten or more cigarettes per day prior to the administration of cytisine, (b) has expired air CO concentration of about 10 ppm or greater prior to the administration of cytisine, or (c) a combination of (a) and (b).

In some embodiments, methods of the present disclosure include treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject, and providing behavioral support to the subject.

Methods of the present disclosure further include treatment of nicotine addiction or nicotine dependence in a subject in need thereof, the method comprising administering cytisine to the subject, wherein the subject is a refractory patient who has failed treatment with one or more nicotine addiction or nicotine dependence treatments. In certain embodiments, the nicotine addiction or nicotine dependence treatments comprise NRT, administration of bupropion, administration of varenicline, electronic cigarettes, vaping, or a combination thereof. In some embodiments, cytisine is provided in a unit dose of about 1.0 mg to about 6.0 mg of cytisine three to six times daily to a subject in need thereof. In certain embodiments, cytisine is provided in a unit dose of 3.0 mg of cytisine three times daily to a subject in need thereof. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b).

Methods of the present disclosure further provide methods of preventing smoking and/or vaping relapse in a subject in need thereof, the method comprising administering cytisine provided in a unit dose of (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, three times daily to the subject. In some embodiments, cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the subject is a refractory patient who has failed treatment with one or more smoking cessation treatments. In certain embodiments, the smoking cessation treatments comprise NRT, administration of bupropion, administration of varenicline, electronic cigarettes, vaping, or a combination thereof.

Methods of the present disclosure further include preventing smoking and/or vaping relapse in a subject in need thereof, the method comprising administering cytisine to the subject, wherein the subject is a refractory patient who has failed treatment with one or more smoking cessation treatments selected from the group consisting of NRT, administration of bupropion, administration of varenicline, electronic cigarettes, vaping, or a combination thereof. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, three times daily to the subject, and wherein cytisine is administered for about 6 weeks or for about 12 weeks. In some embodiments, the subject experiences no adverse events selected from the group consisting of an URTI, abnormal dreams, nausea, insomnia, headache, fatigue, and constipation after receiving the cytisine treatment.

The present disclosure also provides medicaments, such as, a medicament comprising a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, wherein the medicament is for three times daily oral administration to the subject. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In certain embodiments, the subject experiences no nausea after receiving the cytisine treatment. In some embodiments, cytisine is administered for about 6 weeks or for about 12 weeks. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, the subject is a refractory patient who has failed treatment with one or more nicotine addiction, nicotine dependence, or smoking cessation treatments. In certain embodiments, the nicotine addiction, nicotine dependence, or smoking cessation treatments are selected from NRT, administration of bupropion, administration of varenicline, electronic cigarettes, vaping, and a combination thereof. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the methods further comprise providing behavioral support to the subject.

The present disclosure also provides medicaments, such as, a medicament comprising a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, wherein the medicament is for three times daily oral administration to the subject, and wherein the subject experiences no adverse events after receiving the cytisine treatment. In certain embodiments, the adverse event is selected from the group consisting of an URTI, abnormal dreams, nausea, insomnia, headache, fatigue, and constipation. In certain embodiments, the subject experiences no nausea after receiving the cytisine treatment.

The present disclosure further provides medicaments, such as, a medicament comprising a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, and wherein the cytisine is administered for about 6 weeks or for about 12 weeks. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

In some embodiments, the present disclosure further provides a medicament comprising a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, and wherein the subject is a refractory patient who has failed treatment with one or more nicotine addiction or smoking cessation treatments. In certain embodiments, the nicotine addiction or smoking cessation treatments are selected from NRT, administration of bupropion, administration of varenicline, electronic cigarettes, vaping, and a combination thereof.

In some embodiments, the present disclosure further provides a medicament comprising a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, and wherein the subject (a) smoked ten or more cigarettes per day prior to the administration of cytisine, (b) has expired air CO concentration of about 10 ppm or greater prior to the administration of cytisine, or (c) a combination of (a) and (b).

The present disclosure further provides medicaments, such as, a medicament comprising cytisine for treating a nicotine addiction or a nicotine dependence in a subject that is a refractory patient who has failed treatment with one or more nicotine addiction or nicotine dependence treatments, wherein the medicament is for three times daily oral administration to the subject. In some embodiments, the nicotine addiction or nicotine dependence treatments comprise NRT, administration of bupropion, administration of varenicline, electronic cigarettes, vaping, or a combination thereof. In some embodiments, cytisine is provided in a unit dose of about 1.0 mg to about 6.0 mg of cytisine three to six times daily to a subject in need thereof. In certain embodiments, cytisine is provided in a unit dose of 3.0 mg of cytisine three times daily to a subject in need thereof. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b).

In some embodiments, the medicament comprises a unit dose of cytisine in (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine for preventing smoking and/or vaping relapse in a subject in need thereof, wherein the medicament is for three times daily oral administration to the subject. In certain embodiments, cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the subject is a refractory patient who has failed treatment with one or more smoking cessation treatments. In certain embodiments, the smoking cessation treatments comprise NRT, administration of bupropion, administration of varenicline, electronic cigarettes, vaping, or a combination thereof.

The present disclosure further provides medicaments, such as, a medicament comprising cytisine for preventing smoking and/or vaping relapse in a subject that is a refractory patient who has failed treatment with one or more nicotine addiction or nicotine dependence treatments selected from the group consisting of NRT, administration of bupropion, administration of varenicline, electronic cigarettes, or vaping, wherein the medicament is for three times daily oral administration to the subject. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, and wherein cytisine is administered for about 6 weeks or for about 12 weeks. In some embodiments, the subject experiences no adverse events selected from the group consisting of an URTI, abnormal dreams, nausea, insomnia, headache, fatigue, and constipation after receiving the cytisine treatment.

In some embodiments, the present disclosure provides uses of a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, wherein the cytisine is for three times daily oral administration to the subject. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In certain embodiments, the subject experiences no nausea after receiving the cytisine treatment. In some embodiments, cytisine is administered for about 6 weeks or for about 12 weeks. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, the subject is a refractory patient who has failed treatment with one or more nicotine addiction, nicotine dependence, or smoking cessation treatments. In certain embodiments, the nicotine addiction, nicotine dependence, or smoking cessation treatments are selected from NRT, administration of bupropion, administration of varenicline, electronic cigarettes, vaping, and a combination thereof. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the uses further include providing behavioral support to the subject.

The present disclosure further provides uses of cytisine, such as for treating a nicotine addiction or nicotine dependence in a subject that is a refractory patient who has failed treatment with one or more nicotine addiction or nicotine dependence treatments, wherein the cytisine is for three times daily oral administration to the subject. In certain embodiments, the nicotine addiction or nicotine dependence treatments comprise NRT, administration of bupropion, administration of varenicline, electronic cigarettes, vaping, or a combination thereof. In some embodiments, cytisine is provided in a unit dose of about 1.0 mg to about 6.0 mg of cytisine three to six times daily to a subject in need thereof. In certain embodiments, cytisine is provided in a unit dose of 3.0 mg of cytisine three times daily to a subject in need thereof. In certain embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b).

In some embodiments, uses of a unit dose of cytisine in the form of (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine include preventing smoking relapse in a subject in need thereof, wherein the cytisine is for three times daily oral administration to the subject. In some embodiments, cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the subject is a refractory patient who has failed treatment with one or more smoking cessation treatments. In certain embodiments, the smoking cessation treatments comprise NRT, administration of bupropion, administration of varenicline, electronic cigarettes, vaping, or a combination thereof.

In some embodiments, uses of cytisine for preventing smoking relapse in a subject that is a refractory patient who has failed treatment with one or more nicotine addiction or nicotine dependence treatments selected from the group consisting of NRT, administration of bupropion, administration of varenicline, electronic cigarettes, or vaping, wherein the cytisine is for three times daily oral administration to the subject. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In certain embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, and wherein cytisine is administered for about 6 weeks or for about 12 weeks. In some embodiments, the subject experiences no adverse events selected from the group consisting of an URTI, abnormal dreams, nausea, insomnia, headache, fatigue, and constipation after receiving the cytisine treatment.

The present disclosure further provides uses of tablets comprising about 1.0 mg or 1.5 mg of cytisine are for three times daily oral administration of about 3.0 mg of cytisine to a subject to treat a nicotine addiction, a nicotine dependence, promoting cessation of smoking and/or vaping, and/or promoting a reduction in smoking and/or vaping in the subject. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In certain embodiments, the subject experiences no nausea after receiving the cytisine treatment. In some embodiments, cytisine is administered for about 6 weeks or for about 12 weeks. In some embodiments, a unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, the subject is a refractory patient who has failed treatment with one or more nicotine addiction, nicotine dependence, or smoking cessation treatments. In certain embodiments, the nicotine addiction, nicotine dependence, or smoking cessation treatments are selected from NRT, administration of bupropion, administration of varenicline, electronic cigarettes, vaping, and a combination thereof. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the uses further comprise providing behavioral support to the subject.

In some embodiments, the uses of tablets comprising about 1.0 mg or 1.5 mg of cytisine are for three times daily oral administration of about 3.0 mg of cytisine to a subject that is a refractory patient who has failed treatment with one or more nicotine addiction or nicotine dependence treatments to treat a nicotine addiction or nicotine dependence in the subject. In certain embodiments, the nicotine addiction or nicotine dependence treatments comprise NRT, administration of bupropion, administration of varenicline, electronic cigarettes, vaping, or a combination thereof. In some embodiments, cytisine is provided in a unit dose of about 1.0 mg to about 6.0 mg of cytisine three to six times daily to a subject in need thereof. In certain embodiments, cytisine is provided in a unit dose of 3.0 mg of cytisine three times daily to a subject in need thereof. In some embodiments, the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine. In some embodiments, cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b).

In some embodiments, the uses of tablets comprising about 1.0 mg or about 1.5 mg of cytisine are for three times daily oral administration of about 3.0 mg of cytisine to a subject to prevent smoking and/or vaping relapse in the subject. In certain embodiments, the cytisine is administered for about 6 weeks or for about 12 weeks. In some embodiments, the subject experiences no adverse events after receiving the cytisine treatment. In certain embodiments, the adverse event is selected from the group consisting of an URTI, abnormal dreams, nausea, insomnia, headache, fatigue, and constipation. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, the subject is a refractory patient who has failed treatment with one or more smoking cessation treatments. In certain embodiments, the smoking cessation treatments comprise NRT, administration of bupropion, administration of varenicline, electronic cigarettes, vaping, or a combination thereof.

In some embodiments, the uses of tablets comprising about 1.0 mg or about 1.5 mg of cytisine are for three times daily oral administration of about 3.0 mg of cytisine to a subject who has failed treatment with one or more nicotine addiction or nicotine dependence treatments selected from the group consisting of NRT, administration of bupropion, administration of varenicline, electronic cigarettes, or vaping to prevent smoking relapse in the subject. In some embodiments, the subject (a) smoked ten or more cigarettes per day prior to the administration of cytisine, (b) has expired air CO concentration of about 10 ppm or greater prior to the administration of cytisine, or (c) a combination of (a) and (b). In some embodiments, a unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, and wherein cytisine is administered for about 6 weeks or for about 12 weeks. In some embodiments, the subject experiences no adverse events selected from the group consisting of an URTI, abnormal dreams, nausea, insomnia, headache, fatigue, and constipation after receiving the cytisine treatment.

Thus, in yet another aspect, provided herein is a method of treating of nicotine addiction or nicotine dependence in a subject, comprising administering cytisine to a subject in need thereof, wherein the subject is a refractory patient who has failed treatment with one or more nicotine addiction or nicotine dependence treatments. Suitable unit doses include doses between about 1.0 mg and about 6 mg which can be administered three to six times daily, for example, at about equal intervals. For example, in some embodiments, the methods comprise administering cytisine provided in a unit dose of 3.0 mg of cytisine three times daily to a refractory patient. Any suitable duration of administration can be used in the methods disclosed herein, for example, about 26 weeks, about 12 weeks, or about 6 weeks. In some embodiments, the treatment is administered for about 6 weeks.

In some embodiments, the methods disclosed herein can further comprise providing behavioral support to the subject, for example, a refractory patient. Behavioral support can include counseling which can further include, but is not limited to, the following topics: abstinence, past quit experience, anticipate triggers or challenges in the upcoming attempt, alcohol use, proximity to and frequency around other nicotine users (e.g., smokers, vapers), recognition of dangerous situations, and development of coping skills.

In some embodiments, the methods disclosed herein can further comprise providing one or more questionnaires to the subject. Non-limiting examples of the one or more questionnaires include an E-cigarette Dependence Scale questionnaire, a marijuana craving questionnaire-short form, the Fagerström Test for Nicotine Dependence, the Smoking Self-Efficacy questionnaire (SEQ-12), the Brief Questionnaire of Smoking Urges (QSU-Brief) questionnaire, the Minnesota Nicotine Withdrawal Scale (MNWS) questionnaire, the "Since Last Visit" C-SSRS questionnaire, and the HADS questionnaire. In certain embodiments, the questionnaire(s) can be provided to the subject at any time during administration of the composition, before administration of the composition, or after administration of the composition. In some embodiments, the one or more questionnaires are provided to the subject once, twice, three times, four times, five times, six times, seven times, eight times, nine times, ten times, 15 times, 20 times, or 30 times.

The referenced patents, patent applications, and scientific literature referred to herein are hereby incorporated by reference in their entirety as if each individual publication, patent, or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

Example 1: Impact of Cytisine on Treating Nicotine Addiction

This was a six-arm, multi-center, double-blind, randomized, placebo-controlled study conducted in male or female adults years of age, smoking 10+ cigarettes daily, and willing to set a quit date that is 5-7 days after randomization. This study was designed to evaluate the effectiveness of 1.5 mg of cytisine versus placebo using the commercial titration schedule approved in Central and Eastern Europe. The study also evaluated the effectiveness of a simplified TID dosing schedule for 1.5 mg and an increased dose of 3.0 mg (using both the commercial titration (COM) and simplified TID dosing schedules). The overall goal of the study was to obtain estimates of effect size for efficacy and safety endpoints that will be used to inform the design of future Phase 3 studies.

Figure 3:
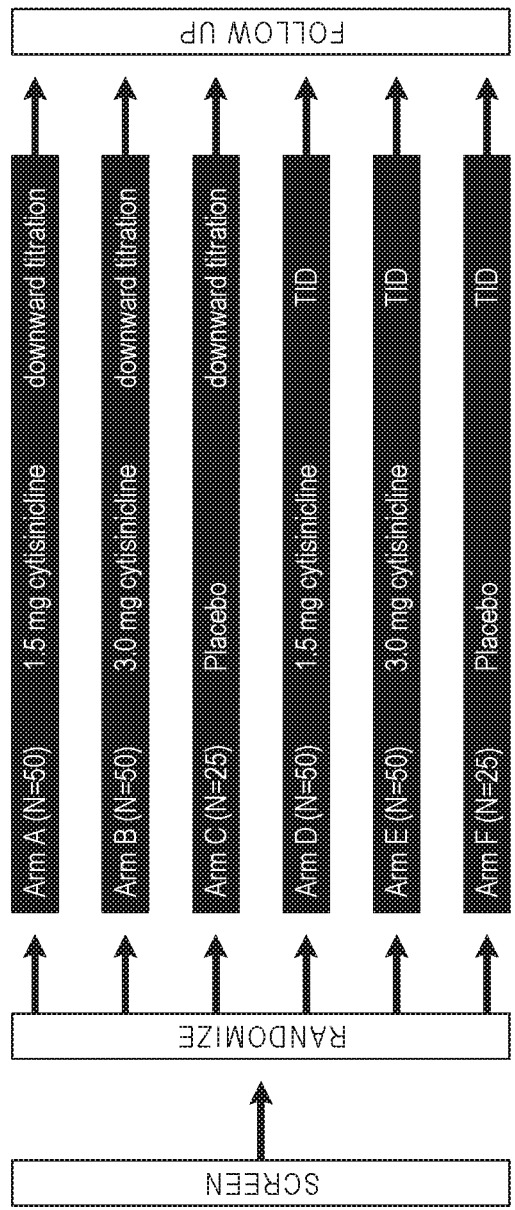
FIG. 3 is a schematic of the dosing strengths, schedules, and duration according to the study design of Example 1 in accordance with the present technology.

The dosing schedules for the study are shown in FIG. 1. The study was double-blinded to dose but not to the administration schedule, and the study arms were as shown in FIG. 2. Study treatment started the day after randomization such that study treatment was initiated prior to the quit date, as shown in FIG. 3.

The primary efficacy endpoint for this study was the percent reduction in the number of cigarettes smoked during treatment, which was calculated as follows:

$$100 - \left[\frac{N}{B \times D} \times 100\right]\%$$

where N=total number of cigarettes smoked, B=number of cigarettes smoked at baseline and D=number of days.

The secondary efficacy endpoint was the quit rate (confirmed by CO<10 ppm) and included an analysis at week 4 (i.e., the end of treatment) and sustained (4-week) abstinence from Week 5 to Week 8 (i.e., off treatment).

Figure 5:
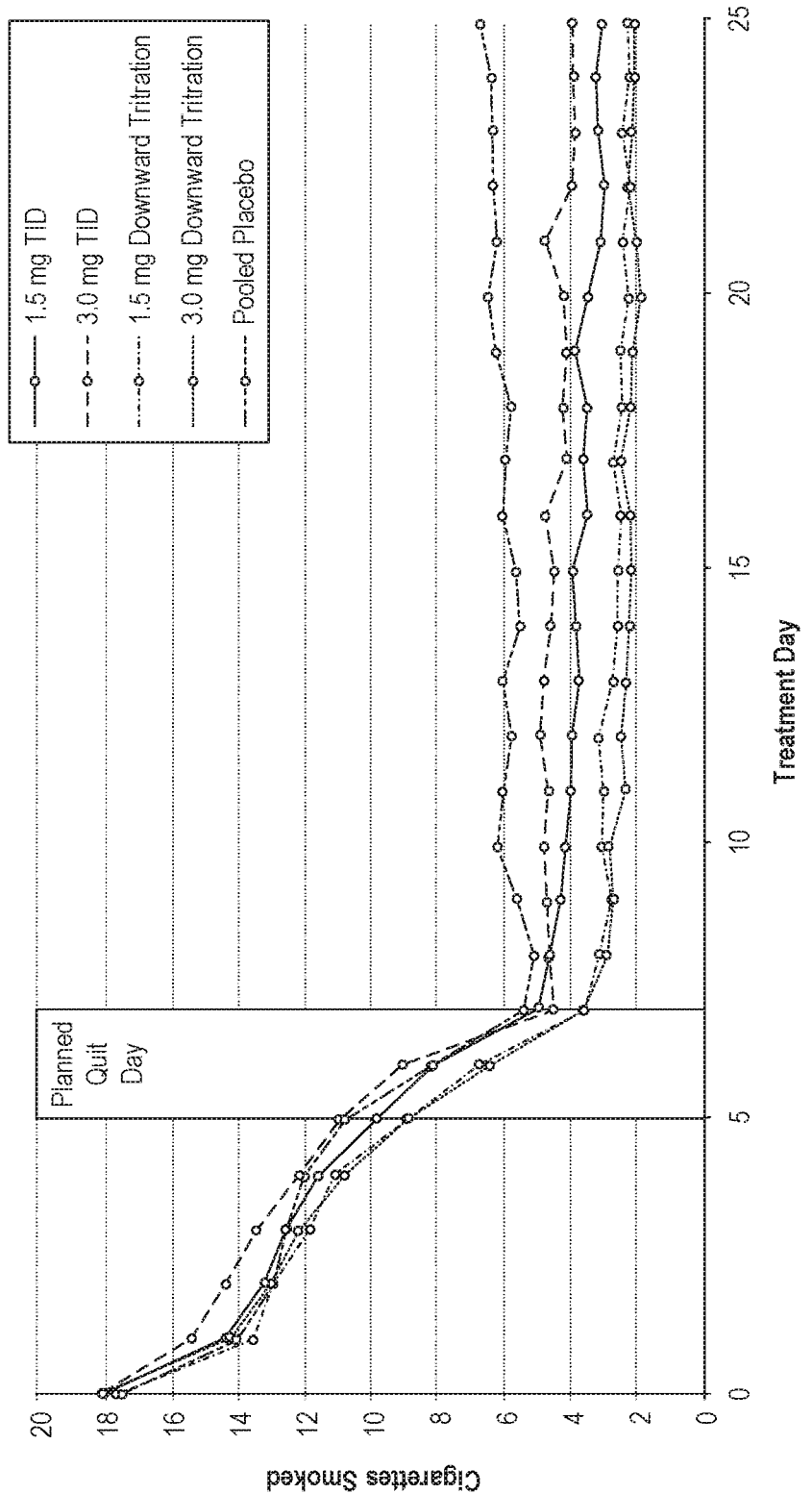
FIG. 5 is a representative graph depicting a number of cigarettes smoked per treatment arm by day of treatment according to the study of Example 1 in accordance with the present technology.

The subject demographics are summarized in FIG. 4. The cigarettes subject's smoked before and after treatment are shown in FIG. 5.

1.1 Results

Table 1 summarizes the demographics of the subjects. In total, 254 male or female adults years of age who smoked ≥10 cigarettes daily and were willing to set a quit date 5 to 7 days after randomization were enrolled in the study. Demographics and baseline characteristics were generally well balanced across both schedules and treatment arms.

TABLE 1

Subject Demographics

| | Downward Titration | | TID | | Placebo | |
|---|---|---|---|---|---|---|
| | 1.5 mg (n = 51) | 3.0 mg (n = 50) | 1.5 mg (n = 52) | 3.0 mg (n = 50) | (n = 51) | ALL (n = 254) |
| Sex | | | | | | |
| Male | 23 (45%) | 30 (60%) | 23 (44%) | 25 (50%) | 20 (39%) | 121 (47%) |
| Female | 28 (55%) | 20 (40%) | 29 (56%) | 25 (50%) | 31 (61%) | 133 (53%) |
| Race | | | | | | |
| White | 43 (84%) | 40 (80%) | 37 (71%) | 41 (82%) | 39 (76%) | 200 (80%) |
| Black | 7 (14%) | 9 (18%) | 13 (25%) | 7 (14%) | 10 (20%) | 46 (18%) |
| Asian | 0 | 0 | 1 (2%) | 1 (2%) | 1 (2%) | 3 (1%) |
| Pacific | 0 | 0 | 0 | 0 | 0 | 0 |
| Native | 0 | 1 (2%) | 1 (2%) | 0 | 0 | 3 (1%) |
| Other | 1 (2%) | 0 | 0 | 1 (2%) | 1 (2%) | 3 (1%) |
| Age (mean years) | 49.8 | 50.0 | 47.0 | 46.3 | 48.9 | 48.4 |
| Weight (mean kg) | 82.1 | 83.0 | 80.7 | 79.5 | 80.2 | 81.1 |
| BMI (mean kg/m$^2$) | 27.6 | 27.8 | 27.9 | 27.1 | 27.9 | 27.7 | old and had been smoking for 32 years, meaning that most of them had started smoking in their adolescent years. In addition, they had an average of 4.5 prior quit attempts with the last quit attempt approximately 3.7 years prior to entering the study and were currently smoking on average a pack of cigarettes a day. Of the previous quit attempts, 35% of the subjects had previously received varenicline, 16% of the subject had bupropion, and 48% of the subjects an NRT.

TABLE 2

Subject Smoking History

| | Downward Titration | | TID | | | |
|---|---|---|---|---|---|---|
| | 1.5 mg (n = 51) | 3.0 mg (n = 50) | 1.5 mg (n = 52) | 3.0 mg (n = 50) | Placebo (n = 51) | ALL (n = 254) |
| Smoking duration (mean years) | 33.3 | 33.2 | 30.9 | 30.0 | 33.0 | 32.1 |
| Daily smoking (median cigarettes) | 20 | 20 | 20 | 18 | 20 | 20 |
| Prev quit attempts (mean) | 5.4 | 3.8 | 4.7 | 3.8 | 4.9 | 4.5 |
| Previous treatments | | | | | | |
| Chantix ® | 21 (41%) | 13 (26%) | 21 (40%) | 18 (36%) | 19 (37%) | 92 (36%) |
| Zyban ® | 9 (18%) | 3 (6%) | 9 (17%) | 7 (14%) | 12 (24%) | 40 (16%) |
| NRT gum | 20 (39%) | 12 (24%) | 20 (38%) | 16 (32%) | 24 (47%) | 92 (36%) |
| NRT patch | 23 (45%) | 19 (38%) | 27 (52%) | 25 (50%) | 28 (55%) | 122 (48%) |
| e-cigarettes/vaping | 15 (29%) | 11 (22%) | 19 (36%) | 13 (26%) | 18 (35%) | 76 (30%) |

Of the study population, 53% percent were female and 47% male. 79% of the study population was white, with 18% black and 3% of another race. Smoking diary compliance, on which the primary analysis was based in part, was high for all treatment arms. Study drug compliance was >94% for all treatment arms with slightly higher compliance with the TID schedule (>98%). The mean treatment duration was 23.4 days and 96.6% of the subjects received the mean doses of cytisine.

Table 2 summarizes the smoking history of the subjects in all treatment arms. Overall, the study population represented highly addictive smokers who on average were 48.4 years Analyses from the international EAGLES trial provided clear evidence that smoking at a young age and being of U.S. origin was associated with lower success rates for quitting. The lower success rate in U.S. smokers supports the view that smokers in the U.S. may have reached a point in the tobacco epidemic such that those who continue to smoke, despite strong cultural pressures not to, have particular characteristics that make it more difficult for them to stop smoking.

Overall, study drug compliance was high for all treatment arms with the TID schedule better (98.18%) than the commercial schedule (94.90%). More specifically, Table 3 summarizes the study drug compliance in all treatment arms. Study drug compliance ranged from 96.7% to 99.5% in the TID arms while study drug compliance ranged from 94.2% to 96.4% in the COM arms.

TABLE 3

Study Drug Compliance

|  | Downward Titration Schedule | | | TID Schedule | | |
|---|---|---|---|---|---|---|
|  | 1.5 mg<br>N = 51 | 3.0 mg<br>N = 50 | Placebo<br>N = 25 | 1.5 mg<br>N = 52 | 3.0 mg<br>N = 52 | Placebo<br>N = 26 |
| Treatment Duration Mean Days (std) | 23.8 (4.76) | 23.5 (4.49) | 23.9 (4.06) | 25.0 (0.14) | 24.9 (0.72) | 24.3 (3.53) |
| Percent of Doses Missed Mean % (std) | 5.1 (18.1) | 5.8 (15.8) | 3.6 (13.7) | 0.5 (1.2) | 2.4 (7.7) | 3.3 (13.6) |
| Compliance* | 94.9% | 94.2% | 96.4% | 99.5% | 97.6% | 96.7% |
| 100% | 33 (64.7%) | 32 (64.0%) | 20 (88.0%) | 42 (80.8%) | 37 (74.0%) | 20 (76.9%) |
| 90% - <100% | 13 (25.5%) | 12 (24.0%) | 3 (12.0%) | 10 (19.2%) | 10 (20.0%) | 5 (19.2%) |
| 80% - <90% | 3 (5.9%) | 1 (2.0%) | 3 (5.9%) | 0 | 1 (2.0%) | 0 |
| <80% | 2 (3.9%) | 5 (10.0%) | 2 (3.9%) | 0 | 2 (4.0%) | 1 (3.8%) |

*Defined as [(# doses prescribed - # missed doses)/# doses prescribed] X 100.

Figure 6:
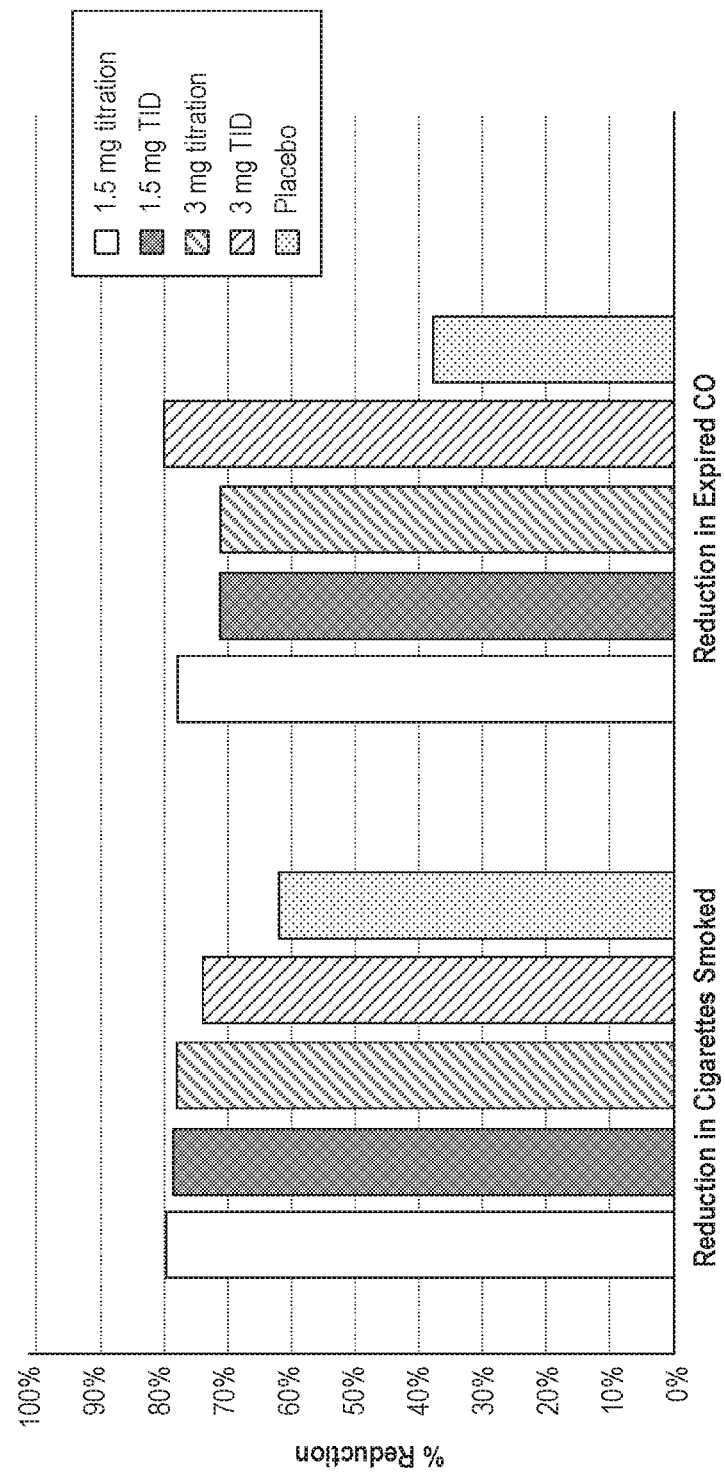
FIG. 6 is a representative graph depicting a reduction in cigarettes smoked versus expired CO in the subject population of Example 1 in accordance with the present technology.

The reduction in cigarettes smoked in all treatment arms is shown in FIG. 6 and summarized in Table 4. Results from the primary analyses demonstrated a significant reduction in percentage of expected cigarettes smoked (Cigarette Score) in both COM arms. When pooling the placebo arms, the Cigarette Score was significantly reduced in both COM arms, the 1.5 mg TID arm, and approached significance in the 3.0 mg TID arm. Subjects treated with 1.5 mg or 3.0 mg of cytisine using the COM schedule smoked approximately 14% to 16% fewer cigarettes than expected versus placebo. Subjects treated with 1.5 mg or 3.0 mg of cytisine on the TID schedule smoked approximately 9% to 12% fewer cigarettes than expected versus the placebo arm.

TABLE 4

Reduction of Cigarettes Smoked and CO

|  | Reduction in cigarettes smoked | p-value | Reduction in CO |
|---|---|---|---|
| Titration |  |  |  |
| 1.5 | 80% | 0.001 | 78% |
| 3.0 | 78% | 0.003 | 71% |
| Placebo | 62% |  | 40% |
| TID |  |  |  |
| 1.5 | 79% | 0.009 | 71% |
| 3.0 | 74% | 0.052 | 80% |
| Placebo | 62% |  | 29% |

Although the decreases on the TID schedule were not as high as those seen on the COM schedule, it should be noted that subjects in the placebo arm on the TID schedule reported a higher reduction in cigarettes smoked than subjects in the placebo arm on the COM schedule. The TID placebo subjects smoked only one-third as many cigarettes as they normally would (LS mean: 35.30%) versus the COM placebo subjects at one-half as many cigarettes smoked (LS mean: 47.10%), which possibly masked the cytisine treatment effect on the TID schedule.

Expired CO levels were also measured during this study as an objective biochemical marker for reduction in smoking. The reduction in CO in all treatment arms is shown in FIG. 6 and summarized in Table 4. In all cytisine-treated arms, the reduction in CO (55% to 62% reduction) was consistent with the reported reduction in cigarettes smoked (e.g., a range of 25% to 32% as Cigarette Scores represents a 75% to 68% reduction in cigarettes smoking). Conversely, in the placebo-treated arms, the reported reductions in the number of cigarettes smoked (e.g., 41% as the Cigarette Score, representing a 59% reduction in cigarettes smoked) was not paralleled by a corresponding reduction in CO at only 29%. A similar pattern for plasma cotinine levels was observed with far greater reductions in cotinine levels in the cytisine arms compared to placebo arms.

The changes in these objective markers suggest that, in general, placebo-treated subjects over-reported their reduction in cigarettes smoked. It also suggests that the real differences in Cigarette Scores between subjects treated with cytisine and those treated with placebo were greater than those actually observed.

Figure 8:
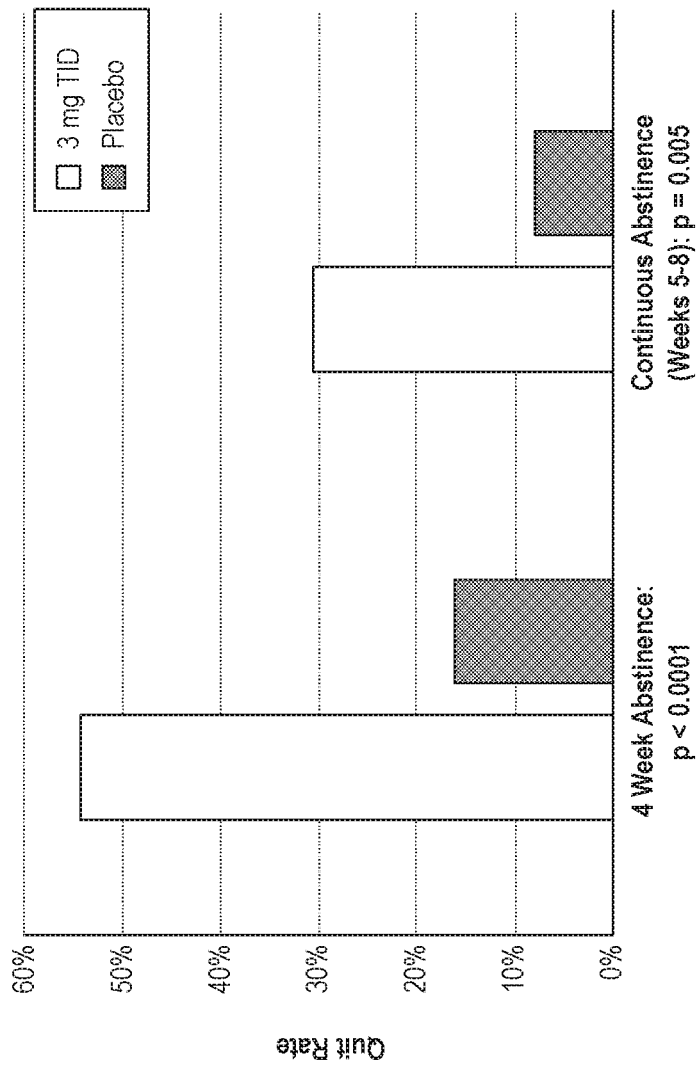
FIG. 8 is a representative graph depicting a comparison between the quit rates between 3.0 mg three times per day (TID) and placebo after a 4-week abstinence and during continuous abstinence (Weeks 5-8).

The quit rates for arms of the TID schedule versus placebo is shown in FIGS. 7 and 8 and summarized in Table 5. Results for the initial quit rate at Week 4 demonstrated both arms of the TID schedule had high odds of success of quitting smoking compared with placebo; subjects in the 3.0 mg of cytisine arm had the best odds of success for quitting smoking: OR: 6.31 (95% CI: 2.28, 18.45). The OR for the 1.5 mg of cytisine arm on the TID schedule was 5.81 (95% CI: 2.12, 16.87). On the COM schedule, the ORs for the 1.5 and 3.0 mg of cytisine arms were 5.59 (95% CI: 2.03, 16.29) and 5.38 (95% CI: 1.95, 15.72), respectively.

TABLE 5

Quit Rates - Cytisinicline versus Placebo

|  | End-of-Treatment Week 4 | | Continuous Abstinence Weeks 5 to 8 | |
|---|---|---|---|---|
|  | Quit Rate | p-value | Quit Rate | p-value |
| Titration |  |  |  |  |
| 1.5 | 51% | <0.001 | 22% | 0.09 |
| 3.0 | 50% | <0.001 | 16% | 0.23 |
| Placebo | 16% |  | 8% |  |
| TID |  |  |  |  |
| 1.5 | 52% | <0.001 | 27% | 0.018 |
| 3.0 | 54% | <0.001 | 30% | 0.005 |
| Placebo | 15% |  | 8% |  |

Referring to FIGS. 7 and 8 and Table 5, for the prolonged abstinence from Week 5 to Week 8 endpoint, both arms of the TID schedule had higher odds of success for abstinence compared with placebo; subjects in the 3.0 mg of cytisine arm had the best odds of success for abstinence from Weeks 5 to 8, with an OR of 5.04 (95% CI: 1.42, 22.32). The OR for the 1.5 mg of cytisine arm on the TID schedule was 4.33 (95% CI: 1.21, 19.30). On the COM schedule, the ORs for the 1.5 mg of cytisine and 3.0 mg arms were 3.23 (95% CI: 0.86, 14.85) and 2.24 (95% CI: 0.55, 10.82), respectively.

Table 6 summarizes a comparison of the reduction in expired CO levels and quit rates at Week 4 and Weeks 5 to 8 for the 3.0 mg of cytisine arm versus placebo.

TABLE 6

Reduction in CO and Quit Rates for 3 mg TID versus Placebo

| Characteristic | 3.0 mg CYT (N = 50) | Placebo (N = 51) | P Value |
|---|---|---|---|
| Reduction in expired CO | 80% | 38% | p = 0.003 |
| Week 4 Abstinence | 54% | 16% | p < 0.001 |
| Continuous Abstinence (Weeks 5-8) | 30% | 8% | p = 0.005 |

Subjects in the cytisine arms on the TID schedule also had higher odds of smoking abstinence at the Weeks 6, 7, and 8 timepoints compared with subjects in the corresponding arms on the COM schedule versus placebo, as demonstrated by higher ORs at each timepoint.

1.2 Sensitivity Objectives and General Methods

The primary outcome (Cigarette Score) and the main secondary abstinence outcomes were subjected to sensitivity analyses. The main secondary abstinence outcomes were the initial quit rate at Week 4 and continued 4-week abstinence through Week 5 to Week 8, confirmed by expired CO of <10 ppm designated as Cess/W5-8/CO Success. The objective was to assess the robustness of the findings from the trial, and to perform alternative analyses that might either confirm the observed results or challenge the conclusions of the trial.

Other outcomes related to objective biochemical assessments were also analyzed. The associations between these biochemical assessments are particularly important when used as part of the definition of smoking cessation and abstinence but are also important because of absence of assessment subjectivity.

The focus of these sensitivity analyses in this report is on the comparison of the 3.0 mg of cytisine TID arm to the pooled placebo (0 mg of cytisine) arm. Some analyses will show the other comparisons for contrast.

Effect of Modification Analysis Methodology

A common method for assessing robustness, consistency, and meaning of results from a trial is to perform Effect Modifier Analyses (EMAs). The goal of an EMA is to evaluate the degree to which arm effects estimated for discrete values of a baseline attribute differ. For example, an EMA of sex estimates sex-specific arm effects and evaluates whether these estimates differ. If a baseline attribute to be evaluated using EMA is not discrete, the attribute is made discrete by specifying cutpoints based on external criteria or by using percentiles computed from the pooled data (median, tertiles, or quartiles). For example, baseline CO levels split at below 10 ppm or not or using pooled quartile values.

An EMA fits a statistical model to the data. The EMA model has interaction terms for detecting the existence of arm effect differences across discrete factor values. Heterogeneity of effect estimates is detected when interaction terms materially improve the fit of the model over the model without interaction terms. The improvement of fit due to interaction terms is measured by an interaction P value, where a small P value, usually less than 0.10, indicates improvement of fit.

There are two types of interactions: qualitative and quantitative. A quantitative interaction exists when the directions of the arm effect estimates are the same for all discrete values of the factor. A qualitative interaction exists when the direction of effects is mixed for values of the factor.

The results from the multiple EMAs performed in this study are displayed compactly as forest graphs, showing for each factor value the subset-related frequencies (distribution between arms), effect estimate, and applicable confidence interval. The EMA forest graphs provide a gestalt concerning the stability of the overall effect estimate for the factors included in the graph. Complete EMA forest graphs also show for each factor the quantitative assessment of heterogeneity from the EMA model, for example, the interaction P value. Also, arm effect estimates and confidence intervals for each value of the factors are displayed in the forest graphs. (Such forest graphs appear subsequently.)

Justification for Pooling Control Arms

The between-arm comparisons were the pairwise comparisons of each active arm to the pooled placebo arm. The justification for comparing to the pooled placebo was based on:

The absence of evidence that the two placebo arms differed with respect to the primary or the two secondary outcomes with P values 0.1197, 0.9963, and 0.9996, respectively, for the stratified between-control-arm comparisons of the Cigarette Score, initial quit success at Week 4, and Cess/W5-8/CO success outcomes.

The absence of evidence that the randomization between the placebo arms differed with respect to any of the baseline attributes used as factors in the subsequently presented EMAs, including clinical site.

For the purposes of sensitivity assessment, this absence of evidence of placebo arm differences is regarded as justification for pooling, with the benefit of increased statistical sensitivity.

Descriptive Graphs for Daily Reported Mean Cigarettes

Longitudinal graphs for the mean of the number of cigarettes reported in the diaries for each study treatment day (Days 1-25 following randomization) are presented below. Each arm and the pooled placebo arm are shown in a different color or dashed versus solid lines. FIG. 5 illustrates that at each day, subjects did reduce their daily number of cigarettes smoked in an attempt to quit by the planned quit interval (Days 5-7) with abstinence by Day 8.

1.3 Biochemical Verification Analysis

Following are two longitudinal graphs of the visit means and 95% confidence intervals of CO and cotinine, respectively, by the pooled placebo arm and cytisine-treated arms.

Figure 9:
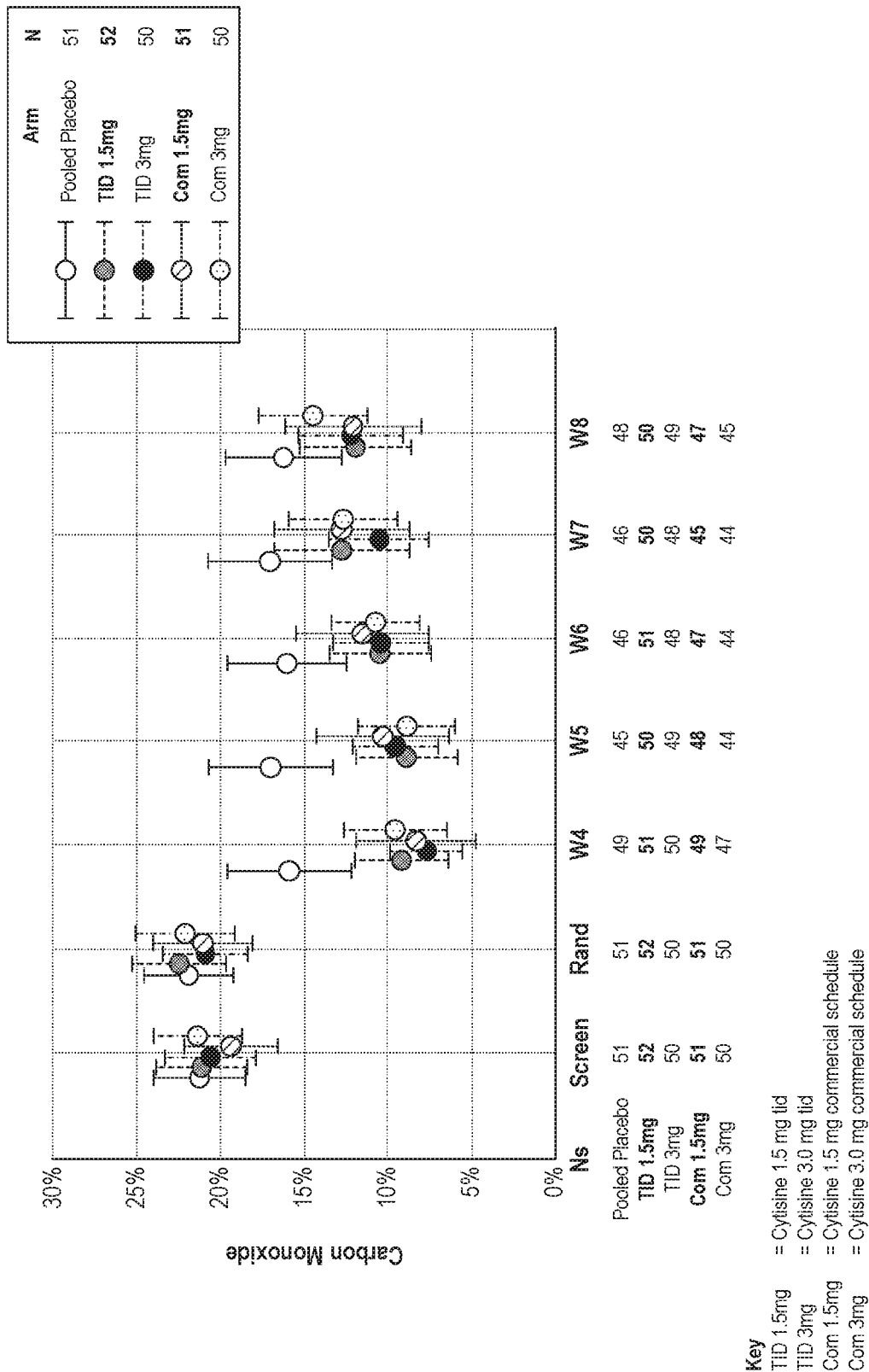
FIG. 9 is a representative plot depicting the expired CO levels in parts per million for the pooled placebo, TID 1.5 mg, TID, 3.0 mg, commercial dosing titration schedule (COM) with 1.5 mg, and COM with 3.0 mg treatment arms at the screening visit, at Week 4, and at Week 8 in accordance with the present technology.

CO levels (ppm) were assessed during the study at screening, baseline, end of study treatment intervention (Week 4), and weekly through Week 8 (FIG. 9). The screening and baseline visits' CO means were approximately equal for all arms. At Week 4, significant reductions in CO levels for all subjects treated in cytisine-treated arms, regardless of schedule, were observed. During the follow-up period (with only behavioral support) from Week 4 through Week 8, the CO means in the pooled placebo arm were approximately constant, although somewhat lower than the means before the start of study treatment intervention. The means for the active treatment arms remained distinctly lower compared to the pooled placebo arm for all follow-up visits, although the means showed a slight upward trend.

Figure 10:
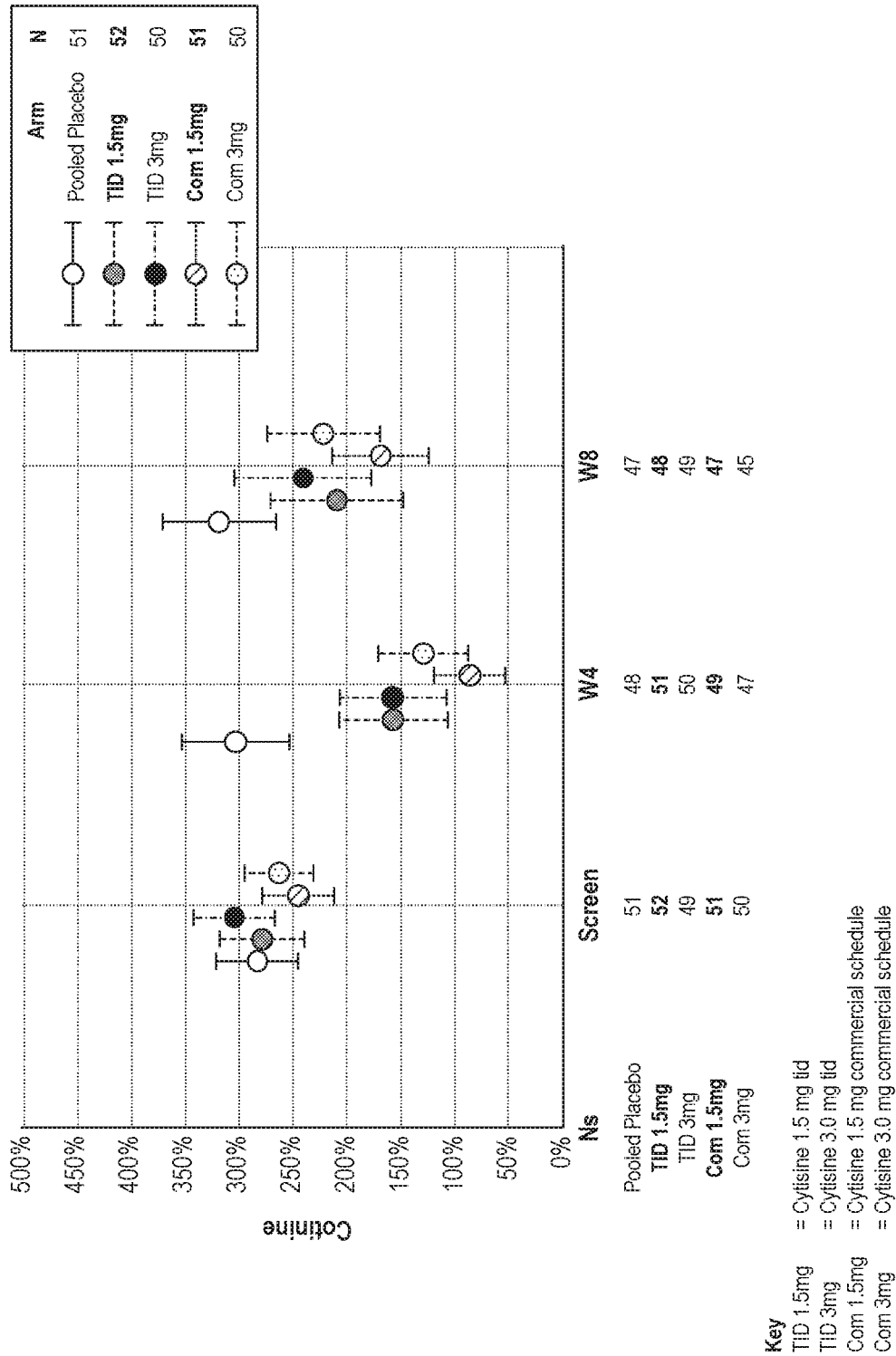
FIG. 10 is a representative plot depicting the serum cotinine levels for the pooled placebo, TID 1.5 mg, TID 3.0 mg, COM 1.5 mg, and COM 3.0 mg at the screening visit, at Week 4, and at Week 8 in accordance with the present technology.

Serum cotinine levels were exploratory and assessed only at screening, Week 4, and Week 8. Reported results for cotinine of <10 ng/mL were transformed to 0 ng/mL prior to statistical analysis. The cotinine graph in FIG. 10 showed the same pattern as observed for CO. All subjects in cytisine-treated arms had a material reduction in cotinine levels at Week 4 and showed a slight upward trend by Week 8.

1.4 Cigarette Score Analysis

Primary Model Stratification and Covariate Assumptions

The primary model of Cigarette Score included covariates for the BMI stratification (3 levels) and the mean number of cigarettes reported by screening diary. The validity of the conclusions from the results of the primary model depended on there being no interaction between each of these covariates and the arm variable. If one or both of these interactions were material in the statistical model, then the magnitude of the estimated arm effect would be a function of BMI class and/or the mean number of cigarettes reported by screening diary.

The planned statistical analyses of the primary endpoint were performed and, as part of those analyses, each of the cytisine treatment arms was compared to the Pooled Placebo arm on the primary efficacy endpoint (Cigarette Score). These analyses were performed using analysis of variance models with fixed effects of treatment arm and BMI (18.5 to <25 kg/m$^2$; 25 to <30 kg/m$^2$; 30 to <35 kg/m$^2$) and a covariate of baseline cigarettes. The analysis used a BMI variable derived from the subjects' actual BMI and omitted one subject (104-144) because the subject's BMI (39.9 kg/m$^2$) was greater than the upper limit of the top BMI category (30 to <35 kg/m$^2$).

Two variations on this analysis were performed as part of the sensitivity analyses. These were:
- A model that used a BMI variable derived from the subject's actual BMI, but that included all 254 subjects in the All Randomized Set. The BMI categories used in this analysis were 18.5 to <25 kg/m$^2$; 25 to <30 kg/m$^2$; 30 to <35 kg/m$^2$, and 35 kg/m$^2$.
- A model that used the BMI stratification variable at randomization. Subject 104-144 was included in this analysis, within the BMI stratum reported for that subject at randomization (30 to <35 kg/m$^2$). Consequently, this analysis included all 254 subjects in the All Randomized Set. The BMI categories used in this analysis were 18.5 to <25 kg/m$^2$; 25 to <30 kg/m$^2$; and 30 to <35 kg/m$^2$.

Figure 11A:
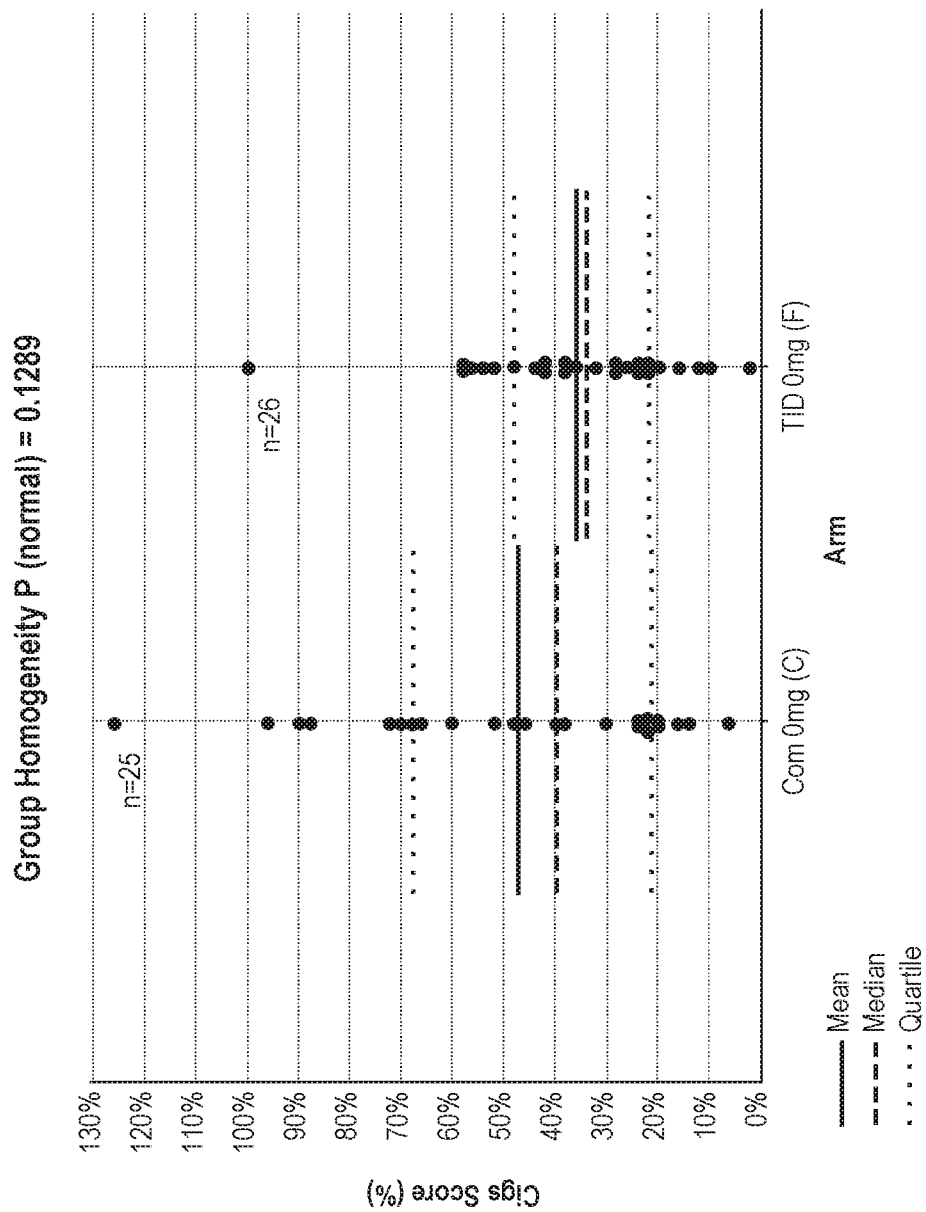
FIGS. 11A-11B are representative plots depicting a comparison between the group homogeneity for the percentage of expected cigarettes smoked (Cigarette Score) compared between COM 0 mg and TID 0 mg, and between TID 0 mg and TID 3.0 mg in accordance with the present technology.
Figure 11B:
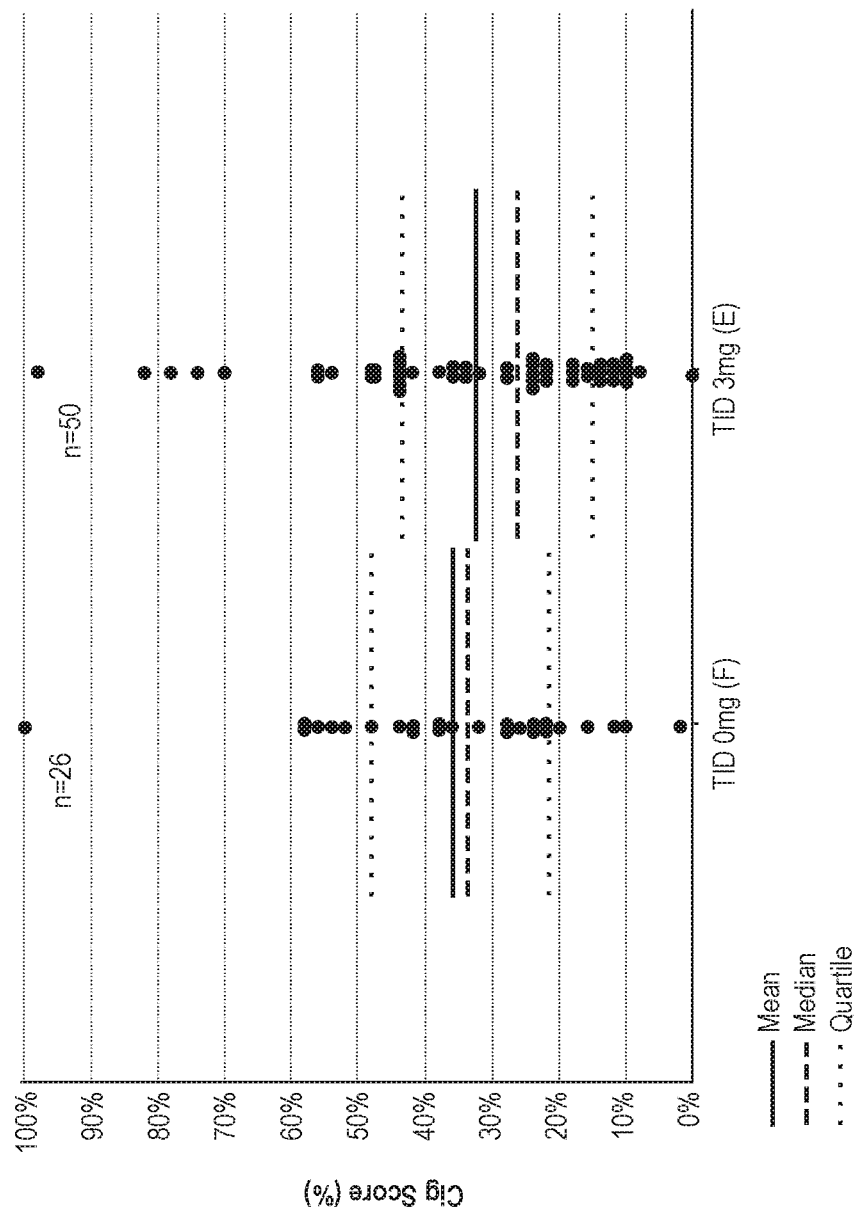

FIGS. 11A-11B show a comparison between homogeneity of each group (COM 0 mg and TID 0 mg, and between TID 0 mg and TID 3.0) as a factor of the percentage of expected cigarettes smoked (Cigarette Score).

Figure 16:
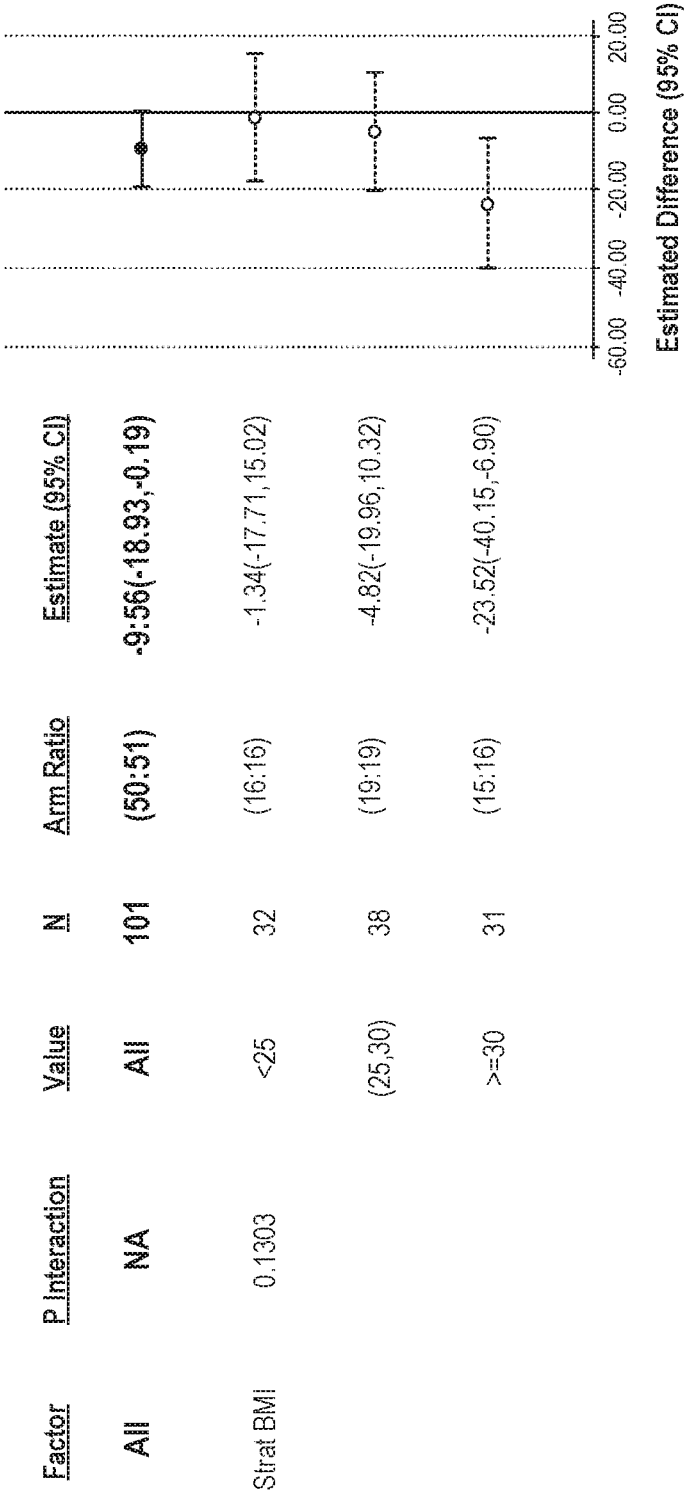
FIG. 16 is a representative plot depicting the interaction between the 3.0 mg TID arm and the BMI stratifier in accordance with the present technology.
Figure 17:
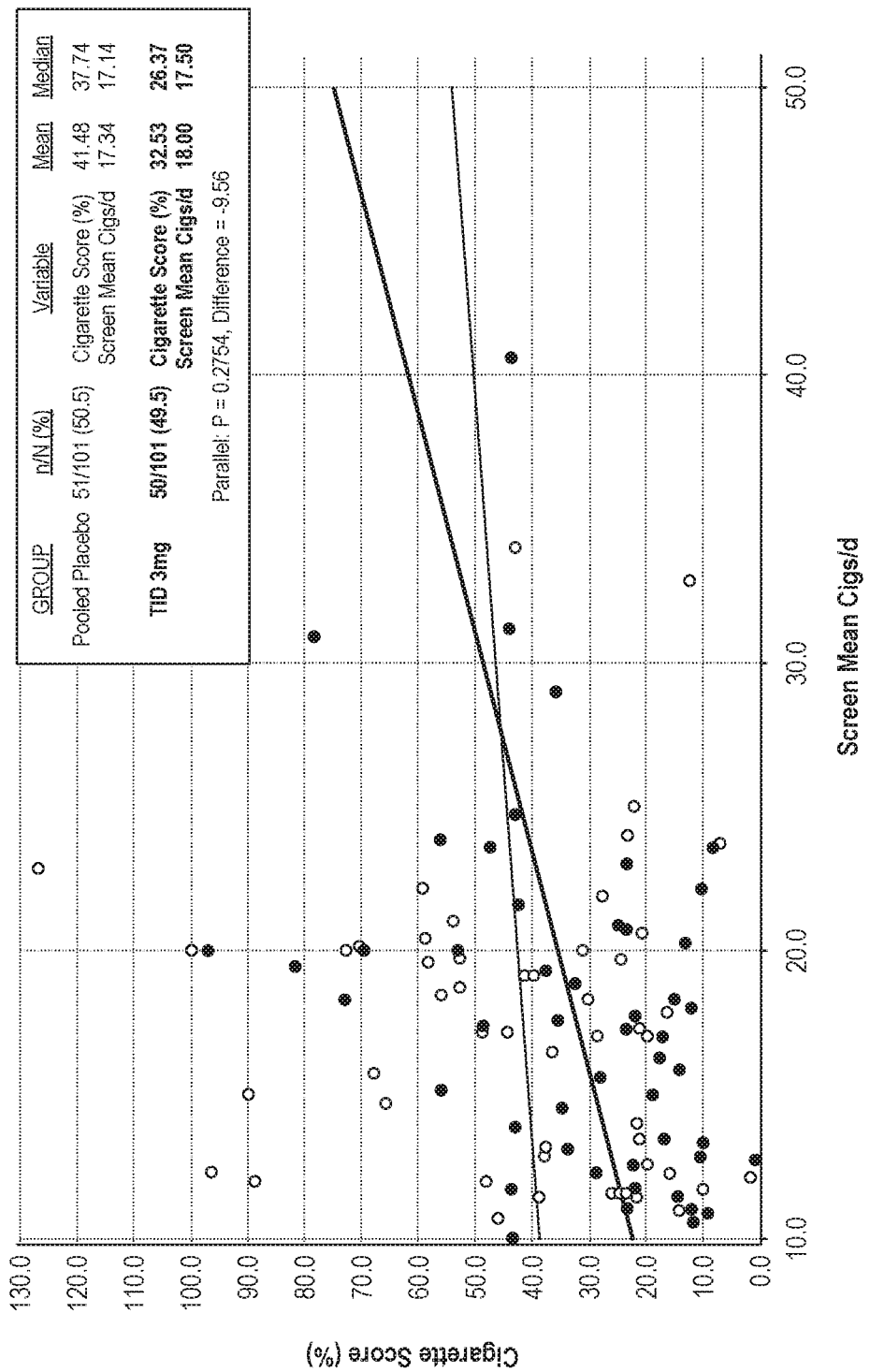
FIG. 17 is a representative plot depicting an assessment using parallelism between the arms of the straight-line relationships between the Cigarette Score and the baseline mean number of cigarettes in accordance with the present technology.
Figure 18:
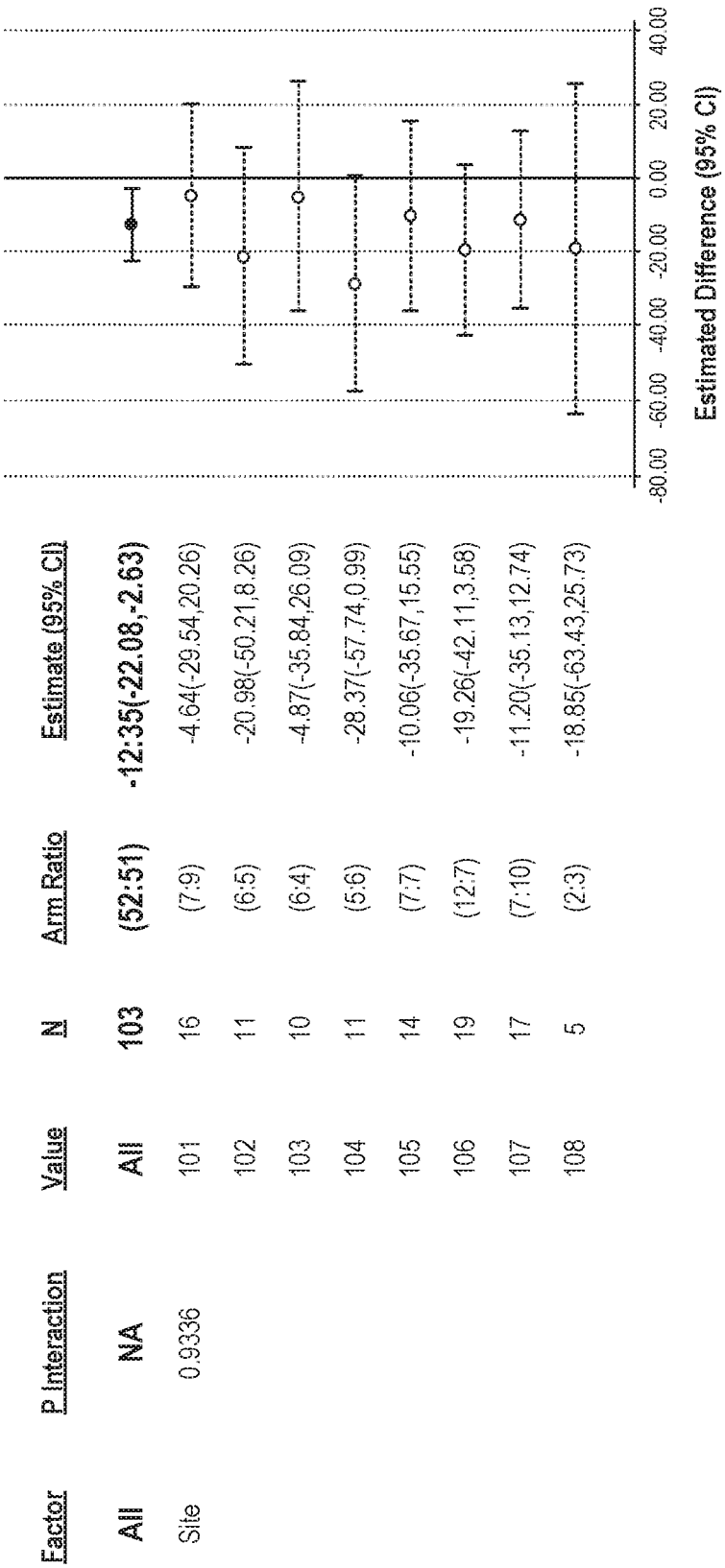
FIG. 18 is a representative plot depicting Effect Modifier Analyses (EMAs) for Cigarette Score across clinical sites for cytisine 1.5 mg TID compared to pooled placebo in accordance with the present technology.
Figure 19:
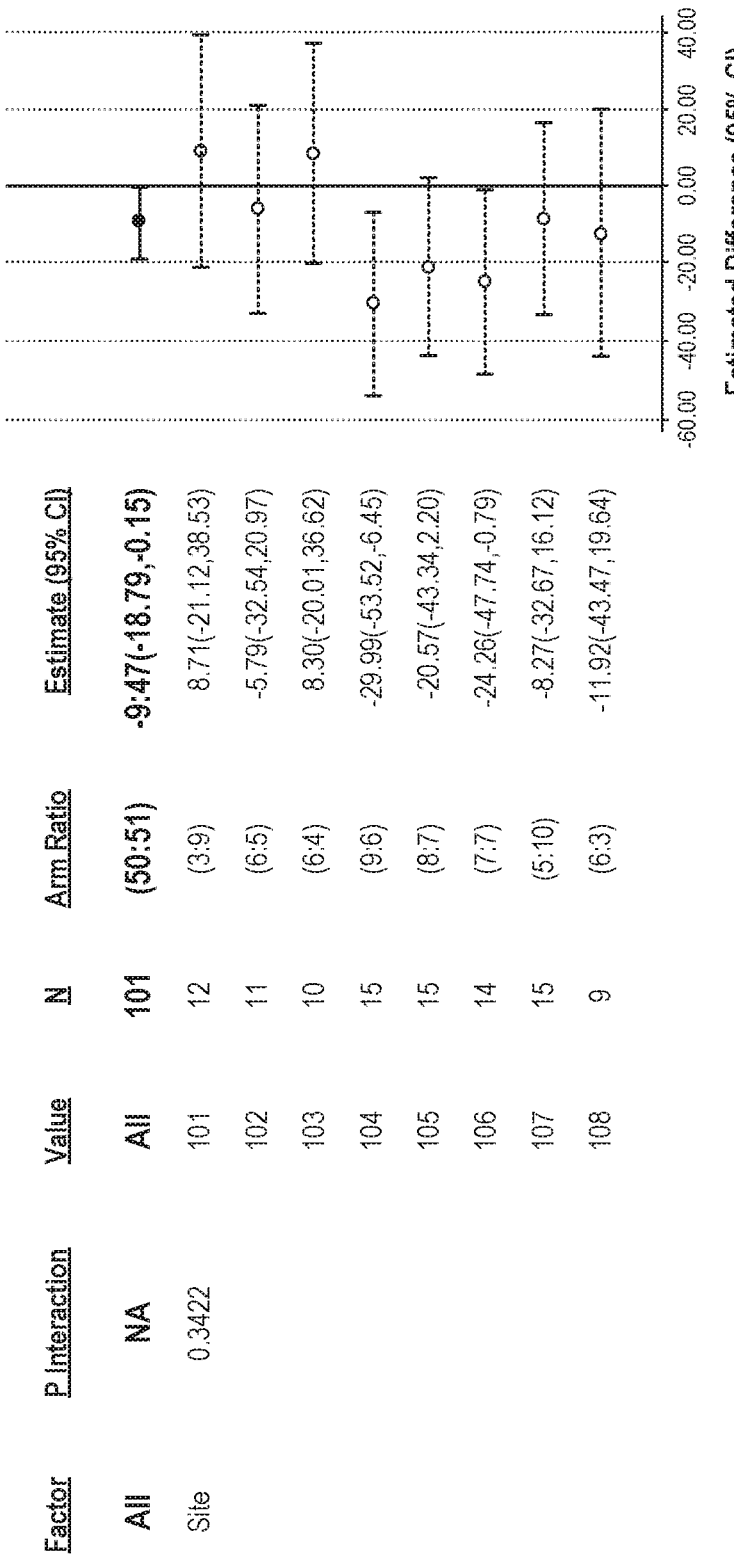
FIG. 19 is a representative plot depicting EMAs for Cigarette Score across clinical sites for cytisine 3.0 mg TID compared to pooled placebo in accordance with the present technology.
Figure 20:
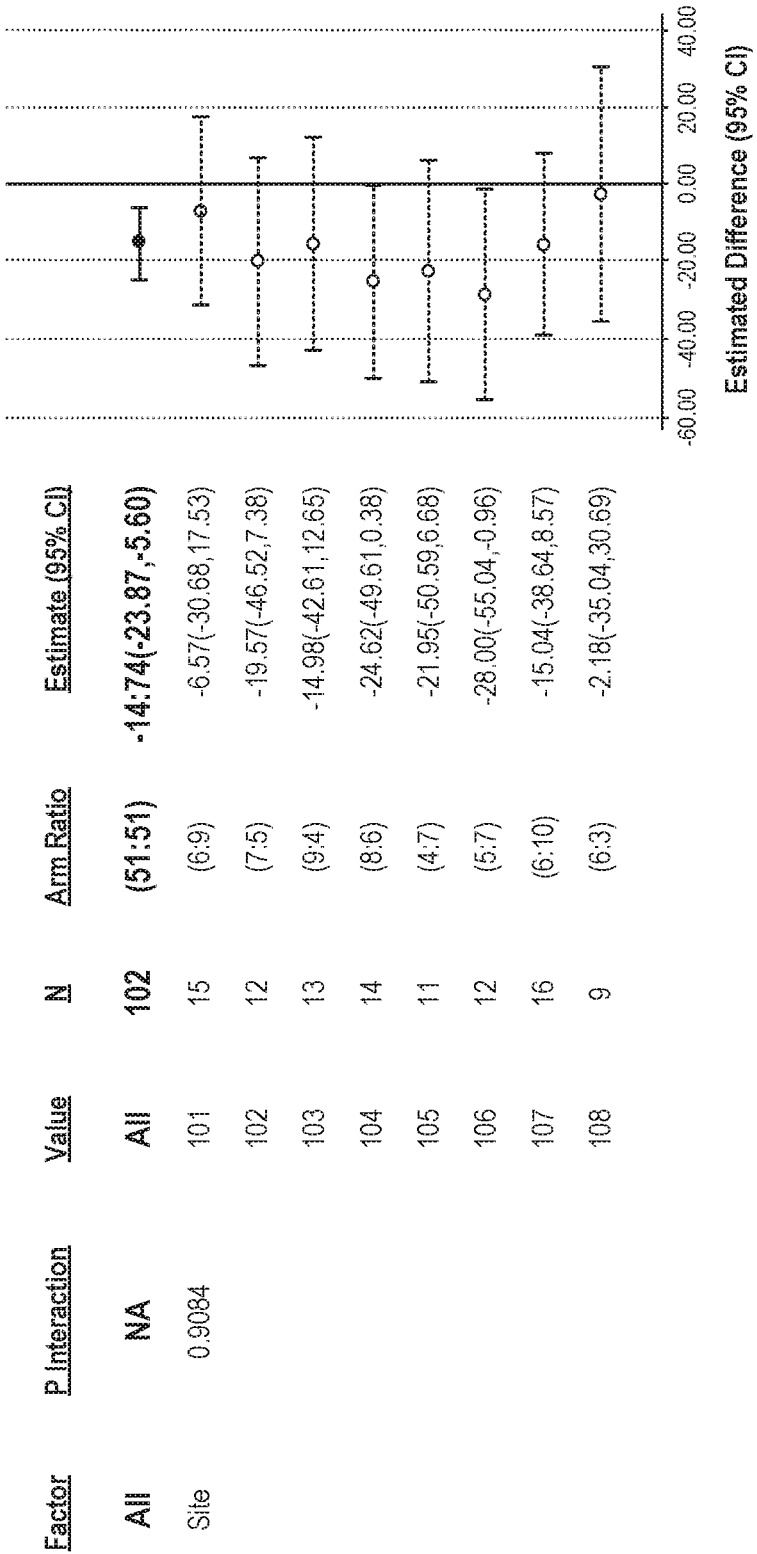
FIG. 20 is a representative plot depicting EMAs for Cigarette Score across clinical sites for cytisine 1.5 mg COM compared to pooled placebo in accordance with the present technology.
Figure 21:
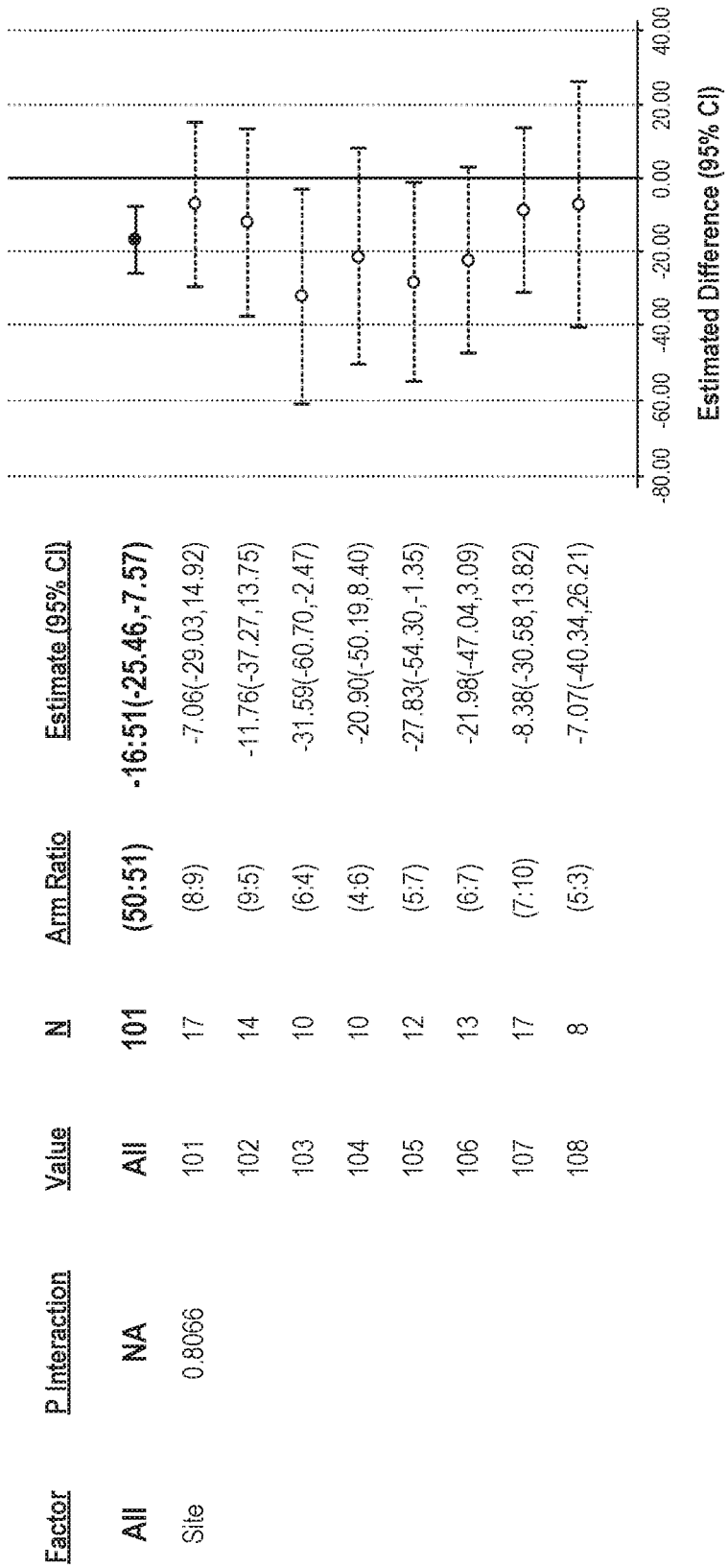
FIG. 21 is a representative plot depicting EMAs for Cigarette Score across clinical sites for cytisine 3.0 mg COM compared to pooled placebo in accordance with the present technology.
Figure 22:
FIG. 22 is a representative plot depicting EMAs for continued 4-week abstinence through Week 5 to Week 8, confirmed by expired CO of <10 ppm (Cess/W5-8/CO Success) across clinical sites for cytisine 1.5 mg TID compared to pooled placebo in accordance with the present technology.
Figure 23:
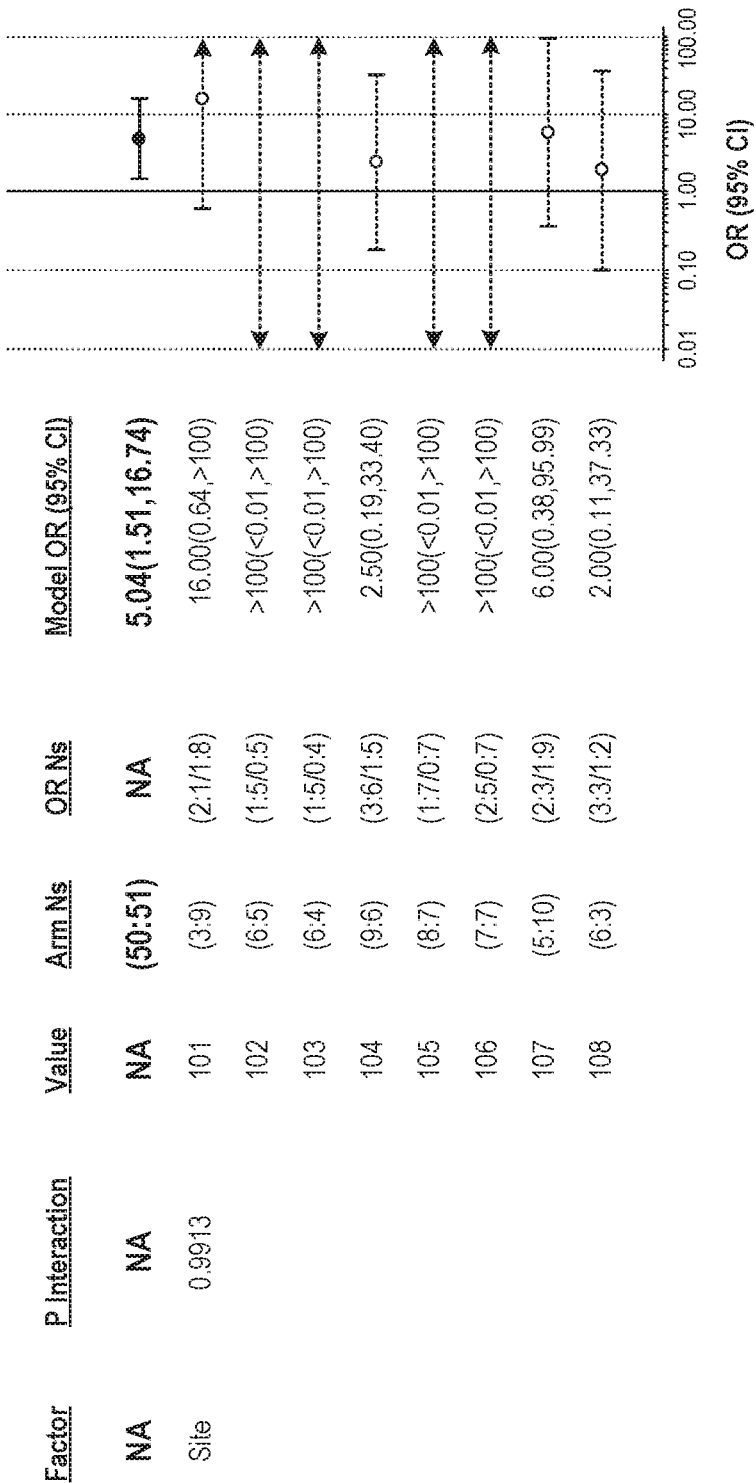
FIG. 23 is a representative plot depicting EMAs for continued 4-week abstinence through Week 5 to Week 8, confirmed by expired CO of <10 ppm (Cess/W5-8/CO Success) across clinical sites for cytisine 3.0 mg TID compared to pooled placebo in accordance with the present technology.
Figure 24:
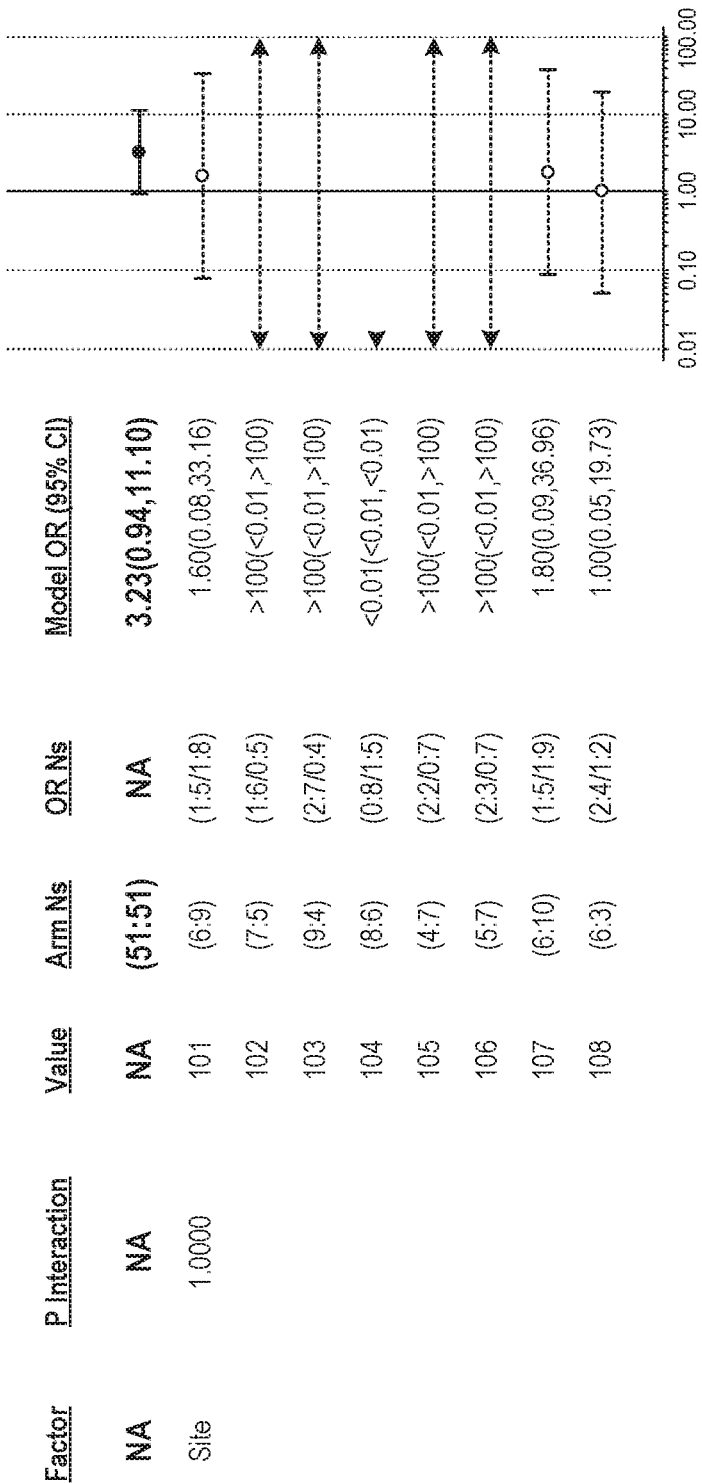
FIG. 24 is a representative plot depicting EMAs for continued 4-week abstinence through Week 5 to Week 8, confirmed by expired CO of <10 ppm (Cess/W5-8/CO Success) across clinical sites for cytisine 1.5 mg COM compared to pooled placebo in accordance with the present technology.
Figure 25:
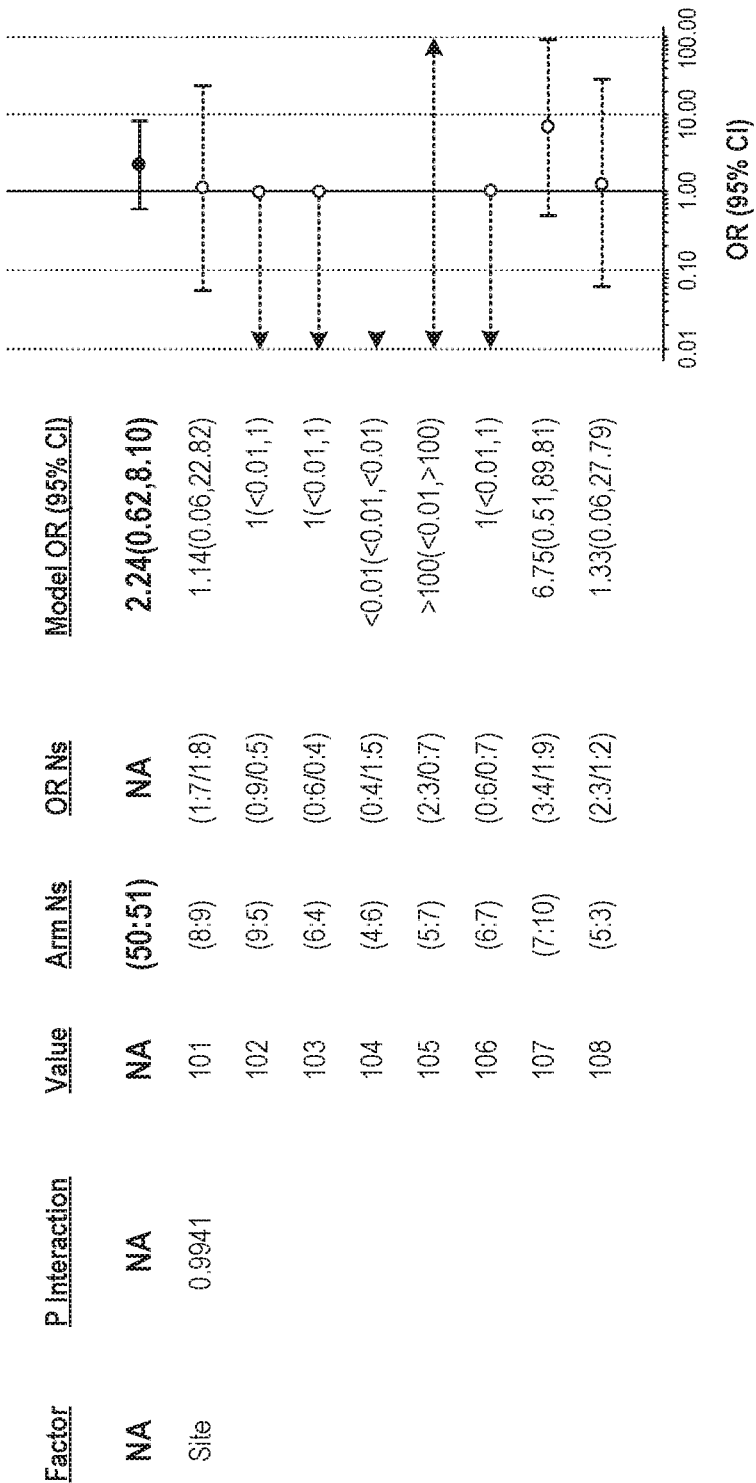
FIG. 25 is a representative plot depicting EMAs for continued 4-week abstinence through Week 5 to Week 8, confirmed by expired CO of <10 ppm (Cess/W5-8/CO Success) across clinical sites for cytisine 3.0 mg COM compared to pooled placebo in accordance with the present technology.

FIG. 16 and FIG. 17 are additional assessments for BMI and baseline mean number of cigarettes interactions specifically for the 3.0 mg TID arm compared to the pooled placebo arm.

For BMI, this assessment for the existence of an interaction with arm was evaluated as an EMA using BMI as the factor, where the size of the interaction P would be informative of the existence of this interaction (FIG. 16). The EMA interaction P value for BMI was 0.1303, not small enough to induce concern, but based on the stratum-specific effect size estimates there was a suggestion of possibly more efficacy for high BMI patients as compared to lower BMI subjects.

Evidence of an interaction between arm and the baseline mean number of cigarettes (model covariate) was assessed by the parallelism between the arms of the straight-line relationships between the Cigarette Score and the baseline mean number of cigarettes. The P value for this assessment of parallelism as shown in the scatter graph (FIG. 17) was 0.2754, providing no evidence of the absence of parallelism.

Alternative Cigarette Score Analyses

The primary outcome was based on the number of cigarettes smoked on each day from a diary. The Cigarette Score used the diary data for the planned 25 days while on study treatment. Presented are sensitivity analyses for the comparison of the 3.0 mg TID arm and the pooled placebo arm related to variations on the primary analysis of Cigarette Score. The alternative definition of the Cigarette Score featured cigarettes recorded in the diary after the planned quit period of Days 5-7, that is, from Day 8 onward, instead of from Day 1 onward.

Another alterative analysis was based on re-analyses of the primary Cigarette Score and the above alternative Cigarette Score, with a weight related to the standard error of the mean number of cigarettes estimated from the diary entries. The weight used for each subject was $1/(SE)^2$, where SE is the standard error of the mean estimate, and this type of weighting, referred to as inverse variance weighting, is used commonly. This weighting gives greater weight to means that are estimated with a smaller SE. A small modification to this definition of weight was necessary, however. In computing $1/(SE)^2$, a specific rule was used when SE=0, specifically when all diary entry values were equal. In these cases, the SE was computed as if one and only one of the recorded values was larger by one. It can be shown that when this modification to the data is made SE=1/N, where N is the number of the subjects daily (days) entries.

Table 7 shows the P values and effect estimates with 95% confidence interval for the four analyses described for the comparison of the 3.0 mg TID arm to the pooled placebo arm. When the diary data start was Day 8 instead of Day 1, the effect estimate is somewhat more favorable (−11.8 versus −9.5, respectively, for the primary Cigarette Score) because smoking data prior to the planned quit day were excluded. For the analyses where weighting was applied to the primary Cigarette Score, the effect estimate P value was 0.0466 compared to 0.0675 for the unweighted analysis of the primary Cigarette Score. This was because diary data prior to the planned quit day (prior to Day 8) followed by quitting resulted in larger SEs, thereby decreasing the weight for quitters. This decrease in weighting does not apply to the re-defined Cigarette Score using diary data starting at Day 8, and therefore the weighted effect size of the re-defined Cigarette Score was distinctly more favorable than compared to the unweighted primary Cigarette Score starting on Day 1 (−15.0 versus −9.5, respectively).

TABLE 7

P Values and Effective Estimates

| Weighted analysis as defined | Diary start day of outcome Cigarette Score analyzed | P value (3.0 mg TID versus pooled placebo) | Effect estimate (95% confidence interval) |
|---|---|---|---|
| No | Start of intervention (primary outcome) | 0.0466 | −9.5 (−18.8, −0.2) |
| | Quit Day (8th day after start of intervention) | 0.0326 | −11.8 (−22.5, −1.0) |

TABLE 7-continued

P Values and Effective Estimates

| Weighted analysis as defined | Diary start day of outcome Cigarette Score analyzed | P value (3.0 mg TID versus pooled placebo) | Effect estimate (95% confidence interval) |
|---|---|---|---|
| Yes | Start of Intervention | 0.0675 | −11.8 (−24.4, 0.9) |
|  | Quit Day (8th day after start of intervention) | 0.0006 | −15.0 (−23.3, −6.7) |

The analysis of whether there was evidence of effect heterogeneity across the 8 clinical sites (subject sources) was done as an EMA where the interaction P value provided a measure of heterogeneity of effect. This analysis was done for both the Cigarette Score primary outcome variable and Cess/W5-8/CO Success. For the Cigarette Score, the EMA model has additional covariates for BMI stratification and the mean number of cigarettes reported by screening diary. For Cess/W5-8/CO Success, no covariates were added to the EMA model due to the likelihood of empty cells in the cross classification over the discrete variables of binary outcome, arm, and clinical sites. For example, there were situations where a specific clinical site had no subjects with success in one or both arms.

FIGS. 18-25 provide EMA analysis results for each of the four comparisons of active cytisine arms to the pooled placebo arm, and for both outcome variables. No evidence of effect heterogeneity due to clinical site was found from any of these EMAs, that is, the interaction P values are not small enough to induce concern regarding clinical site heterogeneity.

1.5 Comparison of Quit Rates for Cytisinicline and Chantix®

FIG. 12 and Table 8 show the study design for comparing cytisinicline (cytisine) and Chantix®. The treatment duration of Chantix® (12 weeks) was approximately 3.5 times longer than that of cytisinicline (25 days). The sustained abstinence timepoint of Chantix® (12 weeks measured over last 4 week on treatment) was longer than the that of cytisinicline (8 weeks measured over 4 weeks after end of treatment). Table 8 includes additional details regarding trials with cytisinicline and Chantix®.

TABLE 8

Study Details for Comparing Cytisinicline and Chantix ®

|  | ORCA-1 |  | Chantix ® |  |
|---|---|---|---|---|
| Number of subjects |  |  |  |  |
|  | 1.5 mg titration | 51 | EAGLES |  |
|  | 3.0 mg titration | 50 | Chantix ® | 1005 |
|  | 1.5 mg TID | 52 | Placebo | 1009 |
|  | 3.0 mg TID | 50 | ONCKEN |  |
|  | Placebo | 51 | Chantix ® | 130 |
|  |  |  | Placebo | 129 |
| Duration of Treatment | 25 Days |  | 12 weeks |  |
| Frequent doctor visits & Behavioral support | ✓ |  | ✓ |  |
| Biochemical confirmation Quit Rates | Exhaled CO |  | Exhaled CO |  |
| 4 Weeks | ✓ |  | ✓ (ONCKEN) |  |
| End of Treatment | 4 weeks |  | 12 weeks (EAGLES) |  |
| 8 Weeks Sustained quit (4 weeks after treatment) | ✓ |  | ✓ (EAGLES) |  |

Figure 13:
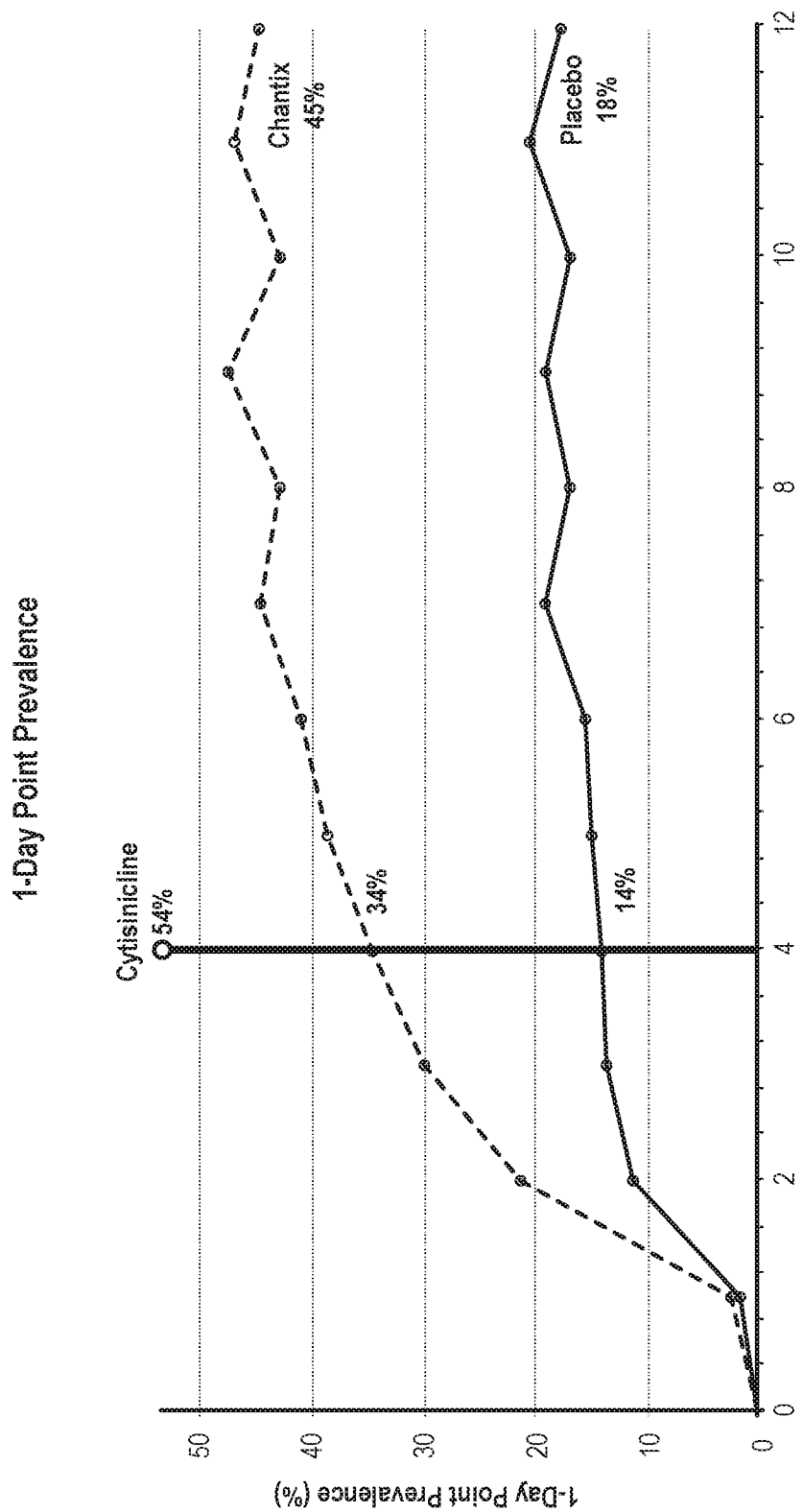
FIG. 13 is a representative graph depicting the CO confirmed quit rates between 3.0 mg of cytisinicline and 3.0 mg of Chantix® at 4 weeks and at 12 weeks of treatment in accordance with the present technology.

FIG. 13 shows the CO confirmed quit rates between 3.0 mg of cytisinicline and 3.0 mg of Chantix® at 4 weeks and at 12 weeks of treatment. Chantix® data is 7-day point prevalence, whereas cytisinicline is 1-day point prevalence. The CO-confirmed end of treatment quit rate for subjects treated with 3.0 mg of cytisinicline exceeded that of subjects treated with 3.0 mg of Chantix® at both Week 4 and Week 12 (end of Chantix® treatment). Cytisinicline had a greater efficacy compared to Chantix®.

Figure 14:
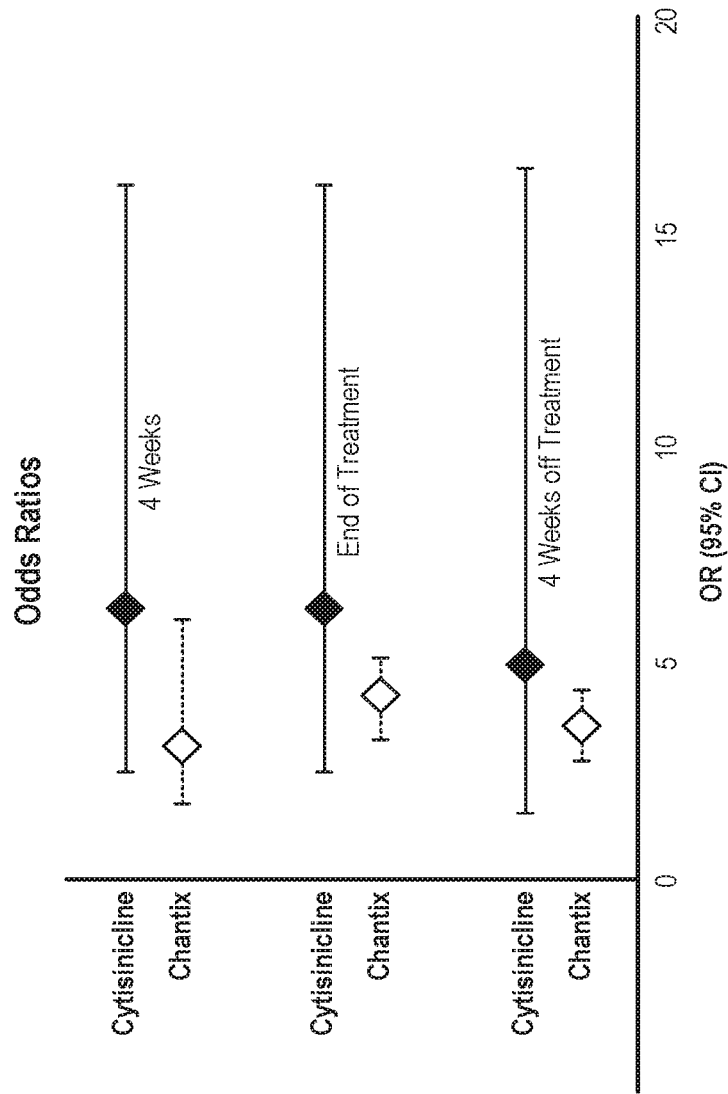
FIG. 14 is a representative plot comparing the odds ratio of cytisinicline and Chantix® at 4 weeks, end of treatment, and 4 weeks off treatment in accordance with the present technology.

FIG. 14 and Tables 9-11 show the odds ratio of cytisinicline and Chantix® at 4 weeks, end of treatment, and 4 weeks off treatment. Cytisinicline and Chantix® have similar odd ratios and efficacy. While the 95% CI of both treatments overlap, the odd ratios of the cytisinicline treatment are consistently better than that of Chantix®.

TABLE 9

Odd Ratios of Cytisinicline and Chantix ® at End of Treatment

|  | Cytisinicline | Placebo | Chantix ® | Placebo |
|---|---|---|---|---|
| Quit Rate | 54.0% | 15.7% | 38.0% | 13.7% |
| Drug-placebo difference | 38.3% |  | 24.3% |  |
| OR | 6.3 |  | 4.0 |  |
| Lower CI$_{95\%}$ | 2.47 |  | 3.20 |  |
| Upper CI$_{95\%}$ | 16.11 |  | 5.0 |  |

TABLE 10

Odd Ratios of Cytisinicline and Chantix ® at 4 Weeks Treatment

|  | Cytisinicline | Placebo | Chantix ® | Placebo |
|---|---|---|---|---|
| Quit Rate | 54.0% | 15.7% | 37.7% | 16.3% |
| Drug-placebo difference | 38.3% |  | 21.4% |  |
| OR | 6.3 |  | 3.1 |  |
| Lower CI$_{95\%}$ | 2.47 |  | 1.73 |  |
| Upper CI$_{95\%}$ | 16.11 |  | 5.99 |  |

TABLE 11

Odd Ratios of Cytisinicline and Chantix ® at 4 Weeks Off Treatment

|  | Cytisinicline | Placebo | Chantix ® | Placebo |
|---|---|---|---|---|
| Quit Rate | 30.0% | 7.8% | 33.2% | 12.5% |
| Drug-placebo difference | 22.2% |  | 20.7% |  |
| OR | 5.0 |  | 3.5 |  |
| Lower CI$_{95\%}$ | 1.54 |  | 2.78 |  |
| Upper CI$_{95\%}$ | 16.50 |  | 4.38 |  |

Table 12 shows a recent EAGLES study published in 2018 comparing quit rates in the U.S. compared to non-U.S. regions. This study notes significantly lower quit rates in the U.S. versus non-U.S. regions. The overall quit rate of 22% at 24 weeks for subjects treated with Chantix® was only 16% for U.S. patients (N=1065). The quit rates are significantly lower than previous trials with Chantix® that were all U.S.-based. The 24-week quit rates in the EAGLES study were lower than 52-week quit rates in pivotal trials. The outcomes for abstinence associated with younger ages of initial smoking and with U.S. origins were poor.

TABLE 12

Quit Rates in USA versus Non-USA

| Covariate | Varenicline | | Placebo |
| --- | --- | --- | --- |
| | CAR weeks 9-24 % (95% CI) | Versus placebo OR (95% CI) | CAR weeks 9-24 % (95% CI) |
| Region | | | |
| U.S. | 16.1 (14.0-18.4) | 2.66 (1.99-3.55) | 6.7 (5.3-8.4) |
| Non-U.S. | 27.9 (25.2-30.8) | 2.80 (2.20-3.55) | 12.2 (10.2-14.4) |

Figure 15:
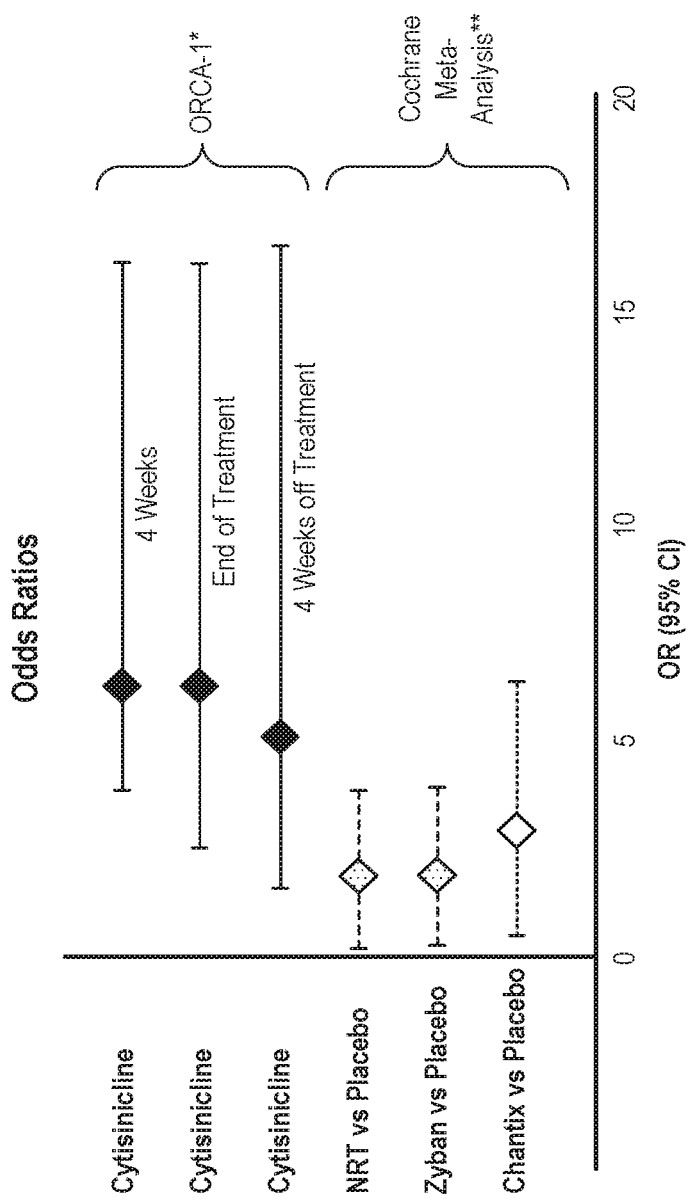
FIG. 15 is a representative plot comparing the odds ratio of cytisinicline at 4 weeks, end of treatment, and 4 weeks off treatment to current products in accordance with the present technology.

FIG. 15 shows the odds ratio of cytisinicline at 4 weeks, end of treatment, and 4 weeks off treatment compared to current products. While the 94% CI of the treatments marginally overlap, the odd ratios of the cytisinicline treatment are consistently better than that of NRT, Zyban®, and Chantix®.

1.6 Analysis of Baseline Attributes and Smoking Status

Effect Modification Analysis of Baseline Patient Attributes

Figure 26:
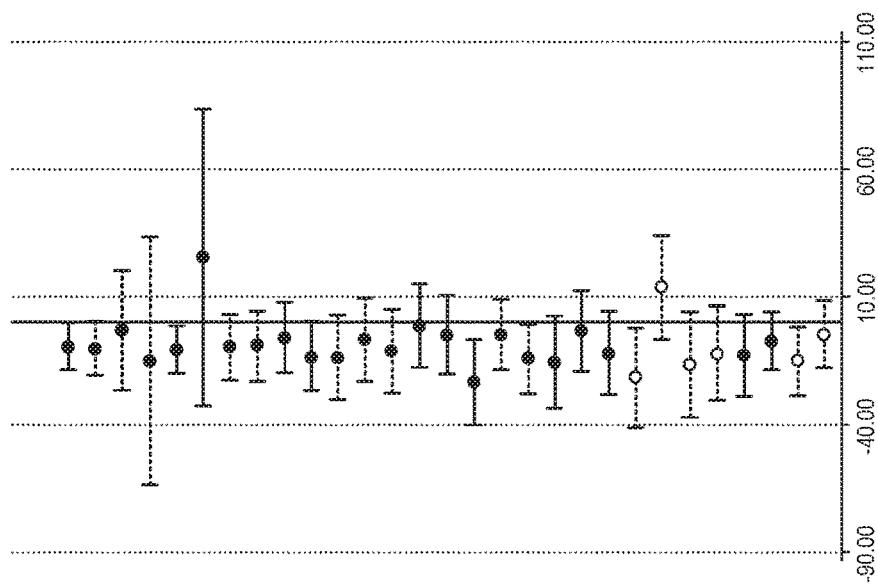
FIG. 26 is a representative plot depicting EMAs for Cigarette Score across baseline (race, Hispanic, sex, age (M), age (T), strat BMI, smoke Hx Dur (y) (M), smoke Hx Dur (y) (T), smoke Hx Dur (y) (Q), >2 Quit Hx, Screen Mean Cigs/d (M)) attributes for cytisine 3.0 mg TID compared to pooled placebo in accordance with the present technology.
Figure 27:
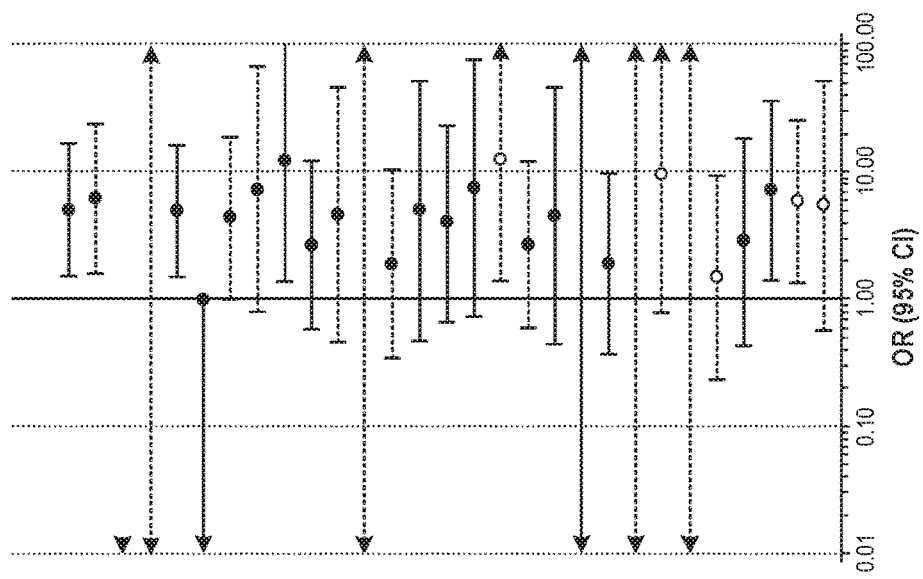
FIG. 27 is a representative plot depicting EMAs for continued 4-week abstinence through Week 5 to Week 8, confirmed by expired CO of <10 ppm (Cess/W5-8/CO Success) across baseline attributes (race, Hispanic, sex, age (M), age (T), strat BMI, smoke Hx Dur (y) (M), smoke Hx Dur (y) (T), smoke Hx Dur (y) (Q), >2 Quit Hx, Screen Mean Cigs/d (M)) for cytisine 3.0 mg TID compared to pooled placebo in accordance with the present technology.

A collection of baseline attributes including age, race, sex, duration of smoking, and number of quit attempts, were analyzed for both the Cigarette Score primary outcome variable and Cess/W5-8/CO Success (FIGS. 26 and 27). Only the comparison between the cytisine 3.0 mg TID arm and the pooled placebo arm are presented. The same EMA models used for analyzing clinical sites were used. The forest graphs for these analyses follow. (Note: In these forest graphs a (M), (T), or (Q) at the end of a factor label indicates that the pooled data were split by the median, tertiles, or quartiles, respectively. Hx denotes "History".)

The only interaction P value of note was that for the duration of smoking history split by quartiles ("Smoke Hx Dur (y) (Q)") for the Cigarette Score, with P=0.0800. Since the other smoking history duration variables did not have significant P values (P≥0.2566) this finding was regarded as unimportant. None of the other factors raised concern about heterogeneity of effect.

Effect Modification Analysis of History for Anti-Smoking Interventions

Figure 28:
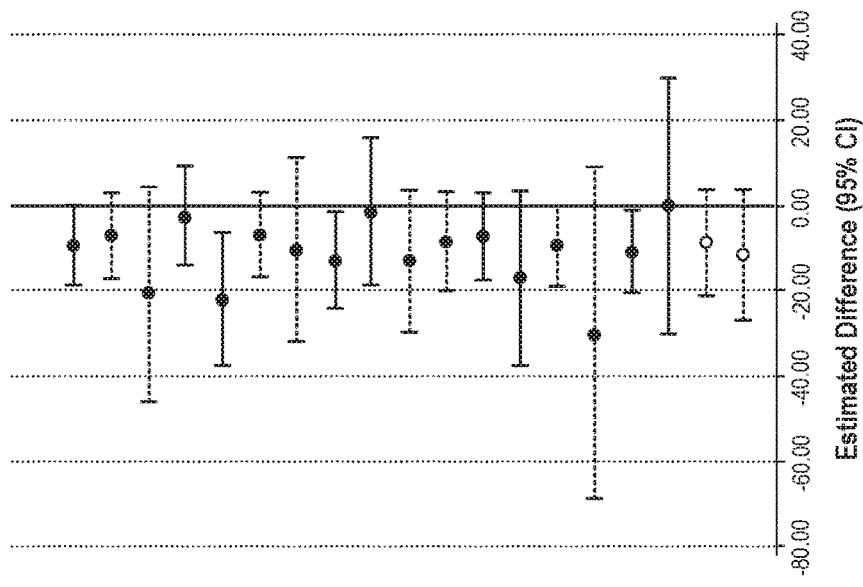
FIG. 28 is a representative plot depicting EMAs for Cigarette Score across prior anti-smoking interventions (>2 Quit Tx, Chantix® Hx, Zyban® Hx, Vape Hx, NRT Hx, Chantix® (most recent), Zyban® (most recent), Vape (most recent), and NRT (most recent) for cytisine 3.0 mg TID) compared to pooled placebo in accordance with the present technology.
Figure 29:
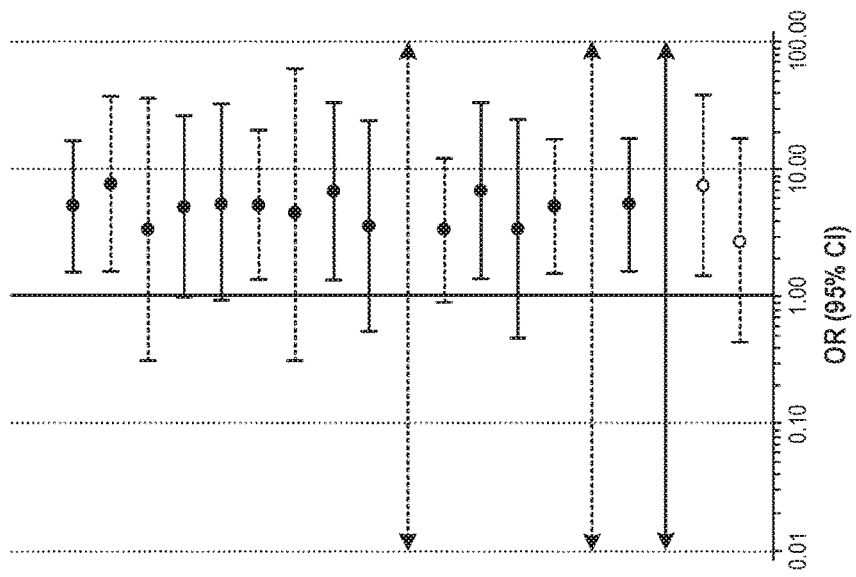
FIG. 29 is a representative plot depicting EMAs for continued 4-week abstinence through Week 5 to Week 8, confirmed by expired CO of <10 ppm (Cess/W5-8/CO Success) across prior anti-smoking interventions (>2 Quit Tx, Chantix® Hx, Zyban® Hx, Vape Hx, NRT Hx, Chantix® (most recent), Zyban® (most recent), Vape (most recent), and NRT (most recent)) for cytisine 3.0 mg TID compared to pooled placebo in accordance with the present technology.

Prior anti-smoking intervention factors were analyzed for the Cigarette Score primary outcome variable and Cess/W5-8/CO Success comparing the cytisine 3.0 mg TID arm to the pooled placebo arm (FIGS. 28 and 29). The factors analyzed include: whether more than 2 anti-smoking intervention attempts, and if ever treated or recently treated with any of Chantix®, Zyban®, vaping, or nicotine replacement therapy. The same EMA models used for analyzing clinical sites were performed. The forest graphs for these analyses follow.

The only interaction P value of note was that for history of prior use of Chantix® ("Chantix® Hx") for the Cigarette Score, with P=0.0508. However, the interaction P value for the factor variable indicating Chantix® as the most recent intervention ("Chantix® Most Recent") did not indicate concern (P=0.3179). Since the interaction appeared to be quantitative and the finding for most recent use was discordant, the concern for Chantix® being an effect modifier was discounted.

Effect Modification Analysis of Baseline Laboratory Markers Related to Smoking

Figure 30:
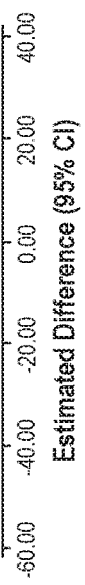
FIG. 30 is a representative plot depicting EMAs for Cigarette Score across baseline laboratory markers (NMR, CO, cotinine) for cytisine 3.0 mg TID compared to pooled placebo in accordance with the present technology.
Figure 31:
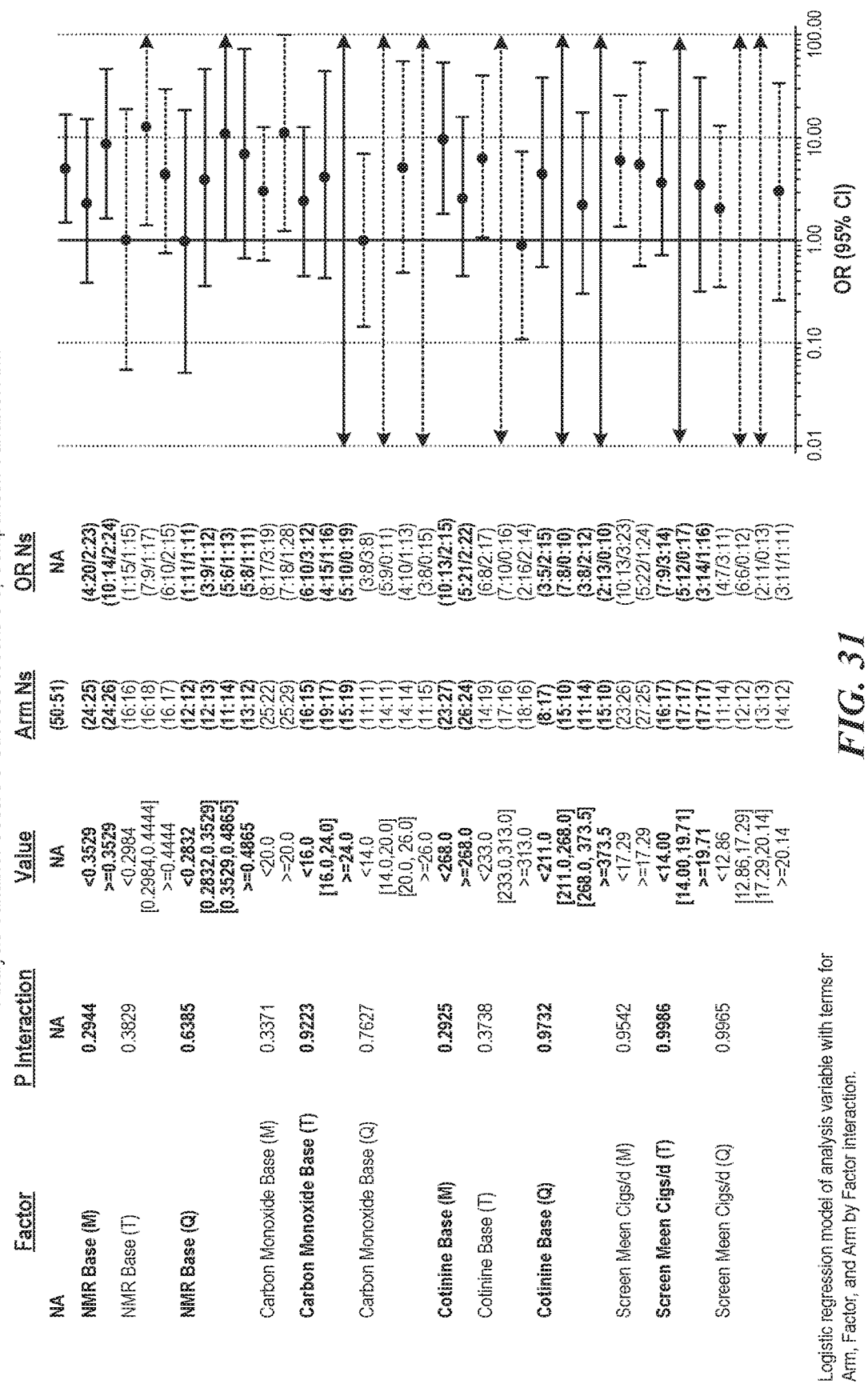
FIG. 31 is a representative plot depicting EMAs for continued 4-week abstinence through Week 5 to Week 8, confirmed by expired CO of <10 ppm (Cess/W5-8/CO Success) across baseline laboratory markers (NMR, CO, cotinine) for cytisine 3.0 mg TID compared to pooled placebo in accordance with the present technology.

Baseline laboratory factors were analyzed for the Cigarette Score primary outcome variable and Cess/W5-8/CO Success comparing the cytisine 3.0 mg TID arm to the pooled placebo arm (FIGS. 30 and 31). These factors included nicotine metabolism ratio (NMR), expired CO, and serum cotinine, and were analyzed by median, tertiles, and quartiles. The same EMA models used for analyzing clinical sites were performed. The forest graphs for these analyses follow in FIG. 30 and FIG. 31. (Note: In these forest graphs a (M), (T), or (Q) at the end of a factor label indicates that the pooled data were split by the median, tertiles, or quartiles, respectively.)

Only the interaction P values of 0.0434 and 0.0652 for the median and tertile splits of baseline cotinine, respectively, for the Cigarette Score met the criterion suggesting effect modification. However, the interaction P values for the continued abstinence secondary outcome were 0.2925, 0.3738, and 0.9732 for the median, tertile, and quartile splits, respectively, showing no effect modification regarding baseline cotinine levels. Since 4-week abstinence is planned to be the primary outcome for future Phase 3 studies, concern for baseline cotinine as an effect modifier is of less concern.

1.7 Tipping Point Analysis for Smoking Cessation Weeks 5-8

Figure 32:
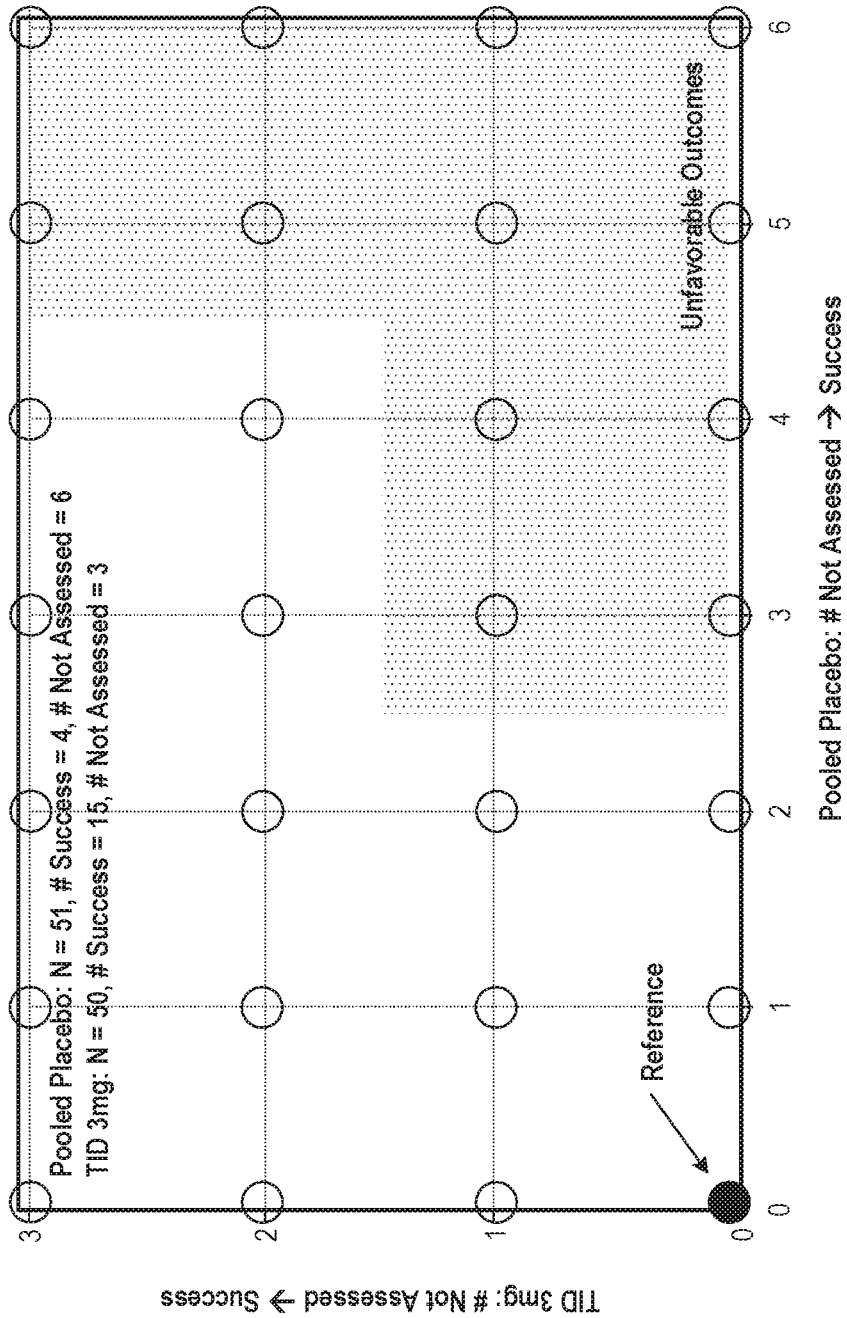
FIG. 32 is a representative graph depicting tipping point analysis for continued 4-week abstinence through Week 5 to Week 8, confirmed by expired CO of <10 ppm (Cess/W5-8/CO Success) for cytisine 3.0 mg TID arm compared to the pooled placebo arm in accordance with the present technology.

A tipping point analysis was performed for Cess/W5-8/CO Success for the cytisine 3.0 mg TID arm versus the pooled placebo arm comparison and is shown in FIG. 32. The goal of the tipping point analysis was to assess the degree to which the re-assignment of cases defined as failure due to inadequacy of assessment data would influence results. The tipping point evaluation re-analyzed the data for all possible reversals of the failure assignment to a success, with a graph illustrating which re-assignments met statistical criterion. The horizontal axis represents the number of possible control arm re-assignments and the vertical axis represents the number of possible experimental arm re-assignments. Each combination of re-assignment was re-analyzed to assess whether the statistical criterion was met. The lower left point represents the case where there are no re-assignments (that is, the planned analysis). The region where re-assignments met statistical criterion is patterned, whereas the region where re-assignments do not meet statistical criterion is grey.

There were 6 control arm cases and 3 experimental arm cases that were eligible for re-assignment. The most important finding from this graph is that if there either are 0 or 1 re-assignments in the experimental arm, then the statistical criterion will not be met when there are 3 or more re-assignments in the control arm. Similarly, if there either are 2 or 3 re-assignments in the experimental arm, then the statistical criterion will not be met when there are 5 or more re-assignments in the control arm. Thus, the continued abstinence secondary outcome was robust against re-assignments.

In summary, results for an initial quit rate at Week 4 for all cytisine-treated arms demonstrated significantly increased initial rates (50% to 54%) compared with pooled placebo (16%), and with ORs ranging from 5.38 to 6.31. Prolonged abstinence from Weeks 5 to 8 (i.e., for 4 weeks off treatment) also demonstrated significantly increased prolonged quit rates of 16% to 30% in the cytisine-treated arms compared to 8% for pooled placebo and with ORs ranging from 3.23 to 5.04. Overall, the initial and prolonged quit rates were highest for the 3.0 mg TID arm at 54% and 30%, respectively, and with the greatest ORs of 6.31 and 5.04, respectively.

Safety Analysis

Overall, there were no safety concerns following dosing in the 1.5 mg of cytisine or 3.0 mg treatment arms on both schedules, and no new or unexpected AEs were identified during the study.

Table 13 summarizes the treatment emergent adverse events (TEAEs). TEAEs were experienced by approximately half the study population in all treatment arms. The TID dosing schedule had slightly fewer TEAEs overall. Across both schedules, the SOCs with the highest incidence of TEAEs in any treatment arm were infections and infestations, psychiatric disorders, and gastrointestinal disorders. Common TEAEs were AEs that had been previously reported in other studies or within the Investigator's Brochure. All TEAEs were mild or moderate in severity on the commercial schedule and all events except 2 were mild or moderate on the TID schedule: One experienced a severe head injury, and another subject experienced a severe case of influenza. Neither event was considered related to the study drug.

events. The results from the study further demonstrate that there were no clinically-significant changes in vital signs, routine hematology and/or chemistry, and no changes in ECG. Overall, no new safety signals were observed during the conduct of this study.

CONCLUSION

The results from the study indicated that cytisine benefit occurred all baseline characteristics and attributes. In specific, the cytisine benefit occurred across subject demographics, baseline CO levels and the number of cigarettes smoked daily, as well as based on smoking history. In terms of subject demographics, the benefit was consistent across the subject population regardless of race, gender, age, and BMI. In addition, in terms of smoking history, regardless of the duration of smoking, quit attempts, and history of prior smoking cessation medication use (e.g., Chantix®, Zyban®, NRT, vaping), the subjects exhibited the same benefit from administration of cytisine.

TABLE 13

Summary of the TEAEs in the Study Population

|  | TID | | Downward Titration | | Pooled | |
| --- | --- | --- | --- | --- | --- | --- |
|  | 1.5 mg (n = 52) | 3.0 mg (n = 50) | 1.5 mg (n = 51) | 3.0 mg (n = 50) | Cytisinicline (n = 203) | Placebo (n = 51) |
| At least 1 AE | 20 (39%) | 21 (42%) | 29 (57%) | 23 (46%) | 93 (46%) | 24 (47%) |
| URTI | 5 (10%) | 3 (6%) | 3 (6%) | 2 (4%) | 13 (6%) | 7 (14%) |
| Abnormal dreams | 4 (8%) | 3 (6%) | 4 (8%) | 7 (14%) | 18 (9%) | 1 (2%) |
| Nausea | 1 (2%) | 3 (6%) | 5 (10%) | 3 (6%) | 12 (6%) | 5 (10%) |
| Insomnia | 4 (8%) | 3 (6%) | 3 (6%) | 4 (8%) | 14 (7%) | 1 (2%) |
| Headache | 6 (12%) | 2 (4%) | 1 (2%) | 1 (2%) | 10 (5%) | 2 (4%) |
| Fatigue | 3 (6%) | 1 (2%) | 1 (2%) | 2 (4%) | 7 (3%) | 2 (4%) |
| Constipation | 1 (2%) | 3 (6%) | — | — | 4 (2%) | 1 (2%) |

*≥5% (3 subjects) in any treatment arm

There were no relevant mean changes or shifts from baseline in laboratory parameters over time or 12-lead ECG results. The overall incidence of potentially clinically significant changes in vital sign measurements was low, with the lowest incidence occurring on the TID schedule.

Table 14 summarizes the TEAEs of cytisinicline compared to Chantix® in a previous 2016 study. TEAEs were experienced by less than 30% the study population treated with either cytisinicline, Chantix®, or placebo. Subjects treated with Chantix® experienced the highest incidence of TEAEs compared to cytisinicline and placebo. Most incidences of TEAEs with cytisinicline treatment was only marginally higher than placebo.

TABLE 14

TEAEs of cytisinicline compared to Chantix ® in 2016 Study

|  | ORCA-1 | | Cochrane |
| --- | --- | --- | --- |
|  | Cytisinicline (n = 203) | Placebo (n = 51) | Chantix ® (n > 7000) |
| Serious AEs | 0 | 0 | 3.3% |
| Abnormal dreams | 18 (9%) | 1 (2%) | 12.5% |
| Headache | 10 (5%) | 2 (4%) | 12.7% |
| Insomnia | 14 (7%) | 1 (2%) | 14.2% |
| Nausea | 12 (6%) | 5 (10%) | 27.8% |

In summary, there were no serious or severe adverse events and there was a low incidence of overall adverse The results further demonstrated that subjects exhibited a similar benefit upon administration of cytisine irrespective of their ability to metabolize nicotine. In particular, no treatment relationship was observed based on the baseline nicotine metabolite ratio of the subjects and there was a similar cytisine benefit for fast and slow nicotine metabolizers.

Results from the primary analyses demonstrated a reduction in percentage of expected cigarettes smoked in both schedules versus pooled placebo. Results for the initial quit rate endpoint demonstrated both cytisine arms of the TID schedule had high odds of success compared with placebo; subjects in the 3.0 mg of cytisine arm had the best odds of success for quitting smoking at Week 4.

For the prolonged abstinence from Week 5 to Week 8 endpoint, both arms of the TID schedule had high odds of success compared with placebo; subjects in the 3.0 mg of cytisine arm had the best odds of success for abstinence from Weeks 5 to 8. The study demonstrated that cytisine is an effective aid to smoking cessation with an advantageous adverse event profile, and 3.0 mg TID dosing is more efficacious overall, with no increase in adverse events.

Overall, there were no safety concerns following dosing in the 1.5 mg of cytisine or 3.0 mg arms on either schedule.

Example 2: Impact of Continued Treatment with Cytisine on Smoking Cessation

Figure 33:
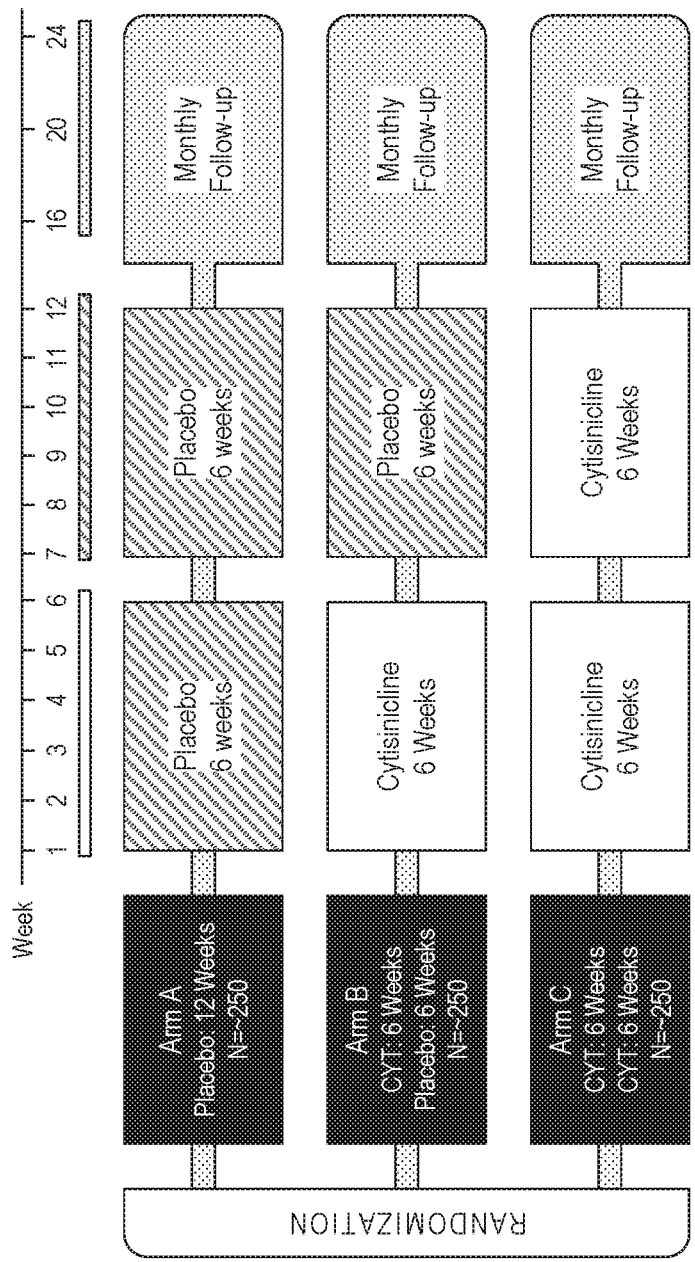
FIG. 33 is a schematic of the study design of Example 2 in accordance with the present technology.

This Example describes a Phase 3, multi-center, double-blind, randomized, placebo-controlled trial designed to evaluate the efficacy and safety of cytisine in adult smokers. This study is designed to improve efficacy outcomes and to determine whether continued treatment can prevent early smoking relapse. The study is designed to evaluate treatment across 3 treatment arms: placebo (A), treatment with cytisine (e.g., cytisinicline) for 6 weeks (B), and treatment with cytisine for 12 weeks (C) as shown in the schematic of FIG. 33. Subjects are randomized to one of the three arms A, B, or C. In Arm A, subjects are treated with a placebo for 12 weeks plus behavioral support. In Arm B, subjects are treated with 3.0 mg cytisinicline TID for 6 weeks followed by a placebo for 6 weeks plus behavioral support. In Arm C, subjects are treated with 3.0 mg cytisinicline TID for 12 weeks plus behavioral support. Cytisine treatment will be evaluated in the study population for 6 or 12 weeks, with a primary efficacy endpoint of 4-weeks of continuous abstinence while on treatment and will include a 6-month follow-up period.

2.1 Study Objectives 2.1.1 Co-Primary Efficacy Objectives

The co-primary efficacy objectives of the study, which will be based on two comparisons where study success can be based on success for either comparison, will be the following:

To assess whether subjects randomized to Arm B have a higher probability of abstinence from Week 3 to Week 6 post-randomization as compared to subjects randomized to Arm A; and To assess whether subjects randomized to Arm C have a higher probability of abstinence from Week 9 to Week 12 post-randomization as compared to subjects randomized to Arm A.

2.1.2 Secondary Efficacy Objectives

If the corresponding primary comparison passes statistical criterion, then analysis for the following secondary objectives will be performed. The secondary efficacy objectives of the study will be the following:

To assess whether subjects randomized to Arm B have a higher probability of continuous abstinence from Week 6 to Week 24 post-randomization as compared to subjects randomized to Arm A; and To assess whether subjects randomized to Arm C have a higher probability of continuous abstinence from Week 12 to Week 24 post-randomization as compared to subjects randomized to Arm A.

If the co-primary comparisons pass statistical criterion, then analysis for the following additional secondary objective will be performed. The additional secondary efficacy objective of the study will be the following:

To assess for a reduction in risk of relapse from Week 6 to Week 24 in subjects receiving 3.0 mg cytisinicline for 6 weeks and then either continue 3.0 mg cytisinicline from Week 6 to Week 12 (Arm C) or were switched to placebo from Week 6 to Week 12 (Arm B). Subjects not abstinent at Week 6 will be regarded as having relapsed.

2.1.3 Other Objectives

Other objectives of this study will be the following:

To compare arms (Arm B versus Arm A; Arm C versus Arm A) on 7-day point prevalence abstinence weekly at Week 2 to Week 12, then for Weeks 16, 20, and 24;

To compare arms (Arm B versus Arm A; Arm C versus Arm A) on serum cotinine levels every other week at Week 2 to Week 12, then at Weeks 16, 20, and 24;

To compare arms (Arm B versus Arm A; Arm C versus Arm A) on expired CO levels every week at Week 2 through Week 12, then at Weeks 16, 20, and 24;

To compare arms (Arm B versus Arm A; Arm C versus Arm A) on use of any non-cigarette nicotine products, including vaping, during study treatment at Week 2 through Week 12 and study follow-up at Week 16 through Week 24;

To assess whether subjects randomized to Arm B have a higher probability of abstinence from Week 9 to Week 12 as compared to subjects randomized to Arm A (placebo);

To assess among the subset of subjects who achieve abstinence from Week 3 to Week 6, whether subjects randomized to Arm B have a higher probability of continuous abstinence from Week 3 to Week 24 post-randomization as compared to subjects randomized to Arm A;

To assess among the subset of subjects who achieve abstinence from Week 9 to Week 12, whether subjects randomized to Arm C have a higher probability of continuous abstinence from Week 9 to Week 24 post-randomization as compared to subjects randomized to Arm A;

Among subjects who achieve abstinence from Week 3 to Week 6, to compare time to failure to maintain abstinence between arms (Arm B versus Arm A; Arm C versus Arm A) to Week 24;

To explore the magnitude of treatment effect between arms across various subgroups defined by demographic and baseline characteristics for the primary and secondary outcomes; and To explore potential relationships between subject-reported outcomes (e.g., anxiety, depression, withdrawal symptoms, and tobacco craving) and the primary and secondary outcomes.

2.1.4 Safety Objectives

The safety objectives of the study will be the following:

To evaluate the safety profile of 3.0 mg TID cytisinicline compared to placebo (e.g., Arm B versus Arm A and Arm C versus Arm A);

To compare the safety profiles of Arm B subjects versus Arm C subjects with respect to adverse events occurring after Week 6 on the study.

2.2 Study Design

The population for this study will be male or female adults who are daily cigarette smokers, intending to quit smoking, and are willing to set a quit date that is within 5 to 7 days of the start of treatment. Study treatment will start the day after randomization.

Subjects will meet all requirements outlined in inclusion and exclusion criteria. A total of approximately 750 subjects will be randomly assigned with equal probability to one of three Arms (Arm A, 12 weeks placebo: N=250; Arm B, 6 weeks cytisinicline followed by 6 weeks placebo: N=250; Arm C, 12 weeks of cytisinicline: N=250) as shown in FIG. 33.

Each randomized subject will receive 12 weeks of treatment using a TID dosing schedule. Smoking cessation assessments will begin on Week 2 (Day 14±1 post-randomization) and will continue weekly during the Treatment Period through the Week 16, 20, and 24 Follow-up Period visits by the subject's self-report of abstinence with CO biochemical verification.

All subjects will receive concurrent smoking cessation behavioral support during the study Treatment Period (Week 1-12). Additional behavioral support will be provided during the Follow-up Period based on issues, concerns, and/or questions raised by the subject.

Safety assessments at clinic visits will occur on Day 2 and Day 7 during Week 1 and then weekly throughout the Treatment Period. Laboratory hematology and chemistry assessments will be made on Day 7, Week 6, and Week 12 (End of Treatment "EOT") during the Treatment Period. Any ongoing adverse events at Week 12 will be followed until resolved or determined to be chronic. The end of study is defined as the last follow-up visit (up to the Week 24 visit) for the last subject.

2.3 Treatment Period

The Treatment Period will begin on the day after randomization. Study treatment will be blinded, and subjects will take one study tablet three times during the day, approximately 5 hours apart. Subjects randomly assigned to Arm A will take one placebo tablet at each dosing per day for 12 weeks. Arm B subjects will take one cytisinicline tablet at each dosing per day for the first 6 weeks followed by one placebo tablet at each dosing per day for the last 6 weeks. Arm C subjects will take one cytisinicline tablet at each dosing per day for 12 weeks.

2.4. Inclusion Criteria

Subjects meeting all of the following criteria will be eligible to participate in the study:

Male or female subjects years of age.

Current daily cigarette smokers (averaging at least 10 cigarettes per day upon completing a 7-day screening smoking diary) and who intend to quit smoking.

Expired air CO ≥10 ppm.

Failed at least one previous attempt to stop smoking with or without therapeutic support.

Willing to initiate study treatment on the day after randomization and set a quit date within 5 to 7 days of starting treatment.

Willing to actively participate in the study's smoking cessation behavioral support provided throughout the study.

Able to fully understand study requirements, willing to participate, and comply with dosing schedule.

Sign the Informed Consent Form.

2.5. Exclusion Criteria

Subjects will be excluded from participation in the study if any of the following criteria apply:

More than 1 study participant in same household.

Previous cytisinicline treatment in a prior clinical study or any other cytisine usage.

Known hypersensitivity to cytisinicline or any of the excipients.

Positive urinary drugs of abuse screen determined within 28 days before the first dose of cytisinicline.

Clinically significant abnormal serum chemistry or hematology values within 28 days of randomization (i.e., requiring treatment or monitoring).

Clinically significant abnormalities in 12-lead ECG determined after minimum of 5 minutes in supine position within 28 days of randomization (i.e., requiring treatment or further assessment).

BMI classification for being underweight (<18.5 kg/m2) or having ≥Class 2 obesity (≥35 kg/m2).

Recent history (within 3 months) of acute myocardial infarction, unstable angina, stroke, cerebrovascular incident, or hospitalization for congestive heart failure.

Current uncontrolled hypertension (blood pressure ≥160/100 mmHg).

Documented diagnosis of schizophrenia or bipolar psychiatric illness; currently psychotic; having suicidal ideation/risk ("Yes" to question 4 or question 5 OR "Yes" to any suicidal behavior question on the C-SSRS); or current symptoms of moderate to severe depression (HADS score ≥1).

Renal impairment defined as a creatinine clearance (CrCl) <60 mL/min (estimated with the Cockroft-Gault equation).

Hepatic impairment defined as alanine aminotransferase (ALT) or aspartate aminotransferase (AST) >2.0× the upper limit of normal (ULN).

Women who are pregnant or breast-feeding.

Male or female subjects of child bearing potential who do not agree to use acceptable methods of birth control during the study treatment period.

Participation in a clinical study with an investigational drug in the 4 weeks prior to randomization.

Treatment with other smoking cessation medications (bupropion, varenicline, nortriptyline, or any nicotine replacement therapy [NRT]) in the 4 weeks prior to randomization or planned use of these other smoking cessation medications during the study.

Use within the 2 weeks prior to randomization or planned use during the study of non-cigarette and/or noncombustible nicotine products (pipe tobacco, cigars, snuff, smokeless tobacco, hookah, e-cigarettes/vaping) or marijuana smoking or vaping.

Any other reason that the investigator views the subject should not participate or would be unable to fulfill the requirements for the study.

2.6 Previous and Concomitant Medications

All subjects will continue to receive any existing prescription medication. Every effort will be made to ensure that the regimen of existing medications remain stable during the study.

At the discretion of the Investigator, the use of non-study drug medications (either prescription or over-the-counter) may be given if clinically-indicated during the study. Full details of any new medications will be recorded in the subject's Case Report Form (CRF).

All concomitant medication(s) taken during the trial, and any changes (additions, deletions, dose changes) will be recorded in the CRF.

2.7 Treatment Compliance

Treatment compliance will be monitored during the 84-day (12-week) Treatment Period via review of dose timing and drug accountability. Subjects will have a daily treatment diary that will record the number of tablets taken and time taken. Subjects will be instructed to bring their medication packs (blister packs) to each clinic visit so that clinic staff can reconcile against the treatment diary, recording the number of tablets taken and the number of missed tablets. In addition, an optional text messaging system will be implemented that will provide each subject with reminder texts corresponding to the approximate time of dosing.

2.8 Study Procedures

After providing signed informed consent, all subjects will be evaluated for inclusion in the study within a 28-day Screening Period. Subjects who meet inclusion criteria will be required to provide a quit date that must be within 5-7 days after the start of treatment and agree to initiating study treatment the day after randomization. Both planned quit and treatment start dates will be documented to confirm inclusion. Once all eligibility criteria are confirmed, randomization can occur. Study Day 1 will be defined as the first day of treatment. Subjects will complete a clinic visit on Day 2, 7, 14, 21, 28, 35, 42, 49, 56, 63, 70, 77, and 86. Follow-up visits will be scheduled at Week 16, 20, and 24.

2.8.1 Procedure Schedule

Table 15 provides a summary of required study evaluations. Screening evaluations will occur within a 28-day interval from initiation of screening evaluations to randomization. Subjects will initiate study treatment the day after randomization, such that study treatment is initiated on Day 1 prior to the quit date, within 5-7 days of Day 1.

TABLE 15

Schedule of Study Procedures During Treatment Period

| Study Assessment | SV 1 | SV 2[1] | Day 0 | D1[2] | D2 | W1 (D7) | W2 (D14) | W3 (D21) | W4 (D28) | W5 (D35) | W6 (D42) | W7 (D49) | W8 (D56) | W9 (D63) | W10 (D70) | W11 (D77) | EOT[3] (D86) |
|---|---|---|---|---|---|---|---|---|---|---|---|---|---|---|---|---|---|
| Informed Consent | • | | | | | | | | | | | | | | | | |
| Inclusion/Exclusion | • | | | | | | | | | | | | | | | | |
| Demographics | • | | | | | | | | | | | | | | | | |
| Medical and Psychiatric History | • | | | | | | | | | | | | | | | | |
| C-SSRS Questionnaire[4] | • | | | | | | | | | | • | | | | | | • |
| Physical Exam | •[5] | | | | | | | | | | | | | | | | |
| Smoking History | • | | | | | | | | | | | | | | | | |
| Urine Pregnancy Test for all Females[6] | • | | • | | | | | | • | | | | • | | | | • |
| Drugs of Abuse Screen[7] | • | | | | | | | | | | | | | | | | |
| Vital Signs including weight | •[8] | | • | • | • | • | • | • | • | • | • | • | • | • | • | • | • |
| Hematology and Chemistry | • | | | | | | • | | | | • | | | | | | • |
| 12-lead ECG | • | | | | | | | | | | • | | | | | | • |
| Concomitant Medications | • | • | • | • | • | • | • | • | • | • | • | • | • | • | • | • | • |
| Quit Date Set and Treatment Day 1 Scheduled | | • | | | | | | | | | | | | | | | |
| Review Smoking & Treatment Diary Completion Instructions[9] | • | | • | • | | | | | | | | | | | | | |
| Review Smoking Diary[10] | • | • | | | | | | | | | | | | | | | |
| Review Treatment Diary Entries for Completeness and Compliance[11] | | | | | • | • | • | • | • | • | • | • | • | • | • | • | • |
| Adverse Event Reporting | • | • | • | • | • | • | • | • | • | • | • | • | • | • | • | • | • |
| Study Drug Distribution, Accountability, and Collection | | | • | | • | • | • | • | • | • | • | • | • | • | • | • | • |
| Behavioral Support | | •[12] | • | | • | • | • | • | • | • | • | • | • | • | • | • | • |
| Fagerstrom Test of Nicotine Dependence | | | • | | | | | | | | | | | | | | |
| Self-Efficacy Questionnaire | | | • | | | | | | | | | | | | | | |
| QSU-Brief Questionnaire | | | • | | | • | • | • | • | • | • | • | • | | | | |
| MNWS Questionnaire[13] | | | • | | | | • | • | • | • | • | • | • | | | | |
| HADS Questionnaire | • | | | | | | | | | | | | | | | | • |
| Smoking Cessation Status | | | | | | | | | • | • | • | • | • | • | • | • | • |

TABLE 15-continued

Schedule of Study Procedures During Treatment Period

| Study Assessment | Screening Period (Day 28 to Rand) | | Randomization | Treatment Period Week 1-Week 12 (Day 84) (Days 7-86 are ±1 Day) | | | | | | | | | | | | |
|---|---|---|---|---|---|---|---|---|---|---|---|---|---|---|---|---|
| | SV 1 | SV 2[1] | Day 0 | D1[2] | D2 | W1 (D7) | W2 (D14) | W3 (D21) | W4 (D28) | W5 (D35) | W6 (D42) | W7 (D49) | W8 (D56) | W9 (D63) | W10 (D70) | W11 (D77) | EOT[3] (D86) |
| Expired CO | • | | • | | | • | • | • | • | • | • | • | • | • | • | • | • |
| Use of any non-cigarette nicotine products[14] | | | | | | • | • | • | • | • | • | • | • | • | • | • | • |
| Serum Cotinine | •[15] | | | | | • | | | • | | • | | • | | • | | • |

[1]Randomization may occur at the SV2 visit IF subject can commit to a quit date that allows start of treatment the following day. In such cases, all Day 0 (Randomization) procedures will be completed at the SV2 clinic visit.
[2]Clinic will telephone each subject towards the end of Day 1 (first day of treatment) to make sure subject has taken medication according to dosing schedule, answer any questions, assess for adverse events and any concomitant medications, and confirm the Day 2 clinic appointment.
[3]Procedures required at Day 86 or if subject discontinues treatment prior to Week 12. The final day of treatment will be on Day 84. In order to ensure subject completes all treatment prior to assessments, the End of Treatment visit will be scheduled on Day 86 ± 1 Day.
[4]The Screening assessment for suicidal ideation (questions 1-5) will be asked in the temporal context of "within the past 3 months" and the Suicidal Behavior questions will be asked within the temporal context of "within lifetime" in order to fully evaluate current ideation or risk of suicide. Assessments conducted at Week 6 and EOT will ask all questions in the temporal context of "since last assessment" for suicidal ideation/risk.
[5]Physical exam may be conducted at either the SV1 or the SV2.
[6]Urine pregnancy test kits supplied to site by central laboratory. All other testing performed by a central laboratory. Test results must be negative at the SV1 and DO visit for inclusion into the study.
[7]Drugs of abuse to include at a minimum amphetamines, methamphetamines, barbiturates, benzodiazepines, cocaine, ecstasy, opiates, and phencyclidine.
[8]To include height at screening for BMI calculation.
[9]There will be two distinct diaries to be used: The screening smoking diary will capture daily cigarette consumption for 7 consecutive days so that an average can be obtained to assess Inclusion Criteria #2. The on-study treatment diary will assess treatment compliance and will capture each study drug dose date and time.
[10]Number of cigarettes smoked daily will be recorded in a 7-day smoking diary to be completed by the subject between SV1 and SV2. Adequate completion of the 7-day screening diary with an average of at least 10 cigarettes smoked per day will be required for inclusion into the study.
[11]Study subjects will make daily diary entries noting date and time of each dose. Sites will review these prior (via on-line access) and during clinic visits to ensure subject is completing entries in real-time and accurately.
[12]Setting the quit date and plan will be considered the first behavioral support counseling session.
[13]The MNWS questionnaire to assess withdrawal will be administered to all subjects on Day 0 and Week 1 (Day 7). Subsequent measurements will only be administered for subjects that report no cigarettes smoked since the last clinic visit.
[14]Although planned use during the study is an exclusion criteria, record any actual use of non-cigarette nicotine products, including vaping.
[15]Serum will be collected with other laboratory testing at SV#1 for cotinine testing and another sample will be frozen/stored for possible Nicotine Metabolite Ratio (NMR) testing at baseline only. Serum collected on subjects that are screen-failed will be destroyed.

TABLE 16

Schedule of Procedure During Follow-up Period

| | Follow-up Period Week 16-Week 24[1] (Week Visits ±3 Days) | | |
|---|---|---|---|
| Study Assessment | Week 16 | Week 20 | Week 24 |
| Behavioral Support[2] | • | • | • |
| Adverse Event Reporting | • | • | • |
| Smoking Cessation Status | • | • | • |
| Expired CO | • | • | • |
| Use of any non-cigarette nicotine products[3] | • | • | • |
| Serum Cotinine | • | | • |

[1]All subjects regardless of smoking status at Day 84/Week 12 will continue for follow-up at the Week 16, Week 20, and Week 24 clinic visits.
[2]Behavioral support sessions during the Follow-up Period will be abbreviated and based only on issues, concerns, and/or questions raised by subject for Week 16, 20, and 24.
[3]Record any actual use of non-cigarette nicotine products, including vaping.

2.8.2 Subject Diaries

A 7-day smoking diary will be collected during the screening period in order to capture the number of cigarettes smoked daily for 7 consecutive days. This data will be used to calculate the average number of cigarettes smoked per day in order to support Inclusion Criteria #2.

In addition, a study treatment diary will be maintained by each subject to record date and timing of study drug administrations during the Treatment Period. The diary will be configured into specific sections to support the above reporting by the subject.

2.9 Efficacy Criteria

This study will follow general criteria that are applicable to previous and current trials of cessation aids where participants have a defined target quit date and there is face-to-face contact with researchers or clinic staff. Endpoint analyses for abstinence (4 weeks abstinence documented during the last 4 weeks of treatment) and continuous abstinence (continually documented to Week 24 post-randomization) will include the following criteria:

Self-report of smoking abstinence since the last clinic visit at each clinic assessment.

Biochemical verification of abstinence by expired CO at each clinic visit.

Use of an 'intention-to-treat' approach in which data from all randomized smokers will be included in the analysis.

Subjects with an unknown smoking status at the Week 6, Week 12, and Week 24 assessments or lost to follow-up will be classified as failed to quit.

Self-report of smoking abstinence during the follow-up period only (Week 12 to Week 24) will follow the Russell Standard.

Continually blinded to treatment allocation during collection of follow-up data to Week 24.

2.9.1 Safety Assessments

All subjects will be monitored for adverse events starting at screening (pre-existing), by telephone contact on Day 1, at clinic visits on Day 2 and Day 7 during Week 1, then weekly throughout the Treatment Period (Weeks 2 through 12/EOT) and monthly during the Follow-up Period (see Table 15 and Table 16). Laboratory (hematology and chemistry) evaluations will be performed at the Week 1, Week 6, and Week 12 clinic visits using a central laboratory.

Safety will be assessed by consideration of all adverse events reported by or elicited from the subject and abnormalities detected on hematology and serum chemistry tests. Worsening of other pre-existing medical conditions and any changes to concomitant medications/treatments will also be taken into account in this evaluation.

2.9.2 Laboratory
Routine Laboratory Assessments

Routine laboratory safety samples will be analyzed at screening and at clinic visits as identified in Table 15 for each subject by a central laboratory. A decision regarding whether a result outside the reference range is of clinical significance or not will be made by an Investigator, and the report will be annotated accordingly. Clinically significant abnormalities occurring during the study will be recorded on the AE page. The reference ranges for laboratory parameters will also be entered in the database and filed in the Investigator site file.

Hematology: Hemoglobin, red blood cells, white blood cells, neutrophils, lymphocytes, monocytes, eosinophils, basophils, and platelets.

Chemistry: Total protein, albumin, total bilirubin, SGPT (ALT), SGOT (AST), alkaline phosphatase, glucose, sodium, potassium, calcium, creatinine, and urea.

Expired Air CO

Expired CO will be obtained using a calibrated instrument (e.g., the Bedfont Micro+ Smokerlyzer®) provided and maintained by the clinical site. Each clinical site will have documentation of instrument used and current calibration. CO values will be reported in parts per million (ppm) at Week 2, weekly through Week 12, and at Week 16, 20, and 24.

Serum Cotinine Levels

Serum samples will be collected for determining cotinine levels at Weeks 2, 4, 6, 8, 10, 12, 16, 20, and 24. Baseline cotinine testing will use frozen serum collected at the SV1 visit for subjects that are randomized. Cotinine levels will be determined at a central laboratory.

2.9.3 Vital Signs

Systolic/diastolic blood pressure, pulse rate, and oral temperature measurements will be recorded in a seated position. Body weight will also be recorded. Height will be recorded at Screening Visit #1 for BMI calculation.

2.9.4 Physical Examination

A physical examination will be performed by an Investigator. The examination will include general appearance, head, ears, eyes, nose, throat, neck, skin, cardiovascular system, respiratory system, gastrointestinal system, central nervous system, lymph nodes, and musculoskeletal. An Investigator can examine other body systems if required, at their discretion.

2.10 Primary Outcome for Subjects

The primary efficacy outcome (biochemically verified abstinence for the last 4 weeks of cytisinicline treatment) for each subject will be binary: success versus failure. Success will be defined for the subject as having reported smoking abstinence (no cigarettes since the last clinic visit) at each clinic assessment from Week 3 to Week 6 (Arm B) and Week 9 to Week 12 (Arm C) with biochemical verification at each assessment. Biochemical verification will be defined by a carbon monoxide concentration in exhaled breath of less than 10 ppm. Similar timeframe and analyses will occur for Arm A placebo subjects.

2.11 Secondary Outcome for Subjects

The secondary efficacy outcome 1 and 2 (continued biochemically verified abstinence to Week 24) for each subject will be binary: success versus failure. Success will be defined for the subject as having reported smoking abstinence since the last clinic visit at each clinic assessment from Week 6 (Arm B) or Week 12 (Arm C) to Week 24 with biochemical verification at each assessment. Biochemical verification will be defined by a carbon monoxide concentration in exhaled breath of less than 10 ppm. During the Follow-up Smoking Cessation Assessment Period between Weeks 12 to 24, self-report of smoking abstinence will be according to the Russell Standard.

The secondary efficacy outcome 3 will be success with respect to being without relapse at Week 24. The secondary efficacy outcome 3 (reduction in risk of relapse from Week 6 to Week 24 in Arm C versus Arm B) will be assessed in each subject (in both Arms C and B). Subjects not abstinent at Week 6 will be regarded as having relapsed.

2.12 Safety Objectives

Safety assessments will include reported adverse events, laboratory test results, and vital signs. Safety variables will be summarized for the Safety Analysis Set (SAS), defined as all randomized subjects who take at least one dose of study drug.

Adverse events will be coded using the MedDRA dictionary. Coding will include system organ class (SOC) and preferred term (PT). All verbatim descriptions and coded terms will be listed for all AEs. Various embodiments of the invention are set forth herein below in paragraphs 272 to 391:

A method of treating a nicotine addiction, a nicotine dependence, promoting cessation of smoking and/or vaping, and/or promoting a reduction in smoking and/or vaping in a subject in need thereof, the method comprising administering cytisine provided in a unit dose of 3.0 mg, 1.5 mg, or 1.0 mg of cytisine three times daily to the subject.

The method of paragraph 272, wherein the subject experiences no adverse events after receiving the cytisine treatment.

The method of paragraphs 272 and 273, wherein the adverse event is selected from the group consisting of an URTI, abnormal dreams, nausea, insomnia, headache, fatigue, and constipation.

The method of paragraphs 272-274, wherein the subject experiences no nausea after receiving the cytisine treatment.

The method of paragraphs 272-275, wherein cytisine is administered for about 6 weeks or for about 12 weeks.

The method of paragraphs 272-276, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

The method of paragraphs 272-277, wherein the subject is a refractory patient who has failed treatment with one or more nicotine addiction or smoking cessation treatments.

The method of paragraphs 272-278, wherein the nicotine addiction or smoking cessation treatments are selected from NRT, administration of bupropion, administration of varenicline, electronic cigarettes, vaping, and a combination thereof.

The method of paragraphs 272-279, wherein the subject (a) smoked ten or more cigarettes per day prior to the administration of cytisine, (b) has expired air CO concentration of about 10 ppm or greater prior to the administration of cytisine, or (c) a combination of (a) and (b).

The method of paragraphs 272-280, further comprising providing behavioral support to the subject.

A method of treating of nicotine addiction and/or a nicotine dependence in a subject in need thereof, the method comprising administering cytisine to the subject, wherein the subject is a refractory patient who has failed treatment with one or more nicotine addiction treatments.

The method of paragraph 282, wherein the nicotine addiction treatments comprise NRT, administration of bupropion, administration of varenicline, electronic cigarettes, vaping, or a combination thereof.

The method of paragraphs 282 and 283, wherein cytisine is provided in a unit dose of about 1.0 mg to about 6.0 mg of cytisine three to six times daily to a subject in need thereof.

The method of paragraphs 282-284, wherein cytisine is provided in a unit dose of 3.0 mg of cytisine three times daily to a subject in need thereof.

The method of paragraphs 282-285, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

The method of paragraphs 282-286, wherein cytisine is administered for about 6 weeks or for about 12 weeks.

The method of paragraphs 282-287, wherein the subject experiences no adverse events after receiving the cytisine treatment.

The method of paragraphs 282-288, wherein the adverse event is selected from the group consisting of an URTI, abnormal dreams, nausea, insomnia, headache, fatigue, and constipation.

The method of paragraphs 282-289, wherein the subject (a) smoked ten or more cigarettes per day prior to the administration of cytisine, (b) has expired air CO concentration of about 10 ppm or greater prior to the administration of cytisine, or (c) a combination of (a) and (b).

A method of preventing smoking and/or vaping relapse in a subject in need thereof, the method comprising administering cytisine provided in a unit dose of (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, three times daily to the subject.

The method of paragraph 291, wherein cytisine is administered for about 6 weeks or for about 12 weeks.

The method of paragraphs 291 and 292, wherein the subject experiences no adverse events after receiving the cytisine treatment.

The method of paragraphs 291-293, wherein the adverse event is selected from the group consisting of an URTI, abnormal dreams, nausea, insomnia, headache, fatigue, and constipation.

The method of paragraphs 291-294, wherein the subject (a) smoked ten or more cigarettes per day prior to the administration of cytisine, (b) has expired air CO concentration of about 10 ppm or greater prior to the administration of cytisine, or (c) a combination of (a) and (b).

The method of paragraphs 291-295, wherein the subject is a refractory patient who has failed treatment with one or more smoking cessation treatments.

The method of paragraphs 291-296, wherein the smoking cessation treatments comprise NRT, administration of bupropion, administration of varenicline, electronic cigarettes, vaping, or a combination thereof.

A method of preventing smoking and/or vaping relapse in a subject in need thereof, the method comprising administering cytisine to the subject, wherein the subject is a refractory patient who has failed treatment with one or more smoking cessation treatments selected from the group consisting of NRT, administration of bupropion, administration of varenicline, electronic cigarettes, and vaping.

The method of paragraph 298, wherein the subject (a) smoked ten or more cigarettes per day prior to the administration of cytisine, (b) has expired air CO concentration of about 10 ppm or greater prior to the administration of cytisine, or (c) a combination of (a) and (b).

The method of paragraphs 298 and 299, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, and wherein cytisine is administered for about 6 weeks or for about 12 weeks.

The method of paragraphs 298-300, wherein the subject experiences no adverse events selected from the group consisting of an URTI, abnormal dreams, nausea, insomnia, headache, fatigue, and constipation after receiving the cytisine treatment.

A medicament comprising a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, wherein the medicament is for three times daily oral administration to the subject.

The medicament of paragraph 302, wherein the subject experiences no adverse events after receiving the cytisine treatment.

The medicament of paragraphs 302 and 303, wherein the adverse event is selected from the group consisting of an URTI, abnormal dreams, nausea, insomnia, headache, fatigue, and constipation.

The medicament of paragraphs 302-304, wherein the subject experiences no nausea after receiving the cytisine treatment.

The medicament of paragraphs 302-305, wherein cytisine is administered for about 6 weeks or for about 12 weeks.

The medicament of paragraphs 302-306, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

The medicament of paragraphs 302-307, wherein the subject is a refractory patient who has failed treatment with one or more nicotine addiction or smoking cessation treatments.

The medicament of paragraphs 302-308, wherein the nicotine addiction or smoking cessation treatments are selected from NRT, administration of bupropion, administration of varenicline, electronic cigarettes, vaping, and a combination thereof.

The medicament of paragraphs 302-309, wherein the subject (a) smoked ten or more cigarettes per day prior to the administration of cytisine, (b) has expired air CO concentration of about 10 ppm or greater prior to the administration of cytisine, or (c) a combination of (a) and (b).

The medicament of paragraphs 302-310, further comprising providing behavioral support to the subject.

A medicament comprising cytisine for treating a nicotine addiction or a nicotine dependence in a subject that is a refractory patient who has failed treatment with one or more nicotine addiction treatments, wherein the medicament is for three times daily oral administration to the subject.

The medicament of paragraph 312, wherein the nicotine addiction or dependence treatments comprise NRT, administration of bupropion, administration of varenicline, electronic cigarettes, vaping, or a combination thereof.

The medicament of paragraphs 312 and 313, wherein cytisine is provided in a unit dose of about 1.0 mg to about 6.0 mg of cytisine three to six times daily to a subject in need thereof.

The medicament of paragraphs 312-314, wherein cytisine is provided in a unit dose of 3.0 mg of cytisine three times daily to a subject in need thereof.

The medicament of paragraphs 312-315, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

The medicament of paragraphs 312-316, wherein cytisine is administered for about 6 weeks or for about 12 weeks.

The medicament of paragraphs 312-317, wherein the subject experiences no adverse events after receiving the cytisine treatment.

The medicament of paragraphs 312-318, wherein the adverse event is selected from the group consisting of an URTI, abnormal dreams, nausea, insomnia, headache, fatigue, and constipation.

The medicament of paragraphs 312-319, wherein the subject (a) smoked ten or more cigarettes per day prior to the administration of cytisine, (b) has expired air CO concentration of about 10 ppm or greater prior to the administration of cytisine, or (c) a combination of (a) and (b).

A medicament comprising a unit dose of cytisine in (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine for preventing smoking and/or vaping relapse in a subject in need thereof, wherein the medicament is for three times daily oral administration to the subject.

The medicament of paragraph 321, wherein cytisine is administered for about 6 weeks or for about 12 weeks.

The medicament of paragraphs 321 and 322, wherein the subject experiences no adverse events after receiving the cytisine treatment.

The medicament of paragraphs 321-323, wherein the adverse event is selected from the group consisting of an URTI, abnormal dreams, nausea, insomnia, headache, fatigue, and constipation.

The medicament of paragraphs 321-324, wherein the subject (a) smoked ten or more cigarettes per day prior to the administration of cytisine, (b) has expired air CO concentration of about 10 ppm or greater prior to the administration of cytisine, or (c) a combination of (a) and (b).

The medicament of paragraphs 321-325, wherein the subject is a refractory patient who has failed treatment with one or more smoking cessation treatments.

The medicament of paragraphs 321-326, wherein the smoking cessation treatments comprise NRT, administration of bupropion, administration of varenicline, electronic cigarettes, vaping, or a combination thereof.

A medicament comprising cytisine for preventing smoking and/or vaping relapse in a subject that is a refractory patient who has failed treatment with one or more nicotine addiction treatments selected from the group consisting of NRT, administration of bupropion, administration of varenicline, electronic cigarettes, and vaping, wherein the medicament is for three times daily oral administration to the subject.

The medicament of paragraph 328, wherein the subject (a) smoked ten or more cigarettes per day prior to the administration of cytisine, (b) has expired air CO concentration of about 10 ppm or greater prior to the administration of cytisine, or (c) a combination of (a) and (b).

The medicament of paragraphs 328 and 329, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, and wherein cytisine is administered for about 6 weeks or for about 12 weeks.

The medicament of paragraphs 328-330, wherein the subject experiences no adverse events selected from the group consisting of an URTI, abnormal dreams, nausea, insomnia, headache, fatigue, and constipation after receiving the cytisine treatment.

Use of a unit dose of 3.0 mg, 1.5 mg, or 1.0 mg of cytisine for treating a nicotine addiction, a nicotine dependence, promoting cessation of smoking and/or vaping, and/or promoting a reduction in smoking and/or vaping in a subject in need thereof, wherein the cytisine is for three times daily oral administration to the subject.

The use of paragraph 332, wherein the subject experiences no adverse events after receiving the cytisine treatment.

The use of paragraphs 332 and 333, wherein the adverse event is selected from the group consisting of an URTI, abnormal dreams, nausea, insomnia, headache, fatigue, and constipation.

The use of paragraphs 332-334, wherein the subject experiences no nausea after receiving the cytisine treatment.

The use of paragraphs 332-335, wherein cytisine is administered for about 6 weeks or for about 12 weeks.

The use of paragraphs 332-336, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

The use of paragraphs 332-337, wherein the subject is a refractory patient who has failed treatment with one or more nicotine addiction or smoking cessation treatments.

The use paragraphs 332-338, wherein the nicotine addiction or smoking cessation treatments are selected from NRT, administration of bupropion, administration of varenicline, electronic cigarettes, vaping, and a combination thereof.

The use of paragraphs 332-339, wherein the subject (a) smoked ten or more cigarettes per day prior to the administration of cytisine, (b) has expired air CO concentration of about 10 ppm or greater prior to the administration of cytisine, or (c) a combination of (a) and (b).

The use of paragraphs 332-340, further comprising providing behavioral support to the subject.

Use of cytisine for treating a nicotine addiction or a nicotine dependence in a subject that is a refractory patient who has failed treatment with one or more nicotine addiction treatments, wherein the cytisine is for three times daily oral administration to the subject.

The use of paragraph 342, wherein the nicotine addiction treatments comprise NRT, administration of bupropion, administration of varenicline, electronic cigarettes, vaping, or a combination thereof.

The use of paragraphs 342 and 343, wherein cytisine is provided in a unit dose of about 1.0 mg to about 6.0 mg of cytisine three to six times daily to a subject in need thereof.

The use of paragraphs 342-344, wherein cytisine is provided in a unit dose of 3.0 mg of cytisine three times daily to a subject in need thereof.

The use of paragraphs 342-345, wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

The use of paragraphs 342-346, wherein cytisine is administered for about 6 weeks or for about 12 weeks.

The use of paragraphs 342-347, wherein the subject experiences no adverse events after receiving the cytisine treatment.

The use of paragraphs 342-348, wherein the adverse event is selected from the group consisting of an URTI, abnormal dreams, nausea, insomnia, headache, fatigue, and constipation.

The use of paragraphs 342-349, wherein the subject (a) smoked ten or more cigarettes per day prior to the administration of cytisine, (b) has expired air CO concentration of about 10 ppm or greater prior to the administration of cytisine, or (c) a combination of (a) and (b).

Use of a unit dose of cytisine in the form of (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine for preventing smoking and/or vaping relapse in a subject in need thereof, wherein the cytisine is for three times daily oral administration to the subject.

The use of paragraph 351, wherein cytisine is administered for about 6 weeks or for about 12 weeks.

The use of paragraphs 351 and 352, wherein the subject experiences no adverse events after receiving the cytisine treatment.

The use of paragraphs 351-353, wherein the adverse event is selected from the group consisting of an URTI, abnormal dreams, nausea, insomnia, headache, fatigue, and constipation.

The use of paragraphs 351-354, wherein the subject (a) smoked ten or more cigarettes per day prior to the administration of cytisine, (b) has expired air CO concentration of about 10 ppm or greater prior to the administration of cytisine, or (c) a combination of (a) and (b).

The use of paragraphs 351-355, wherein the subject is a refractory patient who has failed treatment with one or more smoking cessation treatments.

The use of paragraphs 351-356, wherein the smoking cessation treatments comprise NRT, administration of bupropin, administration of varenicline, electronic cigarettes, vaping, or a combination thereof.

Use of cytisine for preventing smoking and/or vaping relapse in a subject that is a refractory patient who has failed treatment with one or more nicotine addiction treatments selected from the group consisting of NRT, administration of bupropion, administration of varenicline, electronic cigarettes, and vaping, wherein the cytisine is for three times daily oral administration to the subject.

The use of paragraph 358, wherein the subject (a) smoked ten or more cigarettes per day prior to the administration of cytisine, (b) has expired air CO concentration of about 10 ppm or greater prior to the administration of cytisine, or (c) a combination of (a) and (b).

The use of paragraphs 358 and 359 wherein the unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, and wherein cytisine is administered for about 6 weeks or for about 12 weeks.

The use of paragraphs 358-360, wherein the subject experiences no adverse events selected from the group consisting of an URTI, abnormal dreams, nausea, insomnia, headache, fatigue, and constipation after receiving the cytisine treatment.

Use of tablets comprising about 1.0 mg or about 1.5 mg of cytisine for three times daily oral administration of about 3.0 mg of cytisine to a subject to treat a nicotine addiction, a nicotine dependence, promoting cessation of smoking and/or vaping, and/or promoting a reduction in smoking and/or vaping in the subject.

The use of paragraph 362, wherein the subject experiences no adverse events after receiving the cytisine treatment.

The use of paragraphs 362 and 363, wherein the adverse event is selected from the group consisting of an URTI, abnormal dreams, nausea, insomnia, headache, fatigue, and constipation.

The use of paragraphs 362-364, wherein the subject experiences no nausea after receiving the cytisine treatment.

The use of paragraphs 362-365, wherein cytisine is administered for about 6 weeks or for about 12 weeks.

The use of paragraphs 362-366, wherein a unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine.

The use of paragraphs 362-367, wherein the subject is a refractory patient who has failed treatment with one or more nicotine addiction or smoking cessation treatments.

The use of paragraphs 362-368, wherein the nicotine addiction or smoking cessation treatments are selected from NRT, administration of bupropion, administration of varenicline, electronic cigarettes, vaping, and a combination thereof.

The use of paragraphs 362-369, wherein the subject (a) smoked ten or more cigarettes per day prior to the administration of cytisine, (b) has expired air CO concentration of about 10 ppm or greater prior to the administration of cytisine, or (c) a combination of (a) and (b).

The use of paragraphs 362-370, further comprising providing behavioral support to the subject.

Use of tablets comprising about 1.0 mg or about 1.5 mg of cytisine for three times daily oral administration of about 3.0 mg of cytisine to a subject that is a refractory patient who has failed treatment with one or more nicotine addiction treatments to treat a nicotine addiction and/or a nicotine dependence in the subject.

The use of paragraph 372, wherein the nicotine addiction treatments comprise NRT, administration of bupropion, administration of varenicline, electronic cigarettes, vaping, or a combination thereof.

The use of paragraphs 372 and 373, wherein cytisine is provided in a unit dose of about 1.0 mg to about 6.0 mg of cytisine three to six times daily to a subject in need thereof.

The use of paragraphs 372-374, wherein cytisine is provided in a unit dose of 3.0 mg of cytisine three times daily to a subject in need thereof.

The use of paragraphs 372-375, wherein the unit dose of cytisine comprises either (a) two tablets, each tablet containing 1.5 mg of cytisine, or (b) a single tablet containing 3.0 mg of cytisine.

The use of paragraphs 372-376, wherein cytisine is administered for about 6 weeks or for about 12 weeks.

The use of paragraphs 372-377, wherein the subject experiences no adverse events after receiving the cytisine treatment.

The use of paragraphs 372-378, wherein the adverse event is selected from the group consisting of an URTI, abnormal dreams, nausea, insomnia, headache, fatigue, and constipation.

The use of paragraphs 372-379, wherein the subject (a) smoked ten or more cigarettes per day prior to the administration of cytisine, (b) has expired air CO concentration of about 10 ppm or greater prior to the administration of cytisine, or (c) a combination of (a) and (b).

Use of tablets comprising about 1.0 mg or about 1.5 mg of cytisine for three times daily oral administration of about 3.0 mg of cytisine to a subject to prevent smoking and/or vaping relapse in the subject.

The use of paragraph 381, wherein cytisine is administered for about 6 weeks or for about 12 weeks.

The use of paragraphs 381 and 382, wherein the subject experiences no adverse events after receiving the cytisine treatment.

The use of paragraphs 381-383, wherein the adverse event is selected from the group consisting of an upper respiratory tract infection (URTI), abnormal dreams, nausea, insomnia, headache, fatigue, and constipation.

The use of paragraphs 381-384, wherein the subject (a) smoked ten or more cigarettes per day prior to the administration of cytisine, (b) has expired air CO concentration of about 10 ppm or greater prior to the administration of cytisine, or (c) a combination of (a) and (b).

The use of paragraphs 381-385, wherein the subject is a refractory patient who has failed treatment with one or more smoking cessation treatments.

The use of paragraphs 381-386, wherein the smoking cessation treatments comprise NRT, administration of bupropion, administration of varenicline, electronic cigarettes, vaping, or a combination thereof.

Use of tablets comprising about 1.0 mg or about 1.5 mg of cytisine for three times daily oral administration of about 3.0 mg of cytisine to a subject who has failed treatment with one or more nicotine addiction treatments selected from the group consisting of NRT, administration of bupropion, administration of varenicline, electronic cigarettes, and vaping to prevent smoking relapse in the subject.

The use of paragraph 388, wherein the subject (a) smoked ten or more cigarettes per day prior to the administration of cytisine, (b) has expired air CO concentration of about 10 ppm or greater prior to the administration of cytisine, or (c) a combination of (a) and (b).

The use of paragraphs 388 and 389, wherein a unit dose of cytisine comprises (a) two tablets, each tablet either containing 1.5 mg or 3.0 mg of cytisine, (b) a single tablet either containing 1.5 mg or 3.0 mg of cytisine, or (c) three tablets, each tablet containing 1.0 mg of cytisine, and wherein cytisine is administered for about 6 weeks or for about 12 weeks.

The use of paragraphs 388-390, wherein the subject experiences no adverse events selected from the group consisting of an URTI, abnormal dreams, nausea, insomnia, headache, fatigue, and constipation after receiving the cytisine treatment.

We claim:

1. A method of treating a nicotine dependence, treating a nicotine addiction, promoting cessation of smoking and/or vaping, and/or promoting a reduction in smoking and/or vaping in a subject in need thereof, the method comprising administering a stable 4.5 mg dose of cytisine to the subject per day for a period of at least 3 weeks, wherein the 4.5 mg dose of cytisine is present in three tablets each containing 1.5 mg of cytisine.

2. The method of claim 1, wherein the subject (a) smoked ten or more cigarettes per day prior to the administration of cytisine, (b) has expired air CO concentration of about 10 ppm or greater prior to the administration of cytisine, or (c) a combination of (a) and (b).

3. The method of claim 1, further comprising providing behavioral support to the subject.

4. A method of treating a nicotine dependence, treating a nicotine addiction, promoting cessation of smoking and/or vaping, and/or promoting a reduction in smoking and/or vaping in a subject in need thereof, the method comprising administering a stable 9 mg dose of cytisine to the subject per day for a period of at least 3 weeks, wherein the 9 mg dose of cytisine is present in six tablets each containing 1.5 mg of cytisine or three tablets each containing 3 mg of cytisine.

5. The method of claim 4, wherein the subject (a) smoked ten or more cigarettes per day prior to the administration of cytisine, (b) has expired air CO concentration of about 10 ppm or greater prior to the administration of cytisine, or (c) a combination of (a) and (b).

6. The method of claim 4, further comprising providing behavioral support to the subject.

\* \* \* \* \*